(12) United States Patent
Morsey et al.

(10) Patent No.: US 10,927,172 B2
(45) Date of Patent: *Feb. 23, 2021

(54) CANINIZED MURINE ANTIBODIES TO HUMAN PD-1

(71) Applicant: Intervet Inc., Madison, NJ (US)

(72) Inventors: Mohamad Morsey, Omaha, NE (US); Yuanzheng Zhang, Edison, NJ (US); Denise Bartels-Morozov, Fremont, NE (US); Jason Erskine, Omaha, NE (US); Ian Tarpey, St. Ives (GB); Leonard Presta, San Francisco, CA (US)

(73) Assignee: INTERVET INC., Madison, NJ (US)

( * ) Notice: Subject to any disclaimer, the term of this patent is extended or adjusted under 35 U.S.C. 154(b) by 98 days.

This patent is subject to a terminal disclaimer.

(21) Appl. No.: 16/007,077

(22) Filed: Jun. 13, 2018

(65) Prior Publication Data

US 2018/0346570 A1 Dec. 6, 2018

Related U.S. Application Data

(63) Continuation of application No. 15/104,838, filed as application No. PCT/EP2014/078665 on Dec. 19, 2014, now Pat. No. 10,023,636.

(60) Provisional application No. 61/918,847, filed on Dec. 20, 2013, provisional application No. 61/918,946, filed on Dec. 20, 2013, provisional application No. 62/030,812, filed on Jul. 30, 2014.

(51) Int. Cl.
| | | |
|---|---|---|
| *A61K 39/00* | (2006.01) | |
| *C07K 16/28* | (2006.01) | |
| *A61P 37/04* | (2006.01) | |
| *A61K 39/395* | (2006.01) | |

(52) U.S. Cl.
CPC .......... *C07K 16/2803* (2013.01); *A61K 39/00* (2013.01); *A61K 39/3955* (2013.01); *A61P 37/04* (2018.01); *C07K 16/2818* (2013.01); *C07K 16/2896* (2013.01); *A61K 2039/55516* (2013.01); *C07K 2317/24* (2013.01); *C07K 2317/34* (2013.01); *C07K 2317/52* (2013.01); *C07K 2317/565* (2013.01); *C07K 2317/76* (2013.01); *C07K 2317/92* (2013.01)

(58) Field of Classification Search
CPC .......... C07K 2317/565; C07K 2317/34; C07K 2317/24; C07K 16/2896; A61K 39/00
USPC ...................................................... 424/133.1
See application file for complete search history.

(56) References Cited

U.S. PATENT DOCUMENTS

| | | | |
|---|---|---|---|
| 6,005,079 A | 12/1999 | Casterman et al. | |
| 6,808,710 B1 | 10/2004 | Wood et al. | |
| 6,936,704 B1 | 8/2005 | Freeman et al. | |
| 7,038,013 B2 | 5/2006 | Freeman et al. | |
| 7,101,550 B2 | 9/2006 | Wood et al. | |
| 7,105,328 B2 | 9/2006 | Wood et al. | |
| 7,261,890 B2 | 8/2007 | Krah, III et al. | |
| 7,432,059 B2 | 10/2008 | Freeman et al. | |
| 7,595,048 B2 | 9/2009 | Honjo et al. | |
| 7,635,757 B2 | 12/2009 | Freeman et al. | |
| 7,638,492 B2 | 12/2009 | Wood et al. | |
| 7,700,301 B2 | 4/2010 | Wood et al. | |
| 7,709,214 B2 | 5/2010 | Freeman et al. | |
| 7,722,868 B2 | 5/2010 | Freeman et al. | |
| 8,008,449 B2 | 8/2011 | Korman et al. | |
| 8,354,509 B2 | 1/2013 | Carven et al. | |
| 8,735,553 B1 | 5/2014 | Li et al. | |
| 9,067,999 B1 | 6/2015 | Honjo et al. | |
| 10,023,636 B2* | 7/2018 | Morsey | A61K 39/3955 |
| 10,280,223 B2 | 5/2019 | Mizuno | |
| 2002/0165135 A1 | 11/2002 | McCall et al. | |
| 2007/0003546 A1 | 1/2007 | Lazar et al. | |
| 2007/0148164 A1 | 6/2007 | Farrington et al. | |
| 2010/0203056 A1 | 8/2010 | Irving | |
| 2010/0266617 A1 | 10/2010 | Carven et al. | |
| 2011/0318373 A1 | 12/2011 | Sasikumar et al. | |
| 2012/0039906 A1 | 2/2012 | Olive | |
| 2012/0237522 A1 | 9/2012 | Kang | |
| 2016/0311902 A1 | 10/2016 | Morsey et al. | |
| 2016/0333096 A1 | 11/2016 | Morsey et al. | |
| 2017/0174773 A1* | 6/2017 | Davis | C07K 16/3053 |

FOREIGN PATENT DOCUMENTS

| | | |
|---|---|---|
| EA | 1537878 | 6/2005 |
| JP | 2014140982 | 1/2016 |
| RU | 2457217 C2 | 7/2012 |
| WO | WO9404678 | 3/1994 |
| WO | WO9425591 | 11/1994 |
| WO | WO2003042402 | 5/2003 |
| WO | 2008076255 A2 | 6/2008 |
| WO | WO2008083174 A2 | 7/2008 |
| WO | WO2008156712 | 12/2008 |
| WO | 2010027488 A2 | 3/2010 |
| WO | WO2010117760 A2 | 10/2010 |

(Continued)

OTHER PUBLICATIONS

Al-Lazikani, Standard Conformations for the Canonical Structures of Immunoglobulins, J. Mol. Biol., 1997, 927-948, 273.
Alegre, A non-activating "humanized" anti-CD3 monoclonal antibody retains immunosuppressive properties in vivo, Transplantation, 1994, 1537-1543, 57.
Amgen vs. Sanofi and Regeneron, Case 17-1480, Document 176, filed Feb. 6, 2018, United States Court of Appeals for the Federal Circuit, Response to Petition for Rehearing En Banc, 27 pages.
Atherton, MJ et al., Cancer immunology and canine malignant melanoma: A comparative review, Veterinary Immunology and Immunopathology, 2016, pp. 15-26, 169.
Barber et al., Restoring function in exhausted CD8 T cells during chronic viral infection, Nature, 2006, pp. 682-687, vol. 439.

(Continued)

*Primary Examiner* — Lynn A Bristol
(74) *Attorney, Agent, or Firm* — Michael D. Davis

(57) ABSTRACT

The present invention provides caninized murine anti-human PD-1 antibodies that have specific sequences and a high binding affinity for canine PD-1. The invention also relates to use of these antibodies in the treatment of dogs.

10 Claims, 5 Drawing Sheets

Specification includes a Sequence Listing.

(56) References Cited

FOREIGN PATENT DOCUMENTS

| WO | WO2012135408 | 10/2012 |
|---|---|---|
| WO | 2012153126 A1 | 11/2012 |
| WO | 2013011407 A1 | 1/2013 |
| WO | 2013054127 A1 | 4/2013 |
| WO | WO2013124666 A1 | 8/2013 |
| WO | 2015091910 A2 | 6/2015 |
| WO | WO2015091911 | 6/2015 |
| WO | WO2016006241 | 1/2016 |

OTHER PUBLICATIONS

Bendig, Mary E., Humanization of Rodent Monoclonal Antibodies by CDR Grafting, Methods: A companion to methods in Enzymology, 1993, 83-93, 8.
Bergeron et al., Comparative functional characterization of canine IgG subclasses, Veterinary Immunology and Immunopathology, 2014, pp. 31-41, 157, WO.
Berglund, L et al., The epitope space of the human proteome, Protein Science, 2008, pp. 606-613, 17.
Brown, Blockade of Programmed Death-1 Ligands on Dendritic Cells Enhances T Cell Activation and Cytokine Production, J. Immunol., 2003, pp. 1257-1266, vol. 170.
Chan et al., Therapeutic antibodies for autoimmunity and inflammation, The Journal of Immunology, 2010, pp. 301-316, 10-5, WO.
Chothia et al., Canonical Structures for the Hypervariable Regions of Immunoglobins, J. Mol. Biol., 1987, 901-917, 196.
Chothia et al., Conformations of immunoglobin hypervariable regions, Nature, 1989, 877-883, 342.
Cobbold, et al., The immunology of companion animals: reagents and therapeutic strategies with potential veterinary and human clinical applications, Immunology Today, 1994, pp. 347-353, 15-8.
Colman, Effects of amino acid sequence changes on antibody-antigen interactions, Research Immunology, 1994, 33-36, 145.
Dong et al., Tumor-associated B7-H1 promotes T-cell apoptosis: A potential mechanism of immune evasion, Nature Medicine, 2002, pp. 793-800, vol. 8(8).
Esch, et al., Programmed Death 1-Mediated T Cell Exhaustion during Visceral Leishmaniasis Impairs Phagocyte Functioni, The Journal of Immunology, 2013, pp. 5542-5550, 191, WO.
Gearing, DP et al., A fully caninised anti-NGF monoclonal antibody for pain relief in dogs, BMC Veterinary Research, 2013, pp. 1-11, vol. 9 (226), WO.
Geczy, T et. al., Molecular basis for failure of "Atypical" C1 domain of Vav1 to bind diacylglycerol/phorbol ester, The Journal of Biological Chemistry, 2012, pp. 13137-13158, 287(16).
Hutchins, Improved bio distribution, tumor targeting and reduced immunogenicity in mice with a gamma 4 variant of CAMPATH-1H, Proc. Natl. Acad. Sci. USA, 1995, pp. 11980-11984, 92.
Ikebuchi et al., Blockade of bovine PD-1 increases T cell funtion and inhibits bovine leukemia virus expression in B cells in vitro, Veterinary Research, 2013, 1-15, 44-59.
International Search Report for PCT/EP2014/078653 dated Jul. 6, 2015, 8 pages.
International Search Report for PCT/EP2014/078655 dated Aug. 13, 2015, 14 pages.
International Search report for PCT/EP2014/078665 dated Jul. 23, 2015, 20 pages.
Iwai, Involvement of PD-L1 on tumor cells in the escape from host immune system and tumor immunotherapy by PD-L1 blockade, Proc. Natl. Acad. Sci. USA, 2002, pp. 12293-12297, vol. 99.
Jackson, et al., In Vitro Antibody Maturation, Improvement of a High Affinity, Neutralizing Antibody Against IL-1Beta, The Journal of Immunology, 1995, pp. 3310-3319, 154, WO.
Kabat, The Structural Basis of Antibody Complementarity, Adv. Prot. Chem., 1978, 1-75, 32.
Kabat, Unusual Distributions of Amino Acids in Complementarity-determining (Hypervriable) Segment of Heavy and Light Chains of Immunoglobulins and Their Possible Roles in Specificity of Antibody-combining Sites, J. Biol. Chem., 1977, 6609-6616, 252.

Khantasup, K et al., Design and generation of humanized single-chain Fv derived from mouse hybridoma for potential targeting application, Monoclonal antibodies, 2015, pp. 404-417, 34(6).
Lin, The PD-1/PD-L1 complex resembles the antigen-binding Fv domains of antibodies and T cell receptors, Proc. Natl. Acad. Sci. USA, 2008, pp. 3011-3016, vol. 105.
Lyford-Pike, et al., Evidence for a Role of the PD-1:PD-L1 Pathway in Immune Resistance of HPV-Associated Head and Neck Squamous Cell Carcinoma, Cancer Research, 2012, pp. 1733-1741, 73-6, WO.
McDermott, et al., PD-1 as a potential target in cancer therapy, Cancer Medicine, 2013, pp. 662-673, WO.
McEarchern, Engineered anti-CD70 antibody with multiple effector functions exhibits in vitro and in vivo antitumor activities, Blood, 2007, 1185-1192, 109.
Muyldermans, Recognition of antigens by single-domain antibody fragments: the superfluous luxury of paired domains, Trends Biochem. Sci., 2001, 230-235, 26.
National Service Foundation Award Abstract #1262435, ABI Innovation: Predicting the combined impact of multiple nutations on protein functional adaptation, 2012, 2 pages.
NCBI Reference Sequence: XP_543338.3, Sep. 24, 2013, XP055179334, retrieved from Internet: URL:http://www.ncbi.nlm.nih.gov/protein/XP_543338.
Nomi et al., Clinical Significance and Therapeutic Potential of the Programmed Death-1 Ligand/Programmed Death-1 Pathway in Human Pancreatic Cancer, Clinical Cancer Research, 2007, pp. 2151-2157, vol. 13.
Okazaki, PD-1 and PD-1 ligands: from discovery to clinical application, Int. Immunol., 2007, pp. 813-824, vol. 19.
Paul, WE, Fundamental Immunology, Fundamental Immunolgy, third edition, 1993, 292-295, Third Edition.
Reichmann, Single domain antibodies: comparison of camel VH and camelised human VH domains, J. Immunol. Methods, 1999, 25-38, 231.
Roguin, LP et al., Monoclonal antibodies inducing conformational changes on the antigen molecule, Scandinaavian Journal of Immunology, 2003, pp. 387-394, 58.
Rudikoff, Single amino acid substitution altering antigen-binding specificity, Proc. Natl. Acad. Sci. USA, 1982, pp. 1979-1983, vol. 79.
Sazinsky, Aglycosylated immunoglobin G1 variants productively engage activating Fc receptors, Proc. Natl. Acad. Sci., 2008, 20167-20172, 105.
Shields, High Resolution Mapping of the Binding Site on Human IgG1 for FcγRI, FcγRII, FcγRIII, and FcRn and Design of IgG1 Variants with Improved Binding to the FcγR, J. of Biol. Chem., 2001, 6591-6604, 276-9.
Strome et al., B7-H1 Blockade Augments Adoptive T-Cell Immunotherapy for Squamous Cell Cancinoma, Cancer Research, 2003, pp. 6501-6505, vol. 63.
Tang et al., Cloning and characterization of cDNAs encoding four different canine immunoglobulin Y chains, Veterinary Immunology and Immunopathology, 2001, pp. 259-270, 80.
Thompson et al., PD-1 Is Expressed by Tumor-Infiltrating Immune Cells and Is Associated with Poor Outcome for Patients with Renal Cell Carcinoma, Clinical Cancer Research, 2007, pp. 1757-1761, vol. 15.
Thompson et al., Tumor B7-H1 Is Associated with Poor Prognosis in Renal Cell Carcinoma Patients with Long-Term Follow-up, Cancer Res., 2006, pp. 3381-3385, vol. 66.
Tsushima et al., Predominant expression of B7-H1 and its immunoregulatory roles in oral squamous cell carcinoma, Oral Oncol., 2006, pp. 268-274, vol. 42.
Tzartos, SJ, Epitope mapping by antibody competition, Methods in Molecular Biology, 1996, pp. 55-66, 66.
Wintterle et al., Expression of the B7-Related Molecule B7-H1 by Glioma Cells: A Potential Mechanism of Immune Paralysis, Cancer Res., 2003, pp. 7462-7467, vol. 63.
Wong, et al., Structural Requirements for a Specificity Switch and for Maintenance of Affinity Using Mutational Analysis of a Phage-Displayed Anti-Arsonate Antibody of Fab Heavy Chain First Complementarity-Determining Region, Journal of Immunology, 1998, pp. 5990-5997, 160, WO.

(56) References Cited

OTHER PUBLICATIONS

Zhang et al., Structural and Functional Analysis of the Costimulatory Receptor Programmed Death-1, Immunity, 2004, pp. 337-347, vol. 20.
Folkl, A et al., Feline programmed death and its ligand: Characterization and changes with feline immunodeficiency virus infection, Veterinary Immunology and Immunopathology, 2010, 107-114, 134.
U.S. Appl. No. 15/104,838, filed Jun. 15, 2016.

* cited by examiner

Figure 1. Reactivity of mouse 08A mAb against His-tagged extracellular domain of canine PD-1.
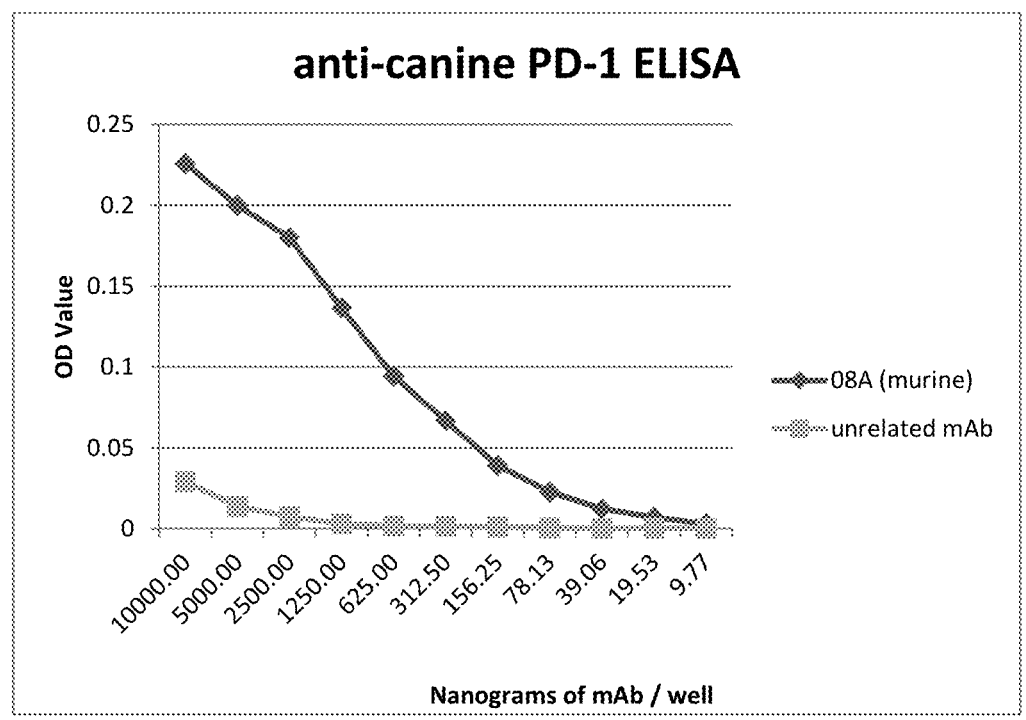

Figure 2: *Reactivity of mouse 08A mAbs against Canine PD-1 proteins expressed on CHO cells using CELISA. Murine 08A antibody and its caninized variants react with PD-1 in a dose dependent manner.*
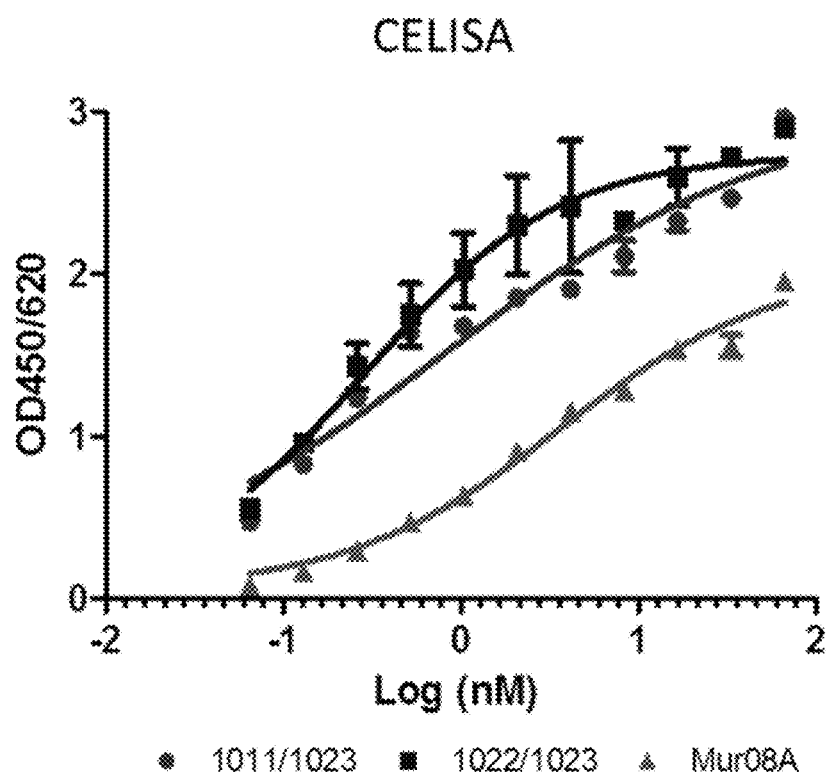

Figure 3. ligand blockade by mouse and caninized antibodies. Murine 08A and its caninized variants block binding of canine PD-1 to PD-1 expressed on CHO cell surface.
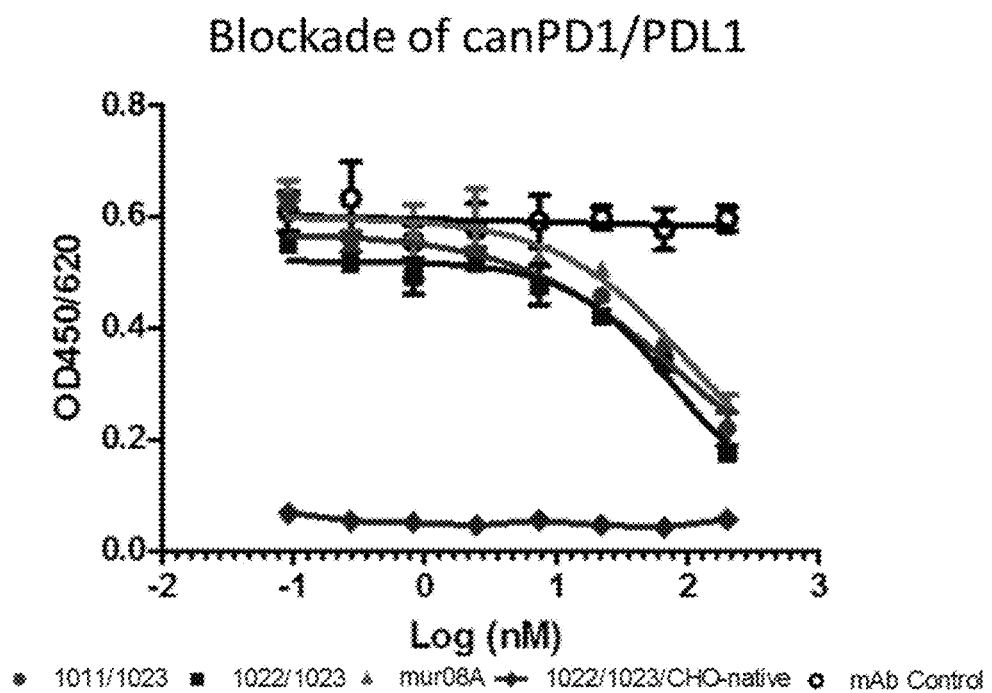

Alignment of canine IgGB CHs lacking ADCC function

```
cIgGB wt          SASTTAPSVFPLAPSCGSTSGSTVALACLVSGYFPEPVTVSWNSGSLTSGVHTFPSVLQSSGLYSLSSMVTVPSSRWPSETFTCNVAHPASKTKVDKPVPKRENGRVPRPPDCPKCPAPE
cIgGB(+)A-hinge   SASTTAPSVFPLAPSCGSTSGSTVALACLVSGYFPEPVTVSWNSGSLTSGVHTFPSVLQSSGLYSLSSMVTVPSSRWPSETFTCNVAHPASKTKVDKPVPKRENGRVPRPPDCPKCPAPE
cIgGB(+)D-hinge   SASTTAPSVFPLAPSCGSTSGSTVALACLVSGYFPEPVTVSWNSGSLTSGVHTFPSVLQSSGLYSLSSMVTVPSSRWPSETFTCNVAHPASKTKVDKPVPKRENGRVPKES-----TCKCISPCPAPE
cIgGB(-)ADCC      SASTTAPSVFPLAPSCGSTSGSTVALACLVSGYFPEPVTVSWNSGSLTSGVHTFPSVLQSSGLYSLSSMVTVPSSRWPSETFTCNVAHPASKTKVDKPVPKRENGRVPRPPDCPKCPAPE cIgGB             MLGGPSVFIFPPKPKDTILLIARTPEVTCVVVDLPEDPEVQISWFVDGKQMQTAKTQPREEQFNGTYRVVSVLPIGHQDWLKGKQFTCKVNNKALPSPIERTISKARGQAHQPSVYVLPP
cIgGB(+)A-hinge   MLGGPSVFIFPPKPKATILLIARTPEVTCVVVDLPEDPEVQISWFVDGKQMQTAKTQPREEQFAGTYRVVSVLPIGHQDWLKGKQFTCKVNNKALPSPIERTISKARGQAHQPSVYVLPP
cIgGB(+)D-hinge   MLGGPSVFIFPPKPKATILLIARTPEVTCVVVDLPEDPEVQISWFVDGKQMQTAKTQPREEQFAGTYRVVSVLPIGHQDWLKGKQFTCKVNNKALPSPIERTISKARGQAHQPSVYVLPP
cIgGB(-)ADCC      MLGGPSVFIFPPKPKPKATILLIARTPEVTCVVVDLPEDPEVQISWFVDGKQMQTAKTQPREEQFAGTYRVVSVLPIGHQDWLKGKQFTCKVNNKALPSPIERTISKARGQAHQPSVYVLPP canIgGB           SREELSKNTVSLTCLIKDFFPPDIDVEWQSNGQQEPESKYRTTPPQLDEDGSYFLYSKLSVDKSRWQRGDTFICAVMHEALHNHYTQESLSHSPGK
cIgGB(+)A-hinge   SREELSKNTVSLTCLIKDFFPPDIDVEWQSNGQQEPESKYRTTPPQLDEDGSYFLYSKLSVDKSRWQRGDTFICAVMHEALHNHYTQESLSHSPGK
cIgGB(+)D-hinge   SREELSKNTVSLTCLIKDFFPPDIDVEWQSNGQQEPESKYRTTPPQLDEDGSYFLYSKLSVDKSRWQRGDTFICAVMHEALHNHYTQESLSHSPGK
cIgGB(-)ADCC      SREELSKNTVSLTCLIKDFFPPDIDVEWQSNGQQEPESKYRTTPPQLDEDGSYFLYSKLSVDKSRWQRGDTFICAVMHEALHNHYTQESLSHSPGK
```

FIG.4A cIgGB wt

SASTTAPSVFPLAPSCGSTSGSTVALACLVSGYFPEPVTVSWNSGSLTSGVHTFPSVLQSSGLYSLSSMVTVPSSRWPSETFTCNVAHPASKTKVDKPVPKRENCRVPRPPDCPKCPAPEMLGGPSVFIFPPKPDT LLIARTPEVTCVVVDLDPEDPEVQISWFVDGKQMQTAKTQPREEQFNGTYRVVSVLPIGHQDWLKGKQFTCKVNNKALPSPIERTISKARGQAHQPSVYVLPPSREELSKNTVSLTCLIKDFFPPDIDVEWQSNGQQ EPESKYRTTPPQLDEDGSYFLYSKLSVDKSRWQRGDTFICAVMHEALHNHYTQESLSHSPGK cIgGB(+)A-hinge SASTTAPSVFPLAPSCGSTSGSTVALACLVSGYFPEPVTVSWNSGSLTSGVHTFPSVLQSSGLYSLSSMVTVPSSRWPSETFTCNVAHPASKTKVDKPVFNECRCTDTPPCPAPEMLGGPSVFIFPPKATLLIAR TPEVTCVVVDLDPEDPEVQISWFVDGKQMQTAKTQPREEQFAGTYRVVSVLPIGHQDWLKGKQFTCKVNNKALPSPIERTISKARGQAHQPSVYVLPPSREELSKNTVSLTCLIKDFFPPDIDVEWQSNGQQEPESK YRTTPPQLDEDGSYFLYSKLSVDKSRWQRGDTFICAVMHEALHNHYTQESLSHSPGK cIgGB(+)D-hinge SASTTAPSVFPLAPSCGSTSGSTVALACLVSGYFPEPVTVSWNSGSLTSGVHTFPSVLQSSGLYSLSSMVTVPSSRWPSETFTCNVAHPASKTKVDKPVPKESTCKCISPCPAPEMLGGPSVFIFPPKATLLIAR TPEVTCVVVDLDPEDPEVQISWFVDGKQMQTAKTQPREEQFAGTYRVVSVLPIGHQDWLKGKQFTCKVNNKALPSPIERTISKARGQAHQPSVYVLPPSREELSKNTVSLTCLIKDFFPPDIDVEWQSNGQQEPESK YRTTPPQLDEDGSYFLYSKLSVDKSRWQRGDTFICAVMHEALHNHYTQESLSHSPGK cIgGB(-)ADCC SASTTAPSVFPLAPSCGSTSGSTVALACLVSGYFPEPVTVSWNSGSLTSGVHTFPSVLQSSGLYSLSSMVTVPSSRWPSETFTCNVAHPASKTKVDKPVPKRENCRVPRPPDCPKCPAPEMLGGPSVFIFPPKAT LLIARTPEVTCVVVDLDPEDPEVQISWFVDGKQMQTAKTQPREEQFAGTYRVVSVLPIGHQDWLKGKQFTCKVNNKALPSPIERTISKARGQAHQPSVYVLPPSREELSKNTVSLTCLIKDFFPPDIDVEWQSNGQQ EPESKYRTTPPQLDEDGSYFLYSKLSVDKSRWQRGDTFICAVMHEALHNHYTQESLSHSPGK

FIG.4B

CANINIZED MURINE ANTIBODIES TO HUMAN PD-1

CROSS-REFERENCE TO RELATED APPLICATIONS

This application is a continuation of co-pending U.S. application Ser. No. 15/104,838 filed on Jun. 15, 2016, which is a national stage entry under 35 U.S.C. § 371 of PCT/EP2014/078665, filed on Dec. 19, 2014, which claims priority to U.S. Provisional Application No. 62/030,812, filed on Jul. 30, 2014, U.S. Provisional Application No. 61/918,847, filed Dec. 20, 2013, and U.S. Provisional Application No. 61/918,946, filed Dec. 20, 2013. The contents of all of which are hereby incorporated by reference in their entireties.

FIELD OF THE INVENTION

The present invention relates to caninized murine antibodies to human PD-1 that have specific sequences and a high binding affinity for canine PD-1. The invention also relates to use of the antibodies of the present invention in the treatment of cancer in dogs.

BACKGROUND OF THE INVENTION

An immunoinhibitory receptor that is primarily expressed on activated T and B cells, Programmed Cell Death Receptor 1, also referred to as Programmed Death Receptor (PD-1), is a member of the immunoglobulin superfamily related to CD28 and CTLA-4. PD-1 and like family members are type I transmembrane glycoproteins containing an extracellular Ig Variable-type (V-type) domain that binds its ligands and a cytoplasmic tail that binds signaling molecules. The cytoplasmic tail of PD-1 contains two tyrosine-based signaling motifs, an ITIM (immunoreceptor tyrosine-based inhibition motif) and an ITSM (immunoreceptor tyrosine-based switch motif).

PD-1 attenuates T-cell responses when bound to Programmed Cell Death Ligand 1, also referred to as Programmed Death Ligand 1 (PD-L1), and/or Programmed Cell Death Ligand 2, also referred to as Programmed Death Ligand 2 (PD-L2). The binding of either of these ligands to PD-1 negatively regulates antigen receptor signaling. Blocking the binding of PD-L1 to PD-1 enhances tumor-specific CD8$^+$ T-cell immunity, while aiding the clearance of tumor cells by the immune system. The three-dimensional structure of murine PD-1, as well as the co-crystal structure of mouse PD-1 with human PD-L1 have been reported [Zhang et al., *Immunity* 20: 337-347 (2004); Lin et al., *Proc. Natl. Acad. Sci. USA* 105: 3011-3016 (2008)].

PD-L1 and PD-L2 are type I transmembrane ligands that contain both IgV- and IgC-like domains in the extracellular region along with short cytoplasmic regions with no known signaling motifs. Both PD-L1 and PD-L2 are either constitutively expressed or can be induced in a variety of cell types, including non-hematopoietic tissues as well as various tumor types. PD-L1 is not only expressed on B, T, myeloid and dendritic cells (DCs), but also on peripheral cells, such as microvascular endothelial cells and non-lymphoid organs e.g., heart or lung. In contrast, PD-L2 is only found on macrophages and DCs. The expression pattern of PD-1 ligands suggests that PD-1 plays a role in maintaining peripheral tolerance and may further serve to regulate self-reactive T- and B-cell responses in the periphery.

In any case, it is now abundantly clear that PD-1 plays a critical role in at least certain human cancers, presumably by mediating immune evasion. Accordingly, PD-L1 has been shown to be expressed on a number of mouse and human tumors and is inducible by IFN gamma in the majority of PD-L1 negative tumor cell lines [Iwai et al., *Proc. Natl. Acad. Sci. U.S.A.* 99: 12293-12297 (2002); Strome et al., *Cancer Res.*, 63: 6501-6505 (2003)]. Furthermore, the expression of PD-1 on tumor infiltrating lymphocytes and/or PD-L1 on tumor cells has been identified in a number of primary human tumor biopsies. Such tumor tissues include cancers of the lung, liver, ovary, cervix, skin, colon, glioma, bladder, breast, kidney, esophagus, stomach, oral squamous cell, urothelial cell, and pancreas, as well as tumors of the head and neck [Brown et al., *J. Immunol.* 170: 1257-1266 (2003); Dong et al., *Nat. Med.* 8: 793-800 (2002); Wintterle et al., *Cancer Res.* 63: 7462-7467 (2003); Strome et al., *Cancer Res.*, 63: 6501-6505 (2003); Thompson et al., *Cancer Res.* 66: 3381-5 (2006); Thompson et al., *Clin. Cancer Res.* 13: 1757-1761 (2007); Nomi et al., *Clin. Cancer Res.* 13: 2151-2157. (2007)]. More strikingly, PD-ligand expression on tumor cells has been correlated to poor prognosis of human cancer patients across multiple tumor types [reviewed in Okazaki and Honjo, *Int. Immunol.* 19: 813-824 (2007)].

Moreover, Nomi et al. [*Clin. Cancer Res.* 13: 2151-2157 (2007)] demonstrated the therapeutic efficacy of blocking the binding of PD-L1 to PD-1 in a murine model of aggressive pancreatic cancer through administering either PD-1 or PD-L1 directed antibody. These antibodies effectively promoted tumor reactive CD8$^+$ T cell infiltration into the tumor resulting in the up-regulation of anti-tumor effectors including IFN gamma, granzyme B, and perforin. Similarly, the use of antibodies to block the binding of PD-L1 and PD-1 significantly inhibited tumor growth in a model of mouse squamous cell carcinoma [Tsushima et al., *Oral Oncol.* 42: 268-274 (2006)].

In other studies, transfection of a murine mastocytoma line with PD-L1 led to decreased lysis of the tumor cells when co-cultured with a tumor-specific CTL clone. Lysis was restored when anti-PD-L1 monoclonal antibody was added [Iwai et al., *Proc. Natl. Acad. Sci. U.S.A.* 99: 12293-12297 (2002)]. In vivo, blocking the PD1/PD-L1 interaction was shown to increase the efficacy of adoptive T cell transfer therapy in a mouse tumor model [Strome et al., *Cancer Res.* 63: 6501-6505 (2003)]. Further evidence for the role of PD-1 in cancer treatment comes from experiments performed with PD-1 knockout mice in which PD-L1 expressing myeloma cells grew only in wild-type animals (resulting in tumor growth and associated animal death), but not in PD-1 deficient mice [Iwai Y. et al., *Proc. Natl. Acad. Sci. U.S.A.* 99: 12293-12297 (2002)]. More recently, antibodies against PD-1 (including humanized murine monoclonal antibodies against human PD-1) have shown at least initial success in cancer therapy in humans [see e.g., U.S. Pat. No. 8,354,509 B2, U.S. Pat. No. 8,008,449 B2, and U.S. Pat. No. 7,595,048 B2].

Anti-PD-1 antibodies may also be useful in chronic viral infection. Memory CD8$^+$ T cells generated after an acute viral infection are highly functional and constitute an important component of protective immunity. In contrast, chronic infections are often characterized by varying degrees of functional impairment (exhaustion) of virus-specific T-cell responses, and this defect is a principal reason for the inability of the host to eliminate the persisting pathogen. Although functional effector T cells are initially generated during the early stages of infection, they gradually lose function during the course of a chronic infection. Barber et al. [*Nature* 439: 682-687 (2006)] showed that mice infected with a laboratory strain of LCMV developed chronic infection resulted in high levels of virus in the blood and other tissues. These mice initially developed a robust T cell response, but eventually succumbed to the infection upon T cell exhaustion. Barber et al. found that the decline in number and function of the effector T cells in chronically infected mice could be reversed by injecting an antibody that blocked the interaction between PD-1 and PD-L1.

The citation of any reference herein should not be construed as an admission that such reference is available as "prior art" to the instant application.

SUMMARY OF THE INVENTION

The present invention relates to caninized murine anti-human PD-1 antibodies that have a high binding affinity to canine PD-1, as well as having the ability to block the binding of canine PD-1 to canine PD-L1. The present invention also relates to use of such antibodies in the treatment of disease such as cancer and/or those due to infections.

Accordingly, the present invention provides an isolated caninized antibody or antigen binding fragment thereof that specifically binds Programmed Death Receptor 1 (PD-1) comprising a canine IgG heavy chain and a canine kappa or lambda light chain. In particular embodiments of this type, the canine kappa or lambda light chain that comprises three light chain complementary determining regions (CDRs): CDR light 1 (CDRL1), CDR light 2 (CDRL2), and CDR light 3 (CDRL3); and the canine IgG heavy chain comprises three heavy chain CDRs: CDR heavy 1 (CDRH1), CDR heavy 2 (CDRH2) and CDR heavy 3 (CDRH3) obtained from a mammalian PD-1 antibody. Particular embodiments of the caninized antibodies and fragments thereof of the present invention bind canine PD-1 and/or block the binding of canine PD-1 to canine Programmed Death Ligand 1 (PD-L1).

In certain embodiments, canine light chain is a kappa chain. In particular embodiments of this type, the CDRL1 comprises the amino acid sequence of SEQ ID NO: 20. In related embodiments the CDRL1 comprises a conservatively modified variant of SEQ ID NO: 20. In other embodiments, the CDRL2 comprises the amino acid sequence comprising SEQ ID NO: 22. In related embodiments the CDRL2 comprises a conservatively modified variant of SEQ ID NO: 22. In still other embodiments the CDRL3 comprises the amino acid sequence of SEQ ID NO: 24. In related embodiments the CDRL3 comprises a conservatively modified variant of SEQ ID NO: 24. In yet other embodiments the CDRH1 comprises the amino acid sequence of SEQ ID NO: 14. In related embodiments the CDRH1 comprises a conservatively modified variant of SEQ ID NO: 14. In still other embodiments the CDRH2 comprises the amino acid sequence of SEQ ID NO: 16. In related embodiments the CDRH2 comprises a conservatively modified variant of SEQ ID NO: 16. In yet other embodiments the CDRH3 comprises the amino acid sequence of SEQ ID NO: 18. In related embodiments the CDRH3 comprises a conservatively modified variant of SEQ ID NO: 18.

In specific embodiments the CDRL1 comprises the amino acid sequence of SEQ ID NO: 20 or a conservatively modified variant of SEQ ID NO: 20, the CDRL2 comprises the amino acid sequence comprising SEQ ID NO: 22 or a conservatively modified variant of SEQ ID NO: 22, and the CDRL3 comprises the amino acid sequence of SEQ ID NO: 24 or a conservatively modified variant of SEQ ID NO: 24.

In other specific embodiments the CDRH1 comprises the amino acid sequence of SEQ ID NO: 14 or a conservatively modified variant of SEQ ID NO: 14, the CDRH2 comprises the amino acid sequence comprising SEQ ID NO: 16 or a conservatively modified variant of SEQ ID NO: 16, and the CDRH3 comprises the amino acid sequence of SEQ ID NO: 18 or a conservatively modified variant of SEQ ID NO: 18.

In a more specific embodiment the CDRL1 comprises the amino acid sequence of SEQ ID NO: 20 or a conservatively modified variant of SEQ ID NO: 20, the CDRL2 comprises the amino acid sequence comprising SEQ ID NO: 22 or a conservatively modified variant of SEQ ID NO: 22, and the CDRL3 comprises the amino acid sequence of SEQ ID NO: 24 or a conservatively modified variant of SEQ ID NO: 24, and the CDRH1 comprises the amino acid sequence of SEQ ID NO: 14 or a conservatively modified variant of SEQ ID NO: 14, the CDRH2 comprises the amino acid sequence comprising SEQ ID NO: 16 or a conservatively modified variant of SEQ ID NO: 16, and the CDRH3 comprises the amino acid sequence of SEQ ID NO: 18 or a conservatively modified variant of SEQ ID NO: 18.

In an even more specific embodiment the CDRL1 comprises the amino acid sequence of SEQ ID NO: 20, the CDRL2 comprises the amino acid sequence comprising SEQ ID NO: 22, and the CDRL3 comprises the amino acid sequence of SEQ ID NO: 24, the CDRH1 comprises the amino acid sequence of SEQ ID NO: 14, the CDRH2 comprises the amino acid sequence comprising SEQ ID NO: 16, and the CDRH3 comprises the amino acid sequence of SEQ ID NO: 18.

For embodiments of the present invention, the IgG heavy chain comprises an amino acid sequence of SEQ ID NO: 26. In related embodiments the IgG heavy chain comprises a conservatively modified variant of SEQ ID NO: 26. In other embodiments the IgG heavy chain comprises an amino acid sequence of SEQ ID NO: 28. In related embodiments the IgG heavy chain comprises a conservatively modified variant of SEQ ID NO: 28. In still other embodiments the IgG heavy chain comprises an amino acid sequence of SEQ ID NO: 30. In related embodiments the IgG heavy chain comprises a conservatively modified variant of SEQ ID NO: 30.

In certain embodiments the kappa light chain comprises an amino acid sequence of SEQ ID NO: 32. In related embodiments, the kappa light chain comprises conservatively modified variant of SEQ ID NO: 32. In particular embodiments the kappa light chain comprises an amino acid sequence of SEQ ID NO: 34. In related embodiments, the kappa light chain comprises conservatively modified variant of SEQ ID NO: 34.

In a more particular embodiment, an isolated caninized antibody comprises the amino acid sequence of SEQ ID NO: 28 and of SEQ ID NO: 34. In related embodiments the isolated caninized antibody comprises a conservatively modified variant of SEQ ID NO: 28 and a conservatively modified variant of SEQ ID NO: 34. In still other related embodiment the isolated caninized antibody comprises the amino acid sequence of SEQ ID NO: 28 and a conservatively modified variant of SEQ ID NO: 34. In yet other related embodiment the isolated caninized antibody comprises a conservatively modified variant of SEQ ID NO: 28 and the amino acid sequence of SEQ ID NO: 34.

The present invention further provides isolated nucleic acids that encode any one of the light chains of the caninized antibody of the present invention. Similarly, the present invention further provides isolated nucleic acids that encode any one of the heavy chains of the caninized antibody of the present invention. The present invention further provides expression vectors that comprise one or more of the isolated nucleic acids of the present invention. The present invention further provides host cells that comprise one or more expression vectors of the present invention.

In particular embodiments, the antibody is a recombinant antibody or an antigen binding fragment thereof. In related embodiments, the variable heavy chain domain and variable light chain domain are connected by a flexible linker to form a single-chain antibody.

In particular embodiments, the antibody or antigen binding fragment is a Fab fragment.

In other embodiments, the antibody or antigen binding fragment is a Fab' fragment. In other embodiments, the antibody or antigen binding fragment is a (Fab')$_2$ fragment. In still other embodiments, the antibody or antigen binding fragment is a diabody. In particular embodiments, the antibody or antigen binding fragment is a domain antibody. In particular embodiments, the antibody or antigen binding fragment is a camelized single domain antibody.

In particular embodiments, the caninized murine anti-human PD-1 antibody or antigen binding fragment increases the immune response of the canine subject being treated.

The present invention further provides isolated nucleic acids that encode the caninized murine anti-human PD-1 antibodies or antigen binding fragments as disclosed herein. In related embodiments such antibodies or antigen binding fragments can be used for the preparation of a medicament to treat cancer in a canine subject. Alternatively, or in conjunction, the present invention provides for the use of any of the antibodies or antibody fragments of the present invention for diagnostic use. In yet additional embodiments, a kit is provided comprising any of the caninized antibodies or antigen binding fragments disclosed herein.

In yet additional embodiments, an expression vector is provided comprising an isolated nucleic acid encoding any of the caninized murine anti-human PD-1 antibodies or antigen binding fragments of the invention. The invention also relates to a host cell comprising any of the expression vectors described herein. In particular embodiments, these nucleic acids, expression vectors or polypeptides of the invention are useful in methods of making an antibody.

The present invention further includes pharmaceutical compositions comprising an antibody or antigen binding fragment thereof together with a pharmaceutically acceptable carrier or diluent. In addition, the present invention provides methods of increasing the activity of an immune cell, comprising administering to a subject in need thereof a therapeutically effective amount of such pharmaceutical compositions. In certain embodiments the method is used for the treatment of cancer. In other embodiments, the method is used in the treatment of an infection or infectious disease. In still other embodiments, a caninized antibody of the present invention or antigen binding fragment thereof is used as a vaccine adjuvant.

These and other aspects of the present invention will be better appreciated by reference to the following Brief Description of the Drawings and the Detailed Description.

BRIEF DESCRIPTION OF THE DRAWINGS

FIG. 1 shows the reactivity of murine anti-human PD-1 monoclonal antibody 08A [mAb 08A; as first described in U.S. Pat. No. 8,354,509 B2 in relation to human PD-1] against the His-tagged extracellular domain of canine PD-1.

FIG. 2 shows the reactivity of murine anti-human PD-1 monoclonal antibody 08A (see above) against canine PD-1 proteins expressed on CHO cells using CELISA. Murine anti-human PD-1 monoclonal antibody 08A and its caninized variants were found to react with canine PD-1 in a dose dependent manner.

FIG. 3 depicts the ligand blockade by murine and caninized monoclonal antibodies. Murine anti-human PD-1 monoclonal antibody 08A (see above) and its caninized variants blocked the binding of canine PD-L1 to PD-1 expressed on CHO cell surface.

FIGS. 4A-4B provide the alignment of canine IgGB constant heavy chains (CHs) lacking ADCC function. The amino acid sequences of the Canine wild type IgB [cIgGB wt] having the amino acid sequence of SEQ ID NO: 49, Canine IgGB(+)A-hinge [cIgGB(+) A-hinge] having the amino acid sequence of SEQ ID NO: 50, Canine IgGB(+) D-hinge [cIgGB(+) D-hinge] having the amino acid sequence of SEQ ID NO: 51, and Canine IgGB (−) ADCC [cIgGB(−) ADCC] having the amino acid sequence of SEQ ID NO: 52, are depicted. The (+) A-hinge is the replacement with IgG-A hinge plus an aspartic acid and asparagine amino acid replacement as shown; the (+) D-hinge is the replacement with IgG-D hinge plus the aspartic acid and the asparagine amino acid replacement as shown. The (−)ADCC is the aspartic acid and asparagine amino acid replacement.

DETAILED DESCRIPTION

Abbreviations

Throughout the detailed description and examples of the invention the following abbreviations will be used:
ADCC Antibody-dependent cellular cytotoxicity
CDC Complement-dependent cytotoxicity
CDR Complementarity determining region in the immunoglobulin variable regions, defined using the Kabat numbering system
CHO Chinese hamster ovary
EC50 concentration resulting in 50% efficacy or binding
ELISA Enzyme-linked immunosorbant assay
FR Antibody framework region: the immunoglobulin variable regions excluding the CDR regions.
HRP Horseradish peroxidase
IFN interferon
IC50 concentration resulting in 50% inhibition
IgG Immunoglobulin G
Kabat An immunoglobulin alignment and numbering system pioneered by Elvin A. Kabat [*Sequences of Proteins of Immunological Interest*, 5th Ed. Public Health Service, National Institutes of Health, Bethesda, Md. (1991)]
mAb Monoclonal antibody (also Mab or MAb)
MES 2-(N-morpholino)ethanesulfonic acid
MOA Mechanism of action
NHS Normal human serum
PCR Polymerase chain reaction
PK Pharmacokinetics
SEB *Staphylococcus* Enterotoxin B
TT Tetanus toxoid
V region The segment of IgG chains which is variable in sequence between different antibodies. It extends to Kabat residue 109 in the light chain and 113 in the heavy chain.
VH Immunoglobulin heavy chain variable region
VK Immunoglobulin kappa light chain variable region Definitions So that the invention may be more readily understood, certain technical and scientific terms are specifically defined below. Unless specifically defined elsewhere in this document, all other technical and scientific terms used herein have the meaning commonly understood by one of ordinary skill in the art to which this invention belongs.

As used herein, including the appended claims, the singular forms of words such as "a," "an," and "the," include their corresponding plural references unless the context clearly dictates otherwise.

"Activation" as it applies to cells or to receptors refers to the activation or treatment of a cell or receptor with a ligand, unless indicated otherwise by the context or explicitly. "Ligand" encompasses natural and synthetic ligands, e.g., cytokines, cytokine variants, analogues, muteins, and binding compounds derived from antibodies. "Ligand" also encompasses small molecules, e.g., peptide mimetics of cytokines and peptide mimetics of antibodies.

"Activation" can refer to cell activation as regulated by internal mechanisms as well as by external or environmental factors.

"Activity" of a molecule may describe or refer to the binding of the molecule to a ligand or to a receptor, to catalytic activity; to the ability to stimulate gene expression or cell signaling, differentiation, or maturation; to antigenic activity, to the modulation of activities of other molecules, and the like. "Activity" of a molecule may also refer to activity in modulating or maintaining cell-to-cell interactions, e.g., adhesion, or activity in maintaining a structure of a cell, e.g., cell membranes or cytoskeleton. "Activity" can also mean specific activity, e.g., [catalytic activity]/[mg protein], or [immunological activity]/[mg protein], concentration in a biological compartment, or the like. "Activity" may refer to modulation of components of the innate or the adaptive immune systems.

"Administration" and "treatment," as it applies to an animal, e.g., a canine experimental subject, cell, tissue, organ, or biological fluid, refers to contact of an exogenous pharmaceutical, therapeutic, diagnostic agent, or composition to the animal e.g., a canine subject, cell, tissue, organ, or biological fluid. Treatment of a cell encompasses contact of a reagent to the cell, as well as contact of a reagent to a fluid, where the fluid is in contact with the cell. "Administration" and "treatment" also means in vitro and ex vivo treatments, e.g., of a cell, by a reagent, diagnostic, binding compound, or by another cell. The term "subject" includes any organism, preferably an animal, more preferably a mammal (e.g., canine, feline, or human) and most preferably a canine.

"Treat" or "treating" means to administer a therapeutic agent, such as a composition containing any of the antibodies or antigen binding fragments of the present invention, internally or externally to a canine subject or patient having one or more disease symptoms, or being suspected of having a disease, for which the agent has therapeutic activity. Typically, the agent is administered in an amount effective to alleviate and/or ameliorate one or more disease symptoms in the treated subject or population, whether by inducing the regression of or inhibiting the progression of such symptom(s) by any clinically measurable degree. The amount of a therapeutic agent that is effective to alleviate any particular disease symptom (also referred to as the "therapeutically effective amount") may vary according to factors such as the disease state, age, and weight of the patient (e.g., canine), and the ability of the pharmaceutical composition to elicit a desired response in the subject. Whether a disease symptom has been alleviated or ameliorated can be assessed by any clinical measurement typically used by veterinarians or other skilled healthcare providers to assess the severity or progression status of that symptom. While an embodiment of the present invention (e.g., a treatment method or article of manufacture) may not be effective in alleviating the target disease symptom(s) in every subject, it should alleviate the target disease symptom(s) in a statistically significant number of subjects as determined by any statistical test known in the art such as the Student's t-test, the $chi^2$-test, the U-test according to Mann and Whitney, the Kruskal-Wallis test (H-test), Jonckheere-Terpstra-test and the Wilcoxon-test.

"Treatment," as it applies to a human, veterinary (e.g., canine) or research subject, refers to therapeutic treatment, as well as research and diagnostic applications. "Treatment" as it applies to a human, veterinary (e.g., canine), or research subject, or cell, tissue, or organ, encompasses contact of the antibodies or antigen binding fragments of the present invention to a canine or other animal subject, a cell, tissue, physiological compartment, or physiological fluid.

Canine PD-1 has been found to comprise the amino acid sequence of SEQ ID NO: 2. In a specific embodiment canine PD-1 is encoded by a nucleic acid that comprises the nucleotide sequence of SEQ ID NO: 1. Canine PD-1 sequences may differ by having, for example, conserved variations in non-conserved regions, but the canine PD-1 will have substantially the same biological function as the canine PD-1 comprising the amino acid sequence of SEQ ID NO: 2. For example, a biological function of PD-1 is to attenuate T-cell responses when bound to PD-L1 and/or PD-L2. That is, PD-1 may be considered a negative regulator. Notably, the cytoplasmic tail of PD-1 contains two tyrosine-based signaling motifs, an ITIM (immunoreceptor tyrosine-based inhibition motif) and an ITSM (immunoreceptor tyrosine-based switch motif). In addition, a biological function of canine PD-1 may be having, for example, an epitope in the extracellular domain that is specifically bound by an antibody of the instant disclosure.

Canine PD-L1 has been found to comprise the amino acid sequence of SEQ ID NO: 8. In a specific embodiment canine PD-L1 is encoded by a nucleotide sequence comprising SEQ ID NO: 7. Canine PD-L1 sequences may differ by having, for example, conserved variations in non-conserved regions, but the canine PD-L1 will have substantially the same biological function as the canine PD-L1 comprising the amino acid sequence of SEQ ID NO: 8. For example, one biological function of PD-L1 is to attenuate T-cell responses when bound to PD-1.

A particular canine PD-1 or PD-L1 amino acid sequence respectively, will generally be at least 90% identical to the canine PD-1 comprising the amino acid sequence of SEQ ID NO: 2, or canine PD-L1 comprising the amino acid sequence of SEQ ID NO: 8, respectively. In certain cases, a canine PD-1 or PD-L1 respectively, may be at least 95%, or even at least 96%, 97%, 98% or 99% identical to the canine PD-1 comprising the amino acid sequence of SEQ ID NO: 2, or the canine PD-L1 comprising the amino acid sequence of SEQ ID NO: 8, respectively. In certain embodiments, a canine PD-1 or a PD-L1 amino acid sequence will display no more than 10 amino acid differences from the canine PD-1 comprising the amino acid sequence of SEQ ID NO: 2, or the canine PD-L1 comprising the amino acid sequence of SEQ ID NO: 8, respectively. In certain embodiments, the canine PD-1 or the PD-L1 amino acid sequence respectively, may display no more than 5, or even no more than 4, 3, 2, or 1 amino acid difference from the canine PD-1 comprising the amino acid sequence of SEQ ID NO: 2, or the canine PD-L1 comprising the amino acid sequence of SEQ ID NO: 8, respectively. Percent identity can be determined as described herein below.

The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the mammalian body (e.g., canine body) of cancerous cells, cells or tissues infected with pathogens, or invading pathogens.

Caninized Anti-Human PD-1 Antibodies

The present invention provides isolated caninized murine anti-human PD-1 antibodies or antigen binding fragments thereof that bind canine PD-1 and uses of such antibodies or fragments.

As used herein, a caninized murine anti-human PD-1 antibody refers to a caninized antibody that specifically binds to mammalian PD-1. An antibody that specifically binds to mammalian PD-1, and in particular canine PD-1, is an antibody that exhibits preferential binding to mammalian PD-1 as compared to other antigens, but this specificity does not require absolute binding specificity. A caninized murine anti-human PD-1 antibody is considered "specific" for canine PD-1 if its binding is determinative of the presence of canine PD-1 in a biological sample obtained from a canine, or if it is capable of altering the activity of canine PD-1 without unduly interfering with the activity of other canine proteins in a canine sample, e.g. without producing undesired results such as false positives in a diagnostic context or side effects in a therapeutic context. The degree of specificity necessary for a caninized murine anti-human PD-1 antibody may depend on the intended use of the antibody, and at any rate is defined by its suitability for use for an intended purpose. The antibody, or binding compound derived from the antigen-binding site of an antibody, of the contemplated method binds to its antigen, or a variant or mutein thereof, with an affinity that is at least two-fold greater, preferably at least ten-times greater, more preferably at least 20-times greater, and most preferably at least 100-times greater than the affinity with any other canine antigen.

As used herein, an antibody is said to bind specifically to a polypeptide comprising a given sequence (in this case canine PD-1) if it binds to polypeptides comprising the sequence of canine PD-1, but does not bind to other canine proteins lacking the amino acid sequence of canine PD-1. For example, an antibody that specifically binds to a polypeptide comprising canine PD-1 may bind to a FLAG®-tagged form of canine PD-1, but will not bind to other FLAG®-tagged canine proteins.

As used herein, unless otherwise indicated, "antibody fragment" or "antigen binding fragment" refers to antigen binding fragments of antibodies, i.e. antibody fragments that retain the ability to bind specifically to the antigen (e.g., canine PD-1) bound by the full-length antibody, e.g. fragments that retain one or more CDR regions. Examples of antigen binding fragments include, but are not limited to, Fab, Fab', F(ab')$_2$, and Fv fragments; diabodies; linear antibodies; single-chain antibody molecules, e.g., sc-Fv; nanobodies and multispecific antibodies formed from antibody fragments.

Typically, a caninized antibody or antigen binding fragment thereof of the invention retains at least 10% of its canine PD-1 binding activity (when compared to the corresponding parental antibody) when that activity is expressed on a molar basis. Preferably, an antibody or antigen binding fragment of the invention retains at least 20%, 50%, 70%, 80%, 90%, 95% or 100% or more of the canine PD-1 binding affinity as the parental antibody. It is also intended that an antibody or antigen binding fragment of the invention can include conservative or non-conservative amino acid substitutions (referred to as "conservative variants" or "function conserved variants" of the antibody) that do not substantially alter its biologic activity.

"Isolated antibody" refers to the purification status and in such context means the molecule is substantially free of other biological molecules such as nucleic acids, proteins, lipids, carbohydrates, or other material such as cellular debris and growth media. Generally, the term "isolated" is not intended to refer to a complete absence of such material or to an absence of water, buffers, or salts, unless they are present in amounts that substantially interfere with experimental or therapeutic use of the binding compound as described herein.

The variable regions of each light/heavy chain pair form the antigen binding site of the antibody. Thus, in general, an intact antibody has two binding sites. Except in bifunctional or bispecific antibodies, the two binding sites are, in general, the same.

Typically, the variable domains of both the heavy and light chains comprise three hypervariable regions, also called complementarity determining regions (CDRs), located within relatively conserved framework regions (FR). The CDRs are usually flanked by the framework regions, enabling binding to a specific epitope. In general, from N-terminal to C-terminal, both light and heavy chains variable domains comprise FR1, CDR1, FR2, CDR2, FR3, CDR3 and FR4. The assignment of amino acids to each domain is, generally, in accordance with the definitions of *Sequences of Proteins of Immunological Interest*, Kabat, et al.; National Institutes of Health, Bethesda, Md.; 5$^{th}$ ed.; NIH Publ. No. 91-3242 (1991); Kabat, *Adv. Prot. Chem.* 32:1-75 (1978); Kabat, et al., *J. Biol. Chem.* 252:6609-6616 (1977); Chothia, et al., *J. Mol. Biol.* 196:901-917 (1987) or Chothia, et al., *Nature* 342:878-883 (1989)].

As used herein, the term "hypervariable region" refers to the amino acid residues of an antibody that are responsible for antigen-binding. The hypervariable region comprises amino acid residues from a "complementarity determining region" or "CDR" (i.e. CDRL1, CDRL2 and CDRL3 in the light chain variable domain and CDRH1, CDRH2 and CDRH3 in the heavy chain variable domain). [See Kabat et al. *Sequences of Proteins of Immunological Interest*, 5th Ed. Public Health Service, National Institutes of Health, Bethesda, Md. (1991), defining the CDR regions of an antibody by sequence; see also Chothia and Lesk, *J. Mol. Biol.* 196: 901-917 (1987) defining the CDR regions of an antibody by structure]. As used herein, the term "framework" or "FR" residues refers to those variable domain residues other than the hypervariable region residues defined herein as CDR residues.

As used herein, the term "canine" includes all domestic dogs, *Canis lupus familiaris* or *Canis familiaris*, unless otherwise indicated.

As used herein the term "canine frame" refers to the amino acid sequence of the heavy chain and light chain of a canine antibody other than the hypervariable region residues defined herein as CDR residues. With regard to a caninized antibody, in the majority of embodiments the amino acid sequences of the native canine CDRs are replaced with the corresponding foreign CDRs (e.g., those from a mouse antibody) in both chains. Optionally the heavy and/or light chains of the canine antibody may contain some foreign non-CDR residues, e.g., so as to preserve the conformation of the foreign CDRs within the canine antibody, and/or to modify the Fc function, as discussed below.

There are four known IgG heavy chain subtypes of dog IgG and they are referred to as IgG-A, IgG-B, IgG-C, and IgG-D. The two known light chain subtypes are referred to as lambda and kappa.

Besides binding and activating of canine immune cells, a canine or caninized antibody against PD-1 optimally has two attributes:

1. Lack of effector functions such as antibody-dependent cytotoxicity (ADCC) and complement-dependent cytotoxicity (CDC), and
2. be readily purified on a large scale using industry standard technologies such as that based on protein A chromatography.

None of the naturally occurring canine IgG isotypes satisfy both criteria. For example, IgG-B can be purified using protein A, but has high level of ADCC activity. On the other hand, IgG-A binds weakly to protein A, but displays undesirable ADCC activity. Moreover, neither IgG-C nor IgG-D can be purified on protein A columns, although IgG-D display no ADCC activity. (IgG-C has considerable ADCC activity). The present invention overcomes this difficulty by providing mutant canine IgG-B antibodies specific to PD-1; such antibodies lack effector functions such as ADCC and can be easily of purified using industry standard protein A chromatography.

As used herein, the term "caninized antibody" refers to an antibody that comprises the three heavy chain CDRs and the three light chain CDRS from a murine anti-human PD-1 antibody together with a canine frame or a modified canine frame. A modified canine frame comprises one or more amino acids changes as exemplified herein that further optimize the effectiveness of the caninized antibody, e.g., to increase its binding to canine PD-1 and/or its ability to block the binding of canine PD-1 to canine PD-L1.

"Homology" refers to sequence similarity between two polynucleotide sequences or between two polypeptide sequences when they are optimally aligned. When a position in both of the two compared sequences is occupied by the same base or amino acid monomer subunit, e.g., if a position in each of two DNA molecules is occupied by adenine, then the molecules are homologous at that position. The percent of homology is the number of homologous positions shared by the two sequences divided by the total number of positions compared×100. For example, if 6 of 10 of the positions in two sequences are matched or homologous when the sequences are optimally aligned then the two sequences are 60% homologous. Generally, the comparison is made when two sequences are aligned to give maximum percent homology.

"Isolated nucleic acid molecule" means a DNA or RNA of genomic, mRNA, cDNA, or synthetic origin or some combination thereof which is not associated with all or a portion of a polynucleotide in which the isolated polynucleotide is found in nature, or is linked to a polynucleotide to which it is not linked in nature. For purposes of this disclosure, it should be understood that "a nucleic acid molecule comprising" a particular nucleotide sequence does not encompass intact chromosomes. Isolated nucleic acid molecules "comprising" specified nucleic acid sequences may include, in addition to the specified sequences, coding sequences for up to ten or even up to twenty or more other proteins or portions or fragments thereof, or may include operably linked regulatory sequences that control expression of the coding region of the recited nucleic acid sequences, and/or may include vector sequences.

The phrase "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to use promoters, polyadenylation signals, and enhancers.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice. It should also be readily understood that when a nucleic acid sequence is provided herein, it may include a stop codon. However, as stop codons are interchangeable the inclusion of a specific stop codon in a sequence should not be viewed as a necessary portion of that sequence.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that not all progeny will have precisely identical DNA content, due to deliberate or inadvertent mutations. Mutant progeny that have the same function or biological activity as screened for in the originally transformed cell are included. Where distinct designations are intended, it will be clear from the context.

As used herein, "germline sequence" refers to a sequence of unrearranged immunoglobulin DNA sequences. Any suitable source of unrearranged immunoglobulin sequences may be used. Human germline sequences may be obtained, for example, from JOINSOLVER® germline databases on the website for the National Institute of Arthritis and Musculoskeletal and Skin Diseases of the United States National Institutes of Health. Mouse germline sequences may be obtained, for example, as described in Giudicelli et al. [*Nucleic Acids Res.* 33:D256-D261 (2005)].

Properties of the Exemplary Caninized Murine Anti-Human PD-1 Antibodies

The present invention provides isolated caninized murine anti-human PD-1 antibodies and methods of use of the antibodies or antigen binding fragments thereof in the treatment of disease e.g., the treatment of cancer in canines. Examples of caninized murine anti-human PD-1 antibodies that bind canine PD-1 include, but are not limited to: antibodies that comprise canine IgG-A, IgG-B, and IgG-D heavy chains and/or canine kappa light chains together with murine anti-human PD-1 CDRs. Accordingly, the present invention provides isolated caninized murine anti-human PD-1 antibodies or antigen binding fragments thereof that bind to canine PD-1 and block the binding of canine PD-1 to canine PD-L1.

The isolated antibody or antigen binding fragment thereof that binds canine PD-1 can comprise one, two, three, four, five, or six of the complementarity determining regions (CDRs) of the murine anti-human antibody as described herein. The one, two, three, four, five, or six CDRs may be independently selected from the CDR sequences of those provided in Table 2 in the Examples below. In certain embodiments, one, two or three CDRs are selected from the $V_L$ CDRs (amino acid SEQ ID NOs: 20, 22, and/or 24) and/or one, two or three CDRs selected from the $V_H$ CDRs (SEQ ID NOs: 14, 16, and/or 18), and/or conservatively modified variants of the one, two or three of these $V_L$ CDRs and/or conservatively modified variants of the one, two or three of these $V_H$ CDRs.

In a further embodiment, the isolated antibody or antigen-binding fragment thereof that binds canine PD-1 comprises a canine antibody kappa light chain comprising a murine light chain CDR-1, CDR-2 and/or CDR-3 and a canine antibody heavy chain IgG comprising a murine heavy chain CDR-1, CDR-2 and/or CDR-3.

In other embodiments, the invention provides antibodies or antigen binding fragments thereof that specifically binds PD-1 and have canine antibody kappa light chains comprising CDRs comprising at least 80%, 85%, 90%, 95%, 98% or 99% sequence identity with SEQ ID NOs: 20, 22, and/or 24 and canine antibody heavy chain IgG with CDRs comprising at least 80%, 85%, 90%, 95%, 98% or 99% sequence identity with SEQ ID NOs: 14, 16, and/or 18, while still exhibiting the desired binding and functional properties. In another embodiment the antibody or antigen binding fragment of the present invention comprises a canine frame comprising of a combination of IgG heavy chain sequence (comprising an amino acid sequence of SEQ ID NO: 26, 28, or 30 with and without signal sequence) with a kappa light chain (comprising an amino acid sequence of SEQ ID NO: 32, or 34 with and without signal sequence) having up to 0, 1, 2, 3, 4, 5, 6, 7, 8, 9, 10 or more conservative or non-conservative amino acid substitutions, while still exhibiting the desired binding and functional properties. In a particular embodiment of this type, the number of conservative amino acid substitutions is between 0 to 5 for the IgG heavy chain and 0 to 5 for the kappa light chain.

"Conservatively modified variants" or "conservative substitution" refers to substitutions of amino acids in a protein with other amino acids having similar characteristics (e.g. charge, side-chain size, hydrophobicity/hydrophilicity, backbone conformation and rigidity, etc.), such that the changes can frequently be made without altering the biological activity of the protein. Those of skill in this art recognize that, in general, single amino acid substitutions in non-essential regions of a polypeptide do not substantially alter biological activity [see, e.g., Watson et al., *Molecular Biology of the Gene*, The Benjamin/Cummings Pub. Co., p. 224 (4th Ed.; 1987)]. In addition, substitutions of structurally or functionally similar amino acids are less likely to disrupt biological activity. Various embodiments of the antibody or antigen binding fragment of the present invention comprise polypeptide chains with the sequences disclosed herein, e.g., SEQ ID NOs: 26, 28, 30, 32, and/or 34, or polypeptide chains comprising up to 1, 2, 3, 4, 5, 6, 7, 8, 9, 10, 12, 15, 20 or more conservative amino acid substitutions. Exemplary conservative substitutions are set forth in Table I.

TABLE I

Exemplary Conservative Amino Acid Substitutions

| Original residue | Conservative substitution |
|---|---|
| Ala (A) | Gly; Ser; |
| Arg (R) | Lys; His |

TABLE I-continued

Exemplary Conservative Amino Acid Substitutions

| Original residue | Conservative substitution |
|---|---|
| Asn (N) | Gln; His |
| Asp (D) | Glu; Asn |
| Cys (C) | Ser; Ala |
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala |
| Ser (S) | Thr |
| Thr (T) | Ser |
| Trp (W) | Tyr; Phe |
| Tyr (Y) | Trp; Phe |
| Val (V) | Ile; Leu |

Function-conservative variants of the antibodies of the invention are also contemplated by the present invention. "Function-conservative variants," as used herein, refers to antibodies or fragments in which one or more amino acid residues have been changed without altering a desired property, such an antigen affinity and/or specificity. Such variants include, but are not limited to, replacement of an amino acid with one having similar properties, such as the conservative amino acid substitutions of Table I.

Nucleic Acids

The present invention further comprises the nucleic acids encoding the immunoglobulin chains of caninized murine anti-human PD-1 antibodies and antigen binding fragments thereof disclosed herein. For example, the present invention includes the nucleic acids listed in Tables 2 and 3 and the Sequence Listing Table below.

Also included in the present invention are nucleic acids that encode immunoglobulin polypeptides comprising amino acid sequences that are at least about 70% identical, preferably at least about 80% identical, more preferably at least about 90% identical and most preferably at least about 95% identical (e.g., 95%, 96%, 97%, 98%, 99%, 100%) to the amino acid sequences of the antibodies provided herein when the comparison is performed by a BLAST algorithm wherein the parameters of the algorithm are selected to give the largest match between the respective sequences over the entire length of the respective reference sequences. The present invention further provides nucleic acids that encode immunoglobulin polypeptides comprising amino acid sequences that are at least about 70% similar, preferably at least about 80% similar, more preferably at least about 90% similar and most preferably at least about 95% similar (e.g., 95%, 96%, 97%, 98%, 99%, 100%) to any of the reference amino acid sequences when the comparison is performed with a BLAST algorithm, wherein the parameters of the algorithm are selected to give the largest match between the respective sequences over the entire length of the respective reference sequences, are also included in the present invention.

Sequence identity refers to the degree to which the amino acids of two polypeptides are the same at equivalent positions when the two sequences are optimally aligned. Sequence similarity includes identical residues and nonidentical, biochemically related amino acids. Biochemically related amino acids that share similar properties and may be interchangeable are discussed above.

The following references relate to BLAST algorithms often used for sequence analysis: BLAST ALGORITHMS: Altschul, S. F., et al., *J. Mol. Biol.* 215:403-410 (1990); Gish, W., et al., *Nature Genet.* 3:266-272 (1993); Madden, T. L., et al., *Meth. Enzymol.* 266:131-141 (1996); Altschul, S. F., et al., *Nucleic Acids Res.* 25:3389-3402 (1997); Zhang, J., et al., *Genome Res.* 7:649-656 (1997); Wootton, J. C., et al., *Comput. Chem.* 17:149-163 (1993); Hancock, J. M. et al., *Comput. Appl. Biosci.* 10:67-70 (1994); ALIGNMENT SCORING SYSTEMS: Dayhoff, M. O., et al., "A model of evolutionary change in proteins." in *Atlas of Protein Sequence and Structure*, vol. 5, suppl. 3. M. O. Dayhoff (ed.), pp. 345-352, (1978); *Natl. Biomed. Res. Found.*, Washington, D.C.; Schwartz, R. M., et al., "Matrices for detecting distant relationships." in Atlas of Protein Sequence and Structure, vol. 5, suppl. 3." (1978), M. O. Dayhoff (ed.), pp. 353-358 (1978), *Natl. Biomed. Res. Found., Washington, D.C.; Altschul, S. F., J. Mol. Biol.* 219:555-565 (1991); States, D. J., et al., *Methods* 3:66-70 (1991); Henikoff, S., et al., *Proc. Natl. Acad. Sci. USA* 89:10915-10919 (1992); Altschul, S. F., et al., *J. Mol. Evol.* 36:290-300 (1993); ALIGNMENT STATISTICS: Karlin, S., et al., *Proc. Natl. Acad. Sci. USA* 87:2264-2268 (1990); Karlin, S., et al., *Proc. Natl. Acad. Sci. USA* 90:5873-5877 (1993); Dembo, A., et al., *Ann. Prob.* 22:2022-2039 (1994); and Altschul, S. F. "Evaluating the statistical significance of multiple distinct local alignments." in *Theoretical and Computational Methods in Genome Research* (S. Suhai, ed.), pp. 1-14, Plenum, New York (1997).

This present invention also provides expression vectors comprising the isolated nucleic acids of the invention, wherein the nucleic acid is operably linked to control sequences that are recognized by a host cell when the host cell is transfected with the vector. Also provided are host cells comprising an expression vector of the present invention and methods for producing the antibody or antigen binding fragment thereof disclosed herein comprising culturing a host cell harboring an expression vector encoding the antibody or antigen binding fragment in culture medium, and isolating the antigen or antigen binding fragment thereof from the host cell or culture medium.

Epitope Binding and Binding Affinity

The present invention further provides antibodies or antigen binding fragments thereof that bind to the same epitope on canine PD-1 as the caninized murine anti-human PD-1 antibody comprising the amino acid sequence of SEQ ID NO: 28 and/or of SEQ ID NO: 32, or the caninized murine anti-human PD-1 antibody comprising the amino acid sequence of SEQ ID NO: 28 and/or of SEQ ID NO: 34. The caninized murine anti-human PD-1 antibodies or antigen binding fragments thereof are capable of inhibiting the binding of canine PD-1 to canine PD-L1.

The caninized murine anti-human PD-1 antibody can be produced recombinantly as described below in the examples. Mammalian cell lines available as hosts for expression of the antibodies or fragments disclosed herein are well known in the art and include many immortalized cell lines available from the American Type Culture Collection (ATCC). These include, inter alia, Chinese hamster ovary (CHO) cells, NSO, SP2 cells, HeLa cells, baby hamster kidney (BHK) cells, monkey kidney cells (COS), human hepatocellular carcinoma cells (e.g., Hep G2), A549 cells, 3T3 cells, HEK-293 cells and a number of other cell lines. Mammalian host cells include human, mouse, rat, dog, monkey, pig, goat, bovine, horse and hamster cells. Cell lines of particular preference are selected through determining which cell lines have high expression levels. Other cell lines that may be used are insect cell lines, such as Sf9 cells, amphibian cells, bacterial cells, plant cells and fungal cells. When recombinant expression vectors encoding the heavy chain or antigen-binding portion or fragment thereof, the light chain and/or antigen-binding fragment thereof are introduced into mammalian host cells, the antibodies are produced by culturing the host cells for a period of time sufficient to allow for expression of the antibody in the host cells or, more preferably, secretion of the antibody into the culture medium in which the host cells are grown.

Antibodies can be recovered from the culture medium using standard protein purification methods. Further, expression of antibodies of the invention (or other moieties therefrom) from production cell lines can be enhanced using a number of known techniques. For example, the glutamine synthetase gene expression system (the GS system) is a common approach for enhancing expression under certain conditions. The GS system is discussed in whole or part in connection with European Patent Nos. 0 216 846, 0 256 055, and 0 323 997 and European Patent Application No. 89303964.4.

In general, glycoproteins produced in a particular cell line or transgenic animal will have a glycosylation pattern that is characteristic for glycoproteins produced in the cell line or transgenic animal. Therefore, the particular glycosylation pattern of an antibody will depend on the particular cell line or transgenic animal used to produce the antibody. However, all antibodies encoded by the nucleic acid molecules provided herein, or comprising the amino acid sequences provided herein, comprise the instant invention, independent of the glycosylation pattern that the antibodies may have. Similarly, in particular embodiments, antibodies with a glycosylation pattern comprising only non-fucosylated N-glycans may be advantageous, because these antibodies have been shown to typically exhibit more potent efficacy than their fucosylated counterparts both in vitro and in vivo [See for example, Shinkawa et al., *J. Biol. Chem.* 278: 3466-3473 (2003); U.S. Pat. Nos. 6,946,292 and 7,214,775].

The present invention further includes antibody fragments of the caninized murine anti-human PD-1 antibodies disclosed herein. The antibody fragments include F(ab)$_2$ fragments, which may be produced by enzymatic cleavage of an IgG by, for example, pepsin. Fab fragments may be produced by, for example, reduction of F(ab)$_2$ with dithiothreitol or mercaptoethylamine. A Fab fragment is a $V_L$—$C_L$ chain appended to a $V_H$-$C_{H1}$ chain by a disulfide bridge. A F(ab)$_2$ fragment is two Fab fragments which, in turn, are appended by two disulfide bridges. The Fab portion of an F(ab)$_2$ molecule includes a portion of the $F_c$ region between which disulfide bridges are located. An $F_v$ fragment is a $V_L$ or $V_H$ region.

In one embodiment, the antibody or antigen binding fragment comprises a heavy chain constant region, e.g., a canine constant region, such as IgG-A, IgG-B, IgG-C and IgG-D canine heavy chain constant region or a variant thereof. In another embodiment, the antibody or antigen binding fragment comprises a light chain constant region, e.g., a canine light chain constant region, such as lambda or kappa canine light chain region or variant thereof. By way of example, and not limitation the canine heavy chain constant region can be from IgG-D and the canine light chain constant region can be from kappa.

Antibody Engineering

The caninized murine anti-human PD-1 antibodies of the present invention have been engineered to include modifications to framework residues within the variable domains of a parental (i.e., canine) monoclonal antibody, e.g. to improve the properties of the antibody.

Experimental and Diagnostic Uses

Caninized murine anti-human PD-1 antibodies or antigen-binding fragments thereof of the present invention may also be useful in diagnostic assays for canine PD-1 protein, e.g., detecting its expression in specific tumor cells, tissues, or serum. Such diagnostic methods may be useful in various disease diagnoses, particularly certain cancers in canines.

For example, such a method comprises the following steps:
  (a) coat a substrate (e.g., surface of a microtiter plate well, e.g., a plastic plate) with caninized murine anti-human PD-1 antibody or an antigen-binding fragment thereof;
  (b) apply a sample to be tested for the presence of canine PD-1 to the substrate;
  (c) wash the plate, so that unbound material in the sample is removed;
  (d) apply detectably labeled antibodies (e.g., enzyme-linked antibodies) which are also specific to the PD-1 antigen;
  (e) wash the substrate, so that the unbound, labeled antibodies are removed;
  (f) if the labeled antibodies are enzyme linked, apply a chemical which is converted by the enzyme into a fluorescent signal; and
  (g) detect the presence of the labeled antibody.

In a further embodiment, the labeled antibody is labeled with peroxidase which react with ABTS [e.g., 2,2'-azino-bis (3-ethylbenzthiazoline-6-sulphonic acid)] or 3,3',5,5'-Tetramethylbenzidine to produce a color change which is detectable. Alternatively, the labeled antibody is labeled with a detectable radioisotope (e.g., $^3$H) which can be detected by scintillation counter in the presence of a scintillant. Caninized murine anti-human PD-1 antibodies of the invention may be used in a Western blot or immuno protein blot procedure. Such a procedure forms part of the present invention and includes for example:
  (i) contacting a membrane or other solid substrate to be tested for the presence of bound canine PD-1 or a fragment thereof with a caninized murine anti-human PD-1 antibody or antigen-binding fragment thereof of the present invention. Such a membrane may take the form of a nitrocellulose or vinyl-based [e.g., polyvinylidene fluoride (PVDF)] membrane to which the proteins to be tested for the presence of canine PD-1 in a non-denaturing PAGE (polyacrylamide gel electrophoresis) gel or SDS-PAGE (sodium dodecyl sulfate polyacrylamide gel electrophoresis) gel have been transferred (e.g., following electrophoretic separation in the gel). Before contact of membrane with the caninized murine anti-human PD-1 antibody or antigen-binding fragment thereof, the membrane is optionally blocked, e.g., with non-fat dry milk or the like so as to bind non-specific protein binding sites on the membrane.
  (ii) washing the membrane one or more times to remove unbound caninized murine anti-human PD-1 antibody or an antigen-binding fragment thereof and other unbound substances; and
  (iii) detecting the bound caninized murine anti-human PD-1 antibody or antigen-binding fragment thereof.

Detection of the bound antibody or antigen-binding fragment may be by binding the antibody or antigen-binding fragment with a secondary antibody (an anti-immunoglobulin antibody) which is detectably labeled and, then, detecting the presence of the secondary antibody.

The caninized murine anti-human PD-1 antibodies and antigen-binding fragments thereof disclosed herein may also be used for immunohistochemistry. Such a method forms part of the present invention and comprises, e.g., (1) contacting a cell to be tested for the presence of canine PD-1 with a caninized murine anti-human PD-1 antibody or antigen-binding fragment thereof of the present invention; and (2) detecting the antibody or fragment on or in the cell. If the antibody or antigen-binding fragment itself is detectably labeled, it can be detected directly. Alternatively, the antibody or antigen-binding fragment may be bound by a detectably labeled secondary antibody which is detected.

Certain caninized murine anti-human PD-1 antibodies and antigen-binding fragments thereof disclosed herein may also be used for in vivo tumor imaging. Such a method may include injection of a radiolabeled caninized murine anti-human PD-1 antibodies or antigen-binding fragment thereof into the body of a canine to be tested for the presence of a tumor associated with canine PD-1 expression followed by nuclear imaging of the body of the patient to detect the presence of the labeled antibody or antigen-binding fragment e.g., at loci comprising a high concentration of the antibody or antigen-binding fragment which are bound to the tumor.

Imaging techniques include SPECT imaging (single photon emission computed tomography) or PET imaging (positron emission tomography). Labels include e.g., iodine-123 ($^{123}$I) and technetium-99m ($^{99m}$Tc), e.g., in conjunction with SPECT imaging or $^{11}$C, $^{13}$N, $^{15}$O or $^{18}$F, e.g., in conjunction with PET imaging or Indium-111 [See e.g., Gordon et al., *International Rev. Neurobiol.* 67:385-440 (2005)].

Pharmaceutical Compositions and Administration

To prepare pharmaceutical or sterile compositions of the caninized murine anti-human PD-1 antibody or antigen binding fragment thereof is admixed with a pharmaceutically acceptable carrier or excipient. [See, e.g., *Remington's Pharmaceutical Sciences* and *U.S. Pharmacopeia: National Formulary*, Mack Publishing Company, Easton, Pa. (1984)].

Formulations of therapeutic and diagnostic agents may be prepared by mixing with acceptable carriers, excipients, or stabilizers in the form of, e.g., lyophilized powders, slurries, aqueous solutions or suspensions [see, e.g., Hardman, et al. (2001) *Goodman and Gilman's The Pharmacological Basis of Therapeutics*, McGraw-Hill, New York, N.Y.; Gennaro (2000) *Remington: The Science and Practice of Pharmacy*, Lippincott, Williams, and Wilkins, New York, N.Y.; Avis, et al. (eds.) (1993) *Pharmaceutical Dosage Forms: Parenteral Medications*, Marcel Dekker, NY; Lieberman, et al. (eds.) (1990) *Pharmaceutical Dosage Forms: Tablets*, Marcel Dekker, NY; Lieberman, et al. (eds.) (1990) *Pharmaceutical Dosage Forms: Disperse Systems*, Marcel Dekker, NY; Weiner and Kotkoskie (2000) *Excipient Toxicity and Safety*, Marcel Dekker, Inc., New York, N.Y.]. In one embodiment, anti-PD-1 antibodies of the present invention are diluted to an appropriate concentration in a sodium acetate solution pH 5-6, and NaCl or sucrose is added for tonicity. Additional agents, such as polysorbate 20 or polysorbate 80, may be added to enhance stability.

Toxicity and therapeutic efficacy of the antibody compositions, administered alone or in combination with another agent, can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index ($LD_{50}/ED_{50}$). In particular aspects, antibodies exhibiting high therapeutic indices are desirable. The data obtained from these cell culture assays and animal studies can be used in formulating a range of dosage for use in canines. The dosage of such compounds lies preferably within a range of circulating concentrations that include the $ED_{50}$ with little or no toxicity. The dosage may vary within this range depending upon the dosage form employed and the route of administration.

The mode of administration can vary. Suitable routes of administration include oral, rectal, transmucosal, intestinal, parenteral; intramuscular, subcutaneous, intradermal, intramedullary, intrathecal, direct intraventricular, intravenous, intraperitoneal, intranasal, intraocular, inhalation, insufflation, topical, cutaneous, transdermal, or intra-arterial.

In particular embodiments, the caninized murine anti-human PD-1 antibody or antigen binding fragment thereof can be administered by an invasive route such as by injection. In further embodiments of the invention, a caninized murine anti-human PD-1 antibody or antigen binding fragment thereof, or pharmaceutical composition thereof, is administered intravenously, subcutaneously, intramuscularly, intraarterially, intratumorally, or by inhalation, aerosol delivery. Administration by non-invasive routes (e.g., orally; for example, in a pill, capsule or tablet) is also within the scope of the present invention.

Compositions can be administered with medical devices known in the art. For example, a pharmaceutical composition of the invention can be administered by injection with a hypodermic needle, including, e.g., a prefilled syringe or autoinjector. The pharmaceutical compositions disclosed herein may also be administered with a needleless hypodermic injection device; such as the devices disclosed in U.S. Pat. Nos. 6,620,135; 6,096,002; 5,399,163; 5,383,851; 5,312,335; 5,064,413; 4,941,880; 4,790,824 or 4,596,556.

The pharmaceutical compositions disclosed herein may also be administered by infusion. Examples of well-known implants and modules form administering pharmaceutical compositions include: U.S. Pat. No. 4,487,603, which discloses an implantable micro-infusion pump for dispensing medication at a controlled rate; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments. Many other such implants, delivery systems, and modules are well known to those skilled in the art.

Alternately, one may administer the caninized murine anti-human PD-1 antibody in a local rather than systemic manner, for example, via injection of the antibody directly into an arthritic joint or pathogen-induced lesion characterized by immunopathology, often in a depot or sustained release formulation. Furthermore, one may administer the caninized murine anti-human PD-1 antibody in a targeted drug delivery system, for example, in a liposome coated with a tissue-specific antibody, targeting, for example, arthritic joint or pathogen-induced lesion characterized by immunopathology. The liposomes will be targeted to and taken up selectively by the afflicted tissue.

The administration regimen depends on several factors, including the serum or tissue turnover rate of the therapeutic antibody, the level of symptoms, the immunogenicity of the therapeutic antibody, and the accessibility of the target cells in the biological matrix. Preferably, the administration regimen delivers sufficient therapeutic antibody to effect improvement in the target disease state, while simultaneously minimizing undesired side effects. Accordingly, the amount of biologic delivered depends in part on the particular therapeutic antibody and the severity of the condition being treated. Guidance in selecting appropriate doses of therapeutic antibodies is available [see, e.g., Wawrzynczak *Antibody Therapy*, Bios Scientific Pub. Ltd, Oxfordshire, U K (1996); Kresina (ed.) *Monoclonal Antibodies, Cytokines and Arthritis,* Marcel Dekker, New York, N.Y. (1991); Bach (ed.) *Monoclonal Antibodies and Peptide Therapy in Autoimmune Diseases*, Marcel Dekker, New York, N.Y. (1993); Baert, et al. *New Engl. J. Med.* 348:601-608 (2003); Milgrom et al. *New Engl. J. Med.* 341:1966-1973 (1999); Slamon et al. *New Engl. J. Med.* 344:783-792 (2001); Beniaminovitz et al. *New Engl. J. Med.* 342:613-619 (2000); Ghosh et al. *New Engl. J. Med.* 348:24-32 (2003); Lipsky et al. *New Engl. J. Med.* 343:1594-1602 (2000)].

Determination of the appropriate dose is made by the veterinarian, e.g., using parameters or factors known or suspected in the art to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced.

Antibodies or antigen binding fragments thereof disclosed herein may be provided by continuous infusion, or by doses administered, e.g., daily, 1-7 times per week, weekly, biweekly, monthly, bimonthly, quarterly, semiannually, annually etc. Doses may be provided, e.g., intravenously, subcutaneously, topically, orally, nasally, rectally, intramuscular, intracerebrally, intraspinally, or by inhalation. A total weekly dose is generally at least 0.05 µg/kg body weight, more generally at least 0.2 µg/kg, 0.5 µg/kg, 1 µg/kg, 10 µg/kg, 100 µg/kg, 0.25 mg/kg, 1.0 mg/kg, 2.0 mg/kg, 5.0 mg/ml, 10 mg/kg, 25 mg/kg, 50 mg/kg or more [see, e.g., Yang, et al. *New Engl. J. Med.* 349:427-434 (2003); Herold, et al. *New Engl. J. Med.* 346:1692-1698 (2002); Liu, et al. *J. Neurol. Neurosurg. Psych.* 67:451-456 (1999); Portielji, et al. *Cancer Immunol. Immunother.* 52:133-144 (2003)]. Doses may also be provided to achieve a pre-determined target concentration of the caninized murine anti-human PD-1 antibody in the subject's serum, such as 0.1, 0.3, 1, 3, 10, 30, 100, 300 µg/ml or more. In other embodiments, a caninized murine anti-human PD-1 antibody of the present invention is administered subcutaneously or intravenously, on a weekly, biweekly, "every 4 weeks," monthly, bimonthly, or quarterly basis at 10, 20, 50, 80, 100, 200, 500, 1000 or 2500 mg/subject.

As used herein, "inhibit" or "treat" or "treatment" includes a postponement of development of the symptoms associated with a disorder and/or a reduction in the severity of the symptoms of such disorder. The terms further include ameliorating existing uncontrolled or unwanted symptoms, preventing additional symptoms, and ameliorating or preventing the underlying causes of such symptoms. Thus, the terms denote that a beneficial result has been conferred on a vertebrate subject with a disorder, disease or symptom, or with the potential to develop such a disorder, disease or symptom.

As used herein, the terms "therapeutically effective amount", "therapeutically effective dose" and "effective amount" refer to an amount of the caninized murine anti-human PD-1 antibody or antigen binding fragment thereof of the present invention that, when administered alone or in combination with an additional therapeutic agent to a cell, tissue, or subject, is effective to cause a measurable improvement in one or more symptoms of a disease or condition or the progression of such disease or condition. A therapeutically effective dose further refers to that amount of the binding compound sufficient to result in at least partial amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously. An effective amount of a therapeutic will result in an improvement of a diagnostic measure or parameter by at least 10%; usually by at least 20%; preferably at least about 30%; more preferably at least 40%, and most preferably by at least 50%. An effective amount can also result in an improvement in a subjective measure in cases where subjective measures are used to assess disease severity.

Other Combination Therapies

As previously described, the caninized murine anti-human PD-1 antibody or antigen binding fragment thereof may be coadministered with one or other more therapeutic agents (such as a chemotherapeutic agent). The antibody may be linked to the agent (as an immunocomplex) or can be administered separately from the agent. In the latter case (separate administration), the antibody can be administered before, after or concurrently with the agent or can be coadministered with other known therapies.

Kits

Further provided are kits comprising one or more components that include, but are not limited to, an antibody or antigen binding fragment, as discussed herein, which specifically binds PD-1 (e.g., a caninized murine anti-human PD-1 antibody or antigen binding fragment thereof of the present invention) in association with one or more additional components including, but not limited to a pharmaceutically acceptable carrier and/or a chemotherapeutic agent, as discussed herein. The binding composition and/or the chemotherapeutic agent can be formulated as a pure composition or in combination with a pharmaceutically acceptable carrier, in a pharmaceutical composition.

In one embodiment, the kit includes a binding composition of the invention (the caninized murine anti-human PD-1 antibody comprising the amino acid sequence of SEQ ID NO: 28 and of SEQ ID NO: 32 or 34, or a pharmaceutical composition thereof in one container (e.g., in a sterile glass or plastic vial) and a pharmaceutical composition thereof and/or a chemotherapeutic agent in another container (e.g., in a sterile glass or plastic vial).

In another embodiment, the kit comprises a combination of the invention, including a binding composition component (e.g., the caninized murine anti-human PD-1 antibody comprising the amino acid sequence of SEQ ID NO: 28 and of SEQ ID NO: 32 or 34) along with a pharmaceutically acceptable carrier, optionally in combination with one or more therapeutic agent component formulated together, optionally, in a pharmaceutical composition, in a single, common container.

If the kit includes a pharmaceutical composition for parenteral administration to a subject, the kit can include a device for performing such administration. For example, the kit can include one or more hypodermic needles or other injection devices as discussed above. The kit can also include a package insert including information concerning the pharmaceutical compositions and dosage forms in the kit. Generally, such information aids pet owners and veterinarians in using the enclosed pharmaceutical compositions and dosage forms effectively and safely. For example, the following information regarding a combination of the invention may be supplied in the insert: pharmacokinetics, pharmacodynamics, clinical studies, efficacy parameters, indications and usage, contraindications, warnings, precautions, adverse reactions, overdosage, proper dosage and administration, how supplied, proper storage conditions, references, manufacturer/distributor information and patent information.

As a matter of convenience, an antibody or specific binding agent disclosed herein can be provided in a kit, i.e., a packaged combination of reagents in predetermined amounts with instructions for performing the diagnostic or detection assay. Where the antibody is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

EXAMPLES

Example 1

Canine PD-1 and PD-L1

Identification and Cloning of Canine PD-1:

A nucleic acid encoding a full length canine PD-1 (cPD-1) was identified through a search of the NCBI gene bank data bases (accession number XM_543338.4, SEQ ID NO: 1). The translated amino acid sequence SEQ ID NO: 2 (accession number XP-543338.3) corresponds to putative canine PD-1 protein which was further identified through searching the gene bank (NCBI) protein databases and aligning the identified amino acid sequence with murine, feline, and human PD-1 amino acid sequences. The DNA sequence corresponding to the full length canine PD-1 gene that was codon optimized for CHO cells was synthesized and cloned into a plasmid designated p96793. Comparison of DNA and protein sequences of predicted canine PD-1 with known PD-1 DNA and protein sequences led to the identification of the DNA sequences encoding the extra-cellular domain (ECD) of canine PD-1 (SEQ ID NO: 3) and the amino acid sequence of the ECD of canine PD-1 (SEQ ID NO: 4).

A DNA sequence encoding the ECD of canine PD-1 in addition to a GT linker and 8 histidine residues was synthesized and cloned into a plasmid designated LPD2726. A nucleic acid sequence (SEQ ID NO: 5) corresponding to the canine PD-1 ECD plus a GT linker and the Fc part of human IgG1 Fc gene was chemically synthesized and cloned into a plasmid designated LPD2727. Canine PD-1 ECD and the Fc part of human IgG1 Fc comprises the amino acid sequence of SEQ ID NO: 6.

Identification and Cloning of Canine PD-L1:

A nucleic acid encoding a full length canine PD-L1 was identified through a search of the NCBI gene bank data bases (accession number XM_541302.4; SEQ ID NO: 7). The translated amino acid sequence (accession number XP-541302.4; SEQ ID NO: 8) corresponding to the putative canine PD-L1 protein was identified by searching the gene bank (NCBI) protein databases and alignment of the identified sequence with known PD-L1 mouse and human sequences.

Comparison of DNA encoding canine PD-L1 with known PD-L1 sequences identified the DNA sequence corresponding to the ECD domain of canine PD-L1 (SEQ ID NO: 9; which was codon optimized for CHO cells). The predicted amino acid sequence of the ECD of canine PD-L1 is SEQ ID NO: 10. DNA encoding PD-L1 ECD plus GT linker and 8 histidine residues was synthesized and cloned into a plasmid designated LPD2695.

A DNA sequence encoding the amino acid sequence of canine PD-L1 ECD plus GT linker and the Fc part of human IgG1 Fc (SEQ ID NO: 11) was chemically synthesized and cloned into a plasmid designated LPD2697. Canine PD-L1 ECD plus GT linker and the Fc part of human IgG1 comprises the amino acid sequence of SEQ ID NO: 12. Table 1 contains a description of the expression plasmids mentioned above.

TABLE 1

PLASMIDS COMPRISING DNA ENCODING PD-1 or PD-L1

| PLASMID NAME | EXPRESSED GENE |
|---|---|
| P96793 | Canine PD-1 |
| LPD2726 | Canine PD-1 ECD-8HIS |
| LPD2727 | Canine PD-1 ECD-/Human IgG1 Fc |
| LPD2695 | Canine PD-L1 ECD-8HIS |
| LPD2697 | Canine PD-L1 ECD-/Human IgG1 Fc |

Expression of PD-1 and PD-L1 Proteins:

Expression plasmids encoding the PD-1ECD-HIS, PD-1ECD-Fc, PDL-1 ECD-HIS, and PD-L1ECD-Fc proteins were transfected into HEK 293 cells and the proteins were purified from the supernatant of transfected cells using Protein A for Fc fusion proteins or Nickel ($Ni^{2+}$) column chromatography for HIS-tagged proteins. Purified proteins were used for: ELISA or binding assays as detailed below. Expressed proteins were analyzed by SDS-PAGE gels.

Example 2

Identification of Murine Anti-Human Monoclonal Antibodies that Bind Canine PD-1

Confirmation of Monoclonal Antibodies Reactivity Against Canine PD-1

One of the mouse monoclonal antibodies that previously had been raised against human PD-1 [hPD-1.08A, identified in U.S. Pat. No. 8,354,509 B2, hereby incorporated by reference in its entirety] also was found to strongly react with canine PD-1. Purified hPD-1.08A was tested for reactivity with the HIS-tagged ECD domain of canine PD-1 by ELISA as follows: HIS-tagged canine PD-1 ECD protein is diluted to 10 µg/mL in coating buffer (Carbonate/Bicarbonate pH 9.0) and dispensed at 100 µl/well in 96-well flat bottomed ELISA plates (NUNC). The plates are incubated at 4° C. overnight. The plates are then washed three times with phosphate buffered saline containing 0.05% Tween-20 (PBST). Next, 200 µl of blocking buffer (5% skim milk in PBST) is added to each well and the plates are incubated at 37° C. for 60 minutes.

The plates are then washed three times with PBST. Next, 100 µl of test monoclonal antibodies (mAbs) diluted in blocking buffer is added to the first wells of the appropriate columns. Test mAbs are then diluted two-fold to the appropriate plate position. Following incubation of the plates at 37° C. for 60 minutes, the plates are washed three times with PBST. Next, 100 µl per well of a 1:2,000 dilution of a horseradish peroxidase conjugated goat anti-mouse IgG (KPL) is added to the plates, which are then incubated at 37° C. for 60 minutes. Then the plates are washed three times with PBST, and 100 µl/well of 3,3',5,5' tetramethyl benzidine, (TMB) substrate (from KPL) is added to the plates. The color reaction is allowed to develop for 5-20 minutes at 37° C. prior to measuring absorbance at 650 nm.

CHO Cells Expressing Canine PD-1 Protein

The full length canine PD-1 gene was cloned into plasmid p96793. In this plasmid the expression of the canine PD-1 protein is driven by an hCMV promoter. CHO DXB11 cells (dhfr−) were maintained in MEM-alpha (Gibco) supplemented with 10% fetal bovine serum.

Transfection of CHO cells with plasmid p96793 was carried out in 75 $cm^2$ flasks containing approximately $6\times10^6$ cells by liposome-mediated gene delivery using Lipofectamine (Invitrogen). After 48 hours, cells were passaged into MEM-alpha medium without nucleosides, supplemented with 10% FBS and 400 µg/mL hygromycin B (selective medium). Limited-dilution cloning was performed on the pool of dhfr+, hygromycin resistant cells. Clones were assessed for expression of canine PD-1 by immunofluorescence assay. Briefly, cell monolayers were fixed in 96 well plates with 80% acetone. Fixed and dried cell monolayers were then incubated for 1 hour with a polyclonal goat anti-human PD-1 antibody (R&D Systems). Plates were washed with PBS, then incubated for 1 hour with a fluorescein-labeled rabbit anti-goat IgG antibody (KPL). Plates were washed with PBS. Clones exhibiting fluorescence were expanded and cell stocks were established.

Reactivity of Mouse mAbs Against Canine PD-1 Proteins Expressed on CHO Cells

The reactivity of mouse anti-human PD-1 mAbs with canine PD-1 on CHO cells was determined by a cell-based assay using CHO cells that express PD-1. Briefly, the CHO cells expressing canine PD-1 were cultured to 80-100% confluency in 50 µl media (DMEM/HAM's F12, 10% FBS; "CHO Media"). Next, 50 µl of media containing various concentrations of purified mAbs were added for 1 hour at 37° C. Following three washes with PBS-TWEEN, 100 µl of goat anti-mouse horse radish peroxidase (HRP) diluted 1:1000 in culture media was added for one hour at 37° C. After three additional washes with PBS-TWEEN, bound mAbs were visualized with a peroxidase substrate (TMB). The absorbance increase due to peroxidase activity at 450 nm was measured in a microplate reader. Color development is stopped by adding 50 µL per well of 1 M phosphoric acid.

Ligand Blockade by Mouse and Caninized Anti-PD-1 mAbs

For mouse anti-human PD-1 mAbs which react with canine PD-1, a cell-based ELISA (CELISA) assay based on the CHO cell line expressing canine PD-1 was used. Ligand blockade was confirmed using this assay in conjunction with biotinylated cPD-L1/Fc protein. Briefly, seed cPD-1 CHO cells in 96-well plates at $4\times10^4$ cells per well and incubate cells at 37° C. for 18-24 hours till they are 95-100% confluent. Aspirate cell culture media, wash the plates 3 times with PBS+0.05% Tween20 and 1×CHO media. Make 3-fold serial dilutions of anti-cPD1 mAbs in CHO media, starting at 30 µg/mL, and add 50 µL/well of each antibody dilution to the plate. Incubate at 37° C., 5% CO$_2$ with shaking for 30 min. Add 50 µL/well of cPD-L1-Fc-biotin (2 ug/ml in CHO media stock) and continue to incubate at 37° C., 5% CO$_2$ with shaking for 45 min. Wash the plates six times with PBS+0.05% Tween 20. Add 100 ul/well of 1:2000 Streptavidin-Horse Radish Peroxidase (Streptavidin-HRP) in CHO media and incubate 30-60 min at 37° C./5% CO$_2$. Wash the plates five times with PBS+0.05% Tween20. Add 100 µl/well of TMB color developing substrate. Stop color development by adding 50 µl/well of 1M phosphoric acid. Measure optical density (O.D.) at A450-A620 using an ELISA plate reader.

Cloning and Identification of DNA Sequences Corresponding to Mouse Hpd-.08A mAb

The DNA sequence of mouse VH and VL chains and the DNA sequences encoding their CDRs are identified as described U.S. Pat. No. 8,354,509 [see, Table IV of U.S. Pat. No. 8,354,509; provided in Table 2 directly below].

TABLE 2

Mouse anti-Human PD-1 CDRs from hPD-1.08A of U.S. Pat. No. 8,354,509

| CDR | Heavy Chain (SEQ ID NO:) | | Light Chain (SEQ ID NO:) | |
| --- | --- | --- | --- | --- |
| | N.A. | A.A. | N.A. | A.A. |
| CDR-1 | 13 | 14 | 19 | 20 |
| CDR-2 | 15 | 16 | 21 | 22 |
| CDR-3 | 17 | 18 | 23 | 24 |

Example 3

Caninization of Mouse Anti-Human Pd-1 Monoclonal Antibodies

In order to execute the process of caninization, the DNA sequence that encodes the heavy and light chains of canine IgG were determined. The DNA and protein sequence of the canine heavy and light chains are known in the art and can be obtained by searching of the NCBI gene and protein databases. There are four known IgG subtypes of dog IgG and they are referred to as IgG-A, IgG-B, IgG-C, and IgG-D. There are two types of light chains in canine antibodies referred to as kappa and lambda. Table 3 lists both the amino and nucleic acid sequences of modified canine heavy (IgG-A, IgG-B, IgG-D) and light (Kappa) antibody chains of the present invention that comprise the murine anti-human PD-1 CDRs of Table 2.

TABLE 3

MODIFIED CANINE HEAVY AND LIGHT CHAIN SEQUENCES#

| Chain type | Subtype | Nucleic Acid SEQ ID NO: | Amino Acid SEQ ID NO: |
| --- | --- | --- | --- |
| H | IgG-A | 25 | 26 |
| H | IgG-B | 27 | 28 |
| H | IgG-D | 29 | 30 |
| L | Kappa (1011) | 31 | 32 |
| L | Kappa (1022) | 33 | 34 |

Sequences do not include the signal sequence.

Construction of Caninized Anti PD-1 Antibodies

Without being bound by any specific approach, the process of producing variants of caninized anti-PD-1 mAbs with various contents of canine and mouse sequences involved the general following scheme:

i) Determine DNA sequence of VH and VL chains of mouse mabs
ii) Identify the H and L chain CDRs of mouse mabs
iii) Identify a suitable H and L chain of canine IgG
iv) Write down the DNA sequence of canine IgG H and L chains
v) Replace the DNA sequence encoding endogenous dog H and L chain CDRs with DNA sequences encoding the respective mouse CDRs. Also, optionally replace some canine frame residues with selected residues from the corresponding mouse frame regions.
vi) Synthesize the DNA from step (v) and clone it into a suitable expression plasmid
vii) Transfect plasmids into HEK 293 cells
viii) Purify expressed antibody from HEK 293 supernatant
ix) Test purified antibody for binding to canine PD-1

The above outlined steps resulted in a set of variant antibodies with various contents of canine and mouse sequences. The present invention identifies the caninized murine anti-human PD-1 antibodies comprising SEQ ID NO: 28 and of SEQ ID NO: 32 or 34 as having particularly tight binding with canine PD-1.

```
Full length canine PD-1 DNA sequence: signal sequence underlined and in bold
Nucleotide sequence SEQ ID NO: 1 is without the signal sequence; and
Nucleotide sequence SEQ ID NO: 35 includes the signal sequence.
atggggagccggcgggggccctggccgctcgtctgggccgtgctgcagctgggctggtggccaggatggctcctag actccctgacaggccctggagcccgctcaccttctcccggcgcagctcacggtgcaggagggagagaacgccac gttcacctgcagcctggccgacatccccgacagcttcgtgctcaactggtaccgcctgagccccgcaaccagacg gacaagctggccgccttccaggaggaccgcatcgagccgggccgggacaggcgcttccgcgtcatgcggctgccca acgggcgggacttccacatgagcatcgtcgctgcgcgcctcaacgacagcggcatctacctgtgcgggggccatcta cctgccccccaacacacagatcaacgagagtccccgcgcagagctctccgtgacggagagaaccctggagcccccc acacagagccccagcccccaccccagactcagcggccagttgcaggggctggtcatcggcgtcacgagcgtgctgg tgggtgtcctgctactgctgctgctgacctgggtcctggccgctgtcttccccagggccacccgaggtgcctgtgt gtgcgggagcgaggacgagcctctgaaggagggccccgatgcagcgcccgtcttcaccctggactacggggagctg gacttccagtggcgagagaagacgccggagccccggcgccctgtgccccggagcagaccgagtatgccaccatcg
```

-continued

```
tcttcccgggcaggccggcgtcccgggccgcagggcctcggccagcagcctgcaggagcccagcctccgagccc cgaggacggacccggcctgtggccctctga
```

Full length canine PD-1 Amino acid sequence: signal sequence underlined and in bold
Amino acid sequence SEQ ID NO: 2 is without the signal sequence; and
Amino acid sequence SEQ ID NO: 36 includes the signal sequence.
MGSRRGPWPLVWAVLQLGWWPGWLLDSPDRPWSPLTFSPAQLTVQEGENATFTCSLADIPDSFVLNWYRLSPRNQT

DKLAAFQEDRIEPGRDRRFRVMRLPNGRDFHMSIVAARLNDSGIYLCGAIYLPPNTQINESPRAELSVTERTLEPP

TQSPSPPPRLSGQLQGLVIGVTSVLVGVLLLLLLTWVLAAVFPRATRGACVCGSEDEPLKEGPDAAPVFTLDYGEL

DFQWREKTPEPPAPCAPEQTEYATIVFPGRPASPGRRASASSLQGAQPPSPEDGPGLWPL

Canine PD-1 extracellular domain_DNA sequence: SEQ ID NO: 3 (Codon optimized for
expression in CHO cells)
```
ctggattccccgacagaccctggagccctctcaccttctcccctgcccagctgaccgtccaggaaggcgagaatg ccaccttcacctgcagcctcgccgacatccccgacagcttcgtgctgaactggtacagactgagccccaggaacca gaccgacaagctggccgcttttccaggaggacaggatcgaacccggcagggacaggaggtttagggtcatgaggctg cccaacggcagggacttccacatgtccatcgtggccgccagactgaacgactccggcatctacctgtgcggcgcta tctacctgccccccaacacccagatcaacgagagccccagggccgaactgagcgtgacagagagaaccctggaacc tcccacccagagcccttcccctcctctagactgagcggacagctgcagggcctggtg
```

Canine PD-1 extracellular domain: SEQ ID NO: 4:
LDSPDRPWSPLTESPAQLTVQEGENATFTCSLADIPDSFVLNWYRLSPRNQTDKLAAFQEDRIEPGRDRRFRVMRL

PNGRDFHMSIVAARLNDSGIYLCGAIYLPPNTQINESPRAELSVTERTLEPPTQSPSPPPRLSGQLQGLV

Canine PD-1 extracellular domain-human IgG1 Fc DNA sequence: SEQ ID NO: 5 (Codon
optimized for expression in HEK-293 cells)
```
ctggattccccgacagaccctggagccctctcaccttctcccctgcccagctgaccgtccaggaaggcgagaatg ccaccttcacctgcagcctcgccgacatccccgacagcttcgtgctgaactggtacagactgagccccaggaacca gaccgacaagctggccgcttttccaggaggacaggatcgaacccggcagggacaggaggtttagggtcatgaggctg cccaacggcagggacttccacatgtccatcgtggccgccagactgaacgactccggcatctacctgtgcggcgcta tctacctgccccccaacacccagatcaacgagagccccagggccgaactgagcgtgacagagagaaccctggaacc tcccacccagagcccttcccctcctctagactgagcggacagctgcagggcctggtgggtaccgacaaaactcac acatgcccaccgtgcccagcacctgaactcctggggggaccgtcagtcttcctcttccccccaaaacccaaggaca ccctcatgatctcccggacccctgaggtcacatgcgtggtggtggacgtgagccacgaagaccctgaggtcaagtt caactggtacgtggacggcgtggaggtgcataatgccaagacaaagccgcgggaggagcagtacaacagcacgtac cgtgtggtcagcgtcctcaccgtcctgcaccaggactggctgaatggcaaggagtacaagtgcaaggtctccaaca aagcccttccagcccccatcgagaaaaccatctccaaagccaaagggcagccccgagaaccacaggtgtacaccct gcccccatcccgggatgagctgaccaagaaccaggtcagcctgacctgcctggtcaaaggcttctatcccagcgac atcgccgtggagtgggagagcaatgggcagccggagaacaactacaagaccacgcctcccgtgctggactccgacg gctccttcttcctctacagcaagctcaccgtggacaagagcaggtggcagcaggggaacgtcttctcatgctccgt gatgcatgaggctctgcacaaccactacacgcagaagagcctctccctgtctccgggtaaatga
```

Canine PD-1 extracellular domain-human IgG1 Fc fusion protein: signal sequence
underlined and in bold: SEQ ID NO: 6; SEQ ID NO: 53 includes the signal sequence.
MNFLLSWVHWSLALLLYLHHAKWSQALDSPDRPWSPLTFSPAQLTVQEGENATFTCSLADIPDSFVLNWYRLSPRN

QTDKLAAFQEDRIEPGRDRRFRVMRLPNGRDFHMSIVAARLNDSGIYLCGAIYLPPNTQINESPRAELSVTERTLE

PPTQSPSPPPRLSGQLQGLVGTDKTHTCPPCPAPELLGGPSVFLFPPKPKDTLMISRTPEVTCVVVDVSHEDPEVK

FNWYVDGVEVHNAKTKPREEQYNSTYRVVSVLTVLHQDWLNGKEYKCKVSNKALPAPIEKTISKAKGQPREPQVYT

LPPSRDELTKNQVSLTCLVKGFYPSDIAVEWESNGQPENNYKTTPPVLDSDGSFFLYSKLTVDKSRWQQGNVESCS

VMHEALHNHYTQKSLSLSPGK

-continued

Full length canine PD-L1 DNA sequence: signal sequence underlined and in bold
Nucleotide sequence SEQ ID NO: 7 is without the signal sequence; and
Nucleotide sequence SEQ ID NO: 37 includes the signal sequence.
atgagaatgtttagtgtctttacattcatggcctactgccatttgctaaaagcatttacgatcacagtttctaagg acctgtatgtggtagagtatggtggcaatgtgacaatggaatgcaaattcccggtggaaaaacagttaaacttgtt tgcactaatcgtctactgggaaatggaggataaaaaaattatacaatttgtgaatggaaaggaagacctgaaagtt cagcacagcagctacgccagagggctcagctattgaaggaccagctcttcttggggaaggctgcgcttcagatca cagatgtgagattgcaggatgcaggggtttactgctgcttgatcggctatggcggtgctgactacaagcggattac tttgaaagttcatgccccgtaccgcaacatcagccaaagaatttctgtggatcctgtcacctctgaacatgaacta atgtgtcaggctgagggttaccctgaggctgaagtcatctggacaagcagtgaccaccgagtcctgagtggcaaaa ccaccatcactaattccaatagggaagagaagcttttcaatgtgaccagcacgctgaacatcaatgcaacagctaa tgagattttctactgcacttttcaaagatcaggtcctgaggaaaacaatactgccgagttggtcatcccagaacga ctgcccgttccagcaagtgagaggactcatttcatgattctgggaccttcctgttgcttcttggtgtagtcctgg cagtcactttctgtctaaaaaaacatgggagaatgatggatgtggaaaaatgttgcacccgagataggaactcaaa gaaacgaaatgatatacaatttgaagagacataa Full length canine PD-L1: signal sequence underlined and in bold
Amino acid sequence SEQ ID NO: 8 is without the signal sequence; and
Amino acid sequence SEQ ID NO: 38 includes the signal sequence.
MRMFSVFTFMAYCHLLKAFTITVSKDLYVVEYGGNVTMECKFPVEKQLNLFALIVYWEMEDKKIIQFVNGKEDLKV

QHSSYSQRAQLLKDQLFLGKAALQITDVRLQDAGVYCCLIGYGGADYKRITLKVHAPYRNISQRISVDPVTSEHEL

MCQAEGYPEAEVIWTSSDHRVLSGKTTITNSNREEKLFNVTSTLNINATANEIFYCTFQRSGPEENNTAELVIPER

LPVPASERTHFMILGPFLLLLGVVLAVTFCLKKHGRMMDVEKCCTRDRNSKKRNDIQFEET

Canine PD-L1 extracellular domain DNA sequence: SEQ ID NO: 9 (Codon optimized for
expression in CHO cells)
tttaccatcaccgtgtccaaggacctgtacgtggtcgagtacggcggcaatgtgaccatggagtgcaagttccccg tggagaagcagctgaacctgttcgccctcatcgtgtactgggagatggaggacaagaagatcatccagttcgtgaa cggcaaggaggacctgaaggtgcagcactccagctactcccagagagcccagctgctgaaggaccagctgttcctg ggcaaggccgccctgcagatcaccgacgtgagactgcaggacgccggcgtgtattgctgcctgatcggctacggag gcgccgactacaagaggatcaccctgaaggtgcatgcaccctacaggaacatcagccagaggatcagcgtcgatcc cgtgaccagcgagcacgagctgatgtgccaagccgagggctatcccgaggccgaagtgatctggaccagcagcgac cacagggtcctgagcggcaagaccaccatcaccaacagcaacagggaggagaagctgttcaacgtgaccagcaccc tcaacatcaacgccaccgccaacgagatcttctactgcaccttccagaggagcggccccgaagagaacaacaccgc cgagctggtgatccccgagagactgcctgtgcctgccagcgagaggacccac Canine PD-L1 extracellular domain protein: SEQ ID NO: 10
FTITVSKDLYVVEYGGNVTMECKFPVEKQLNLFALIVYWEMEDKKIIQFVNGKEDLKVQHSSYSQRAQLLKDQLFL

GKAALQITDVRLQDAGVYCCLIGYGGADYKRITLKVHAPYRNISQRISVDPVTSEHELMCQAEGYPEAEVIWTSSD

HRVLSGKTTITNSNREEKLFNVTSTLNINATANEIFYCTFQRSGPEENNTAELVIPERLPVPASERTH

Canine PD-L1 extracellular domain-human IgG1 Fc DNA sequence: SEQ ID NO: 11
(Codon optimized for expression in HEK-293 cells)
tttaccatcaccgtgtccaaggacctgtacgtggtcgagtacggcggcaatgtgaccatggagtgcaagttccccg tggagaagcagctgaacctgttcgccctcatcgtgtactgggagatggaggacaagaagatcatccagttcgtgaa cggcaaggaggacctgaaggtgcagcactccagctactcccagagagcccagctgctgaaggaccagctgttcctg ggcaaggccgccctgcagatcaccgacgtgagactgcaggacgccggcgtgtattgctgcctgatcggctacggag gcgccgactacaagaggatcaccctgaaggtgcatgcaccctacaggaacatcagccagaggatcagcgtcgatcc cgtgaccagcgagcacgagctgatgtgccaagccgagggctatcccgaggccgaagtgatctggaccagcagcgac cacagggtcctgagcggcaagaccaccatcaccaacagcaacagggaggagaagctgttcaacgtgaccagcaccc -continued tcaacatcaacgccaccgccaacgagatcttctactgcaccttcagaggagcggccccgaagagaacaacaccgc cgagctggtgatccccgagagactgcctgtgcctgccagcgagaggacccacggtaccgacaaaactcacacatgc ccaccgtgcccagcacctgaactcctgggggaccgtcagtcttcctcttccccccaaaacccaaggacaccctca tgatctcccggacccctgaggtcacatgcgtggtggtggacgtgagccacgaagaccctgaggtcaagttcaactg gtacgtggacggcgtggaggtgcataatgccaagacaaagccgcgggaggagcagtacaacagcacgtaccgtgtg gtcagcgtcctcaccgtcctgcaccaggactggctgaatggcaaggagtacaagtgcaaggtctccaacaaagccc tcccagcccccatcgagaaaaccatctccaaagccaaagggcagccccgagaaccacaggtgtacaccctgccccc atcccgggatgagctgaccaagaaccaggtcagcctgacctgcctggtcaaaggcttctatcccagcgacatcgcc gtggagtgggagagcaatgggcagccggagaacaactacaagaccacgcctcccgtgctggactccgacggctcct tcttcctctacagcaagctcaccgtggacaagagcaggtggcagcaggggaacgtcttctcatgctccgtgatgca tgaggctctgcacaaccactacacgcagaagagcctctccctgtctccgggtaaatga Canine PD-L1 extracellular domain-human IgG1 Fc fusion protein: SEQ ID NO: 12
FTITVSKDLYVVEYGGNVTMECKFPVEKQLNLFALIVYWEMEDKKIIQFVNGKEDLKVQHSSYSQRAQLLKDQLFL

GKAALQITDVRLQDAGVYCCLIGYGGADYKRITLKVHAPYRNISQRISVDPVTSEHELMCQAEGYPEAEVIWTSSD

HRVLSGKTTITNSNREEKLENVTSTLNINATANEIFYCTFQRSGPEENNTAELVIPERLPVPASERTHGTDKTHTC

PPCPAPELLGGPSVFLEPPKPKDTLMISRTPEVTCVVVDVSHEDPEVKFNWYVDGVEVHNAKTKPREEQYNSTYRV

VSVLTVLHQDWLNGKEYKCKVSNKALPAPIEKTISKAKGQPREPQVYTLPPSRDELTKNQVSLTCLVKGFYPSDIA

VEWESNGQPENNYKTTPPVLDSDGSFFLYSKLTVDKSRWQQGNVFSCSVMHEALHNHYTQKSLSLSPGK

08A VH: CDR H1 DNA: SEQ ID NO: 13:
agttattatc tgtac

08A VH: CDR H1 protein: SEQ ID NO: 14:
Ser Tyr Tyr Leu Tyr

08A VH: CDR H2 DNA: SEQ ID NO: 15:
ggggttaatc ctagtaatgg tggtactaac ttcagtgaga agttcaag 08A VH: CDR H2 protein: SEQ ID NO: 16:
Gly Val Asn Pro Ser Asn Gly Gly Thr Asn Phe Ser Glu Lys Phe
Lys 08A VH: CDR H3 DNA: SEQ ID NO: 17:
agggattcta actacgacgg gggctttgac tac 08A VH: CDR H3 protein: SEQ ID NO: 18:
Arg Asp Ser Asn Tyr Asp Gly Gly Phe Asp Tyr 08A VL: CDR L1 DNA: SEQ ID NO: 19:
agggccagca aaagtgtcag tacatctggc tttagttatt tgcac 08A VL: CDR L1 protein: SEQ ID NO: 20:
Arg Ala Ser Lys Ser Val Ser Thr Ser Gly Phe Ser Tyr Leu His 08A VL: CDR L2 DNA: SEQ ID NO: 21:
cttgcatcca acctagagtc t 08A VL: CDR L2 protein: SEQ ID NO: 22:
Leu Ala Ser Asn Leu Glu Ser 08A VL: CDR L3 DNA: SEQ ID NO: 23:
cagcacagtt gggagcttcc gctcacg 08A VL: CDR L3 protein: SEQ ID NO: 24:
Gln His Ser Trp Glu Leu Pro Leu Thr Caninized Murine Anti-Human PD-1 Antibody 08A canVH-canIgGB-Fc (12G8 signal sequence underlined and in bold): HEAVY CHAIN
Nucleotide sequence SEQ ID NO: 27 is without the signal sequence; and
Nucleotide sequence SEQ ID NO: 41 includes the signal sequence.
ATGGCCGTGCTGGGGCTGCTCTTCTGCCTGGTGACATTCCCAAGCTGTGTGCTAAGCGAGGTGCAGCTGGTGCAGT

CCGGCGGCGATCTGGTGAAGCCTGGAGGCAGCGTGAGACTGAGCTGCGTGGCCAGCGGCTACACCTTCACCAGCTA

-continued

```
CTACCTGTACTGGGTGAGGCAGGCTCCTGGCAAAGGACTGCAGTGGATCGGCGGCGTGAATCCTAGCAACGGCGGC

ACCAACTTCAGCGAGAAGTTCAAGAGCAGGGCCACCCTGAGCGTGGACAAGGCCAAGAACACCGCCTACATGCAGC

TGAACTCCCTGAGGGCCGAGGACACCGCCGTGTACTACTGCACCAGGAGGGACAGCAACTACGACGGCGGCTTCGA

CTACTGGGGACAGGGAACCCTGCTGACCGTGTCCAGCGCTTCCACAACCGCGCCATCAGTCTTTCCGTTGGCCCCA

TCATGCGGGTCGACGAGCGGATCGACTGTGGCCCTGGCGTGCTTGGTGTCGGGATACTTTCCCGAACCCGTCACGG

TCAGCTGGAACTCCGGATCGCTTACGAGCGGTGTGCATACGTTCCCCTCGGTCTTGCAATCATCAGGGCTCTACTC

GCTGTCGAGCATGGTAACGGTGCCCTCATCGAGGTGGCCCTCCGAAACGTTCACATGTAACGTAGCACATCCAGCC

TCCAAAACCAAGGTGGATAAACCCGTGCCGAAAAGAGAGAATGGGCGGGTGCCTCGACCCCCTGATTGCCCCAAGT

GTCCGGCTCCGGAAATGCTCGGTGGACCCTCAGTGTTTATCTTCCCTCCGAAGCCCAAGGACACTCTGCTGATCGC

GCGCACTCCAGAAGTAACATGTGTAGTGGTGGACCTTGATCCCGAGGACCCCGAAGTCCAGATCTCCTGGTTTGTA

GATGGGAAACAGATGCAGACCGCAAAAACTCAACCCAGAGAGGAGCAGTTCAACGGAACATACCGAGTGGTATCCG

TCCTTCCGATTGGCCACCAGGACTGGTTGAAAGGGAAGCAGTTTACGTGTAAAGTCAACAATAAGGCGTTGCCTAG

CCCTATTGAGCGGACGATTTCGAAAGCTAGGGGACAGGCCCACCAGCCATCGGTCTATGTCCTTCCGCCTTCCCGC

GAGGAGCTCTCGAAGAATACAGTGAGCCTTACATGCCTCATTAAGGATTTCTTCCCGCCTGATATCGACGTAGAGT

GGCAATCAAACGGTCAACAGGAGCCGGAATCCAAGTATAGAACCACTCCGCCCCAGCTTGACGAGGACGGATCATA

CTTTTTGTATTCAAAACTGTCGGTGGATAAGAGCCGGTGGCAGAGAGGTGACACCTTCATCTGTGCGGTGATGCAC

GAAGCACTCCATAATCACTACACCCAAGAGAGCCTCTCGCATTCCCCCGGAAAGTGA
```

Amino acid sequence SEQ ID NO: 28 is without the signal sequence; and
Amino acid sequence SEQ ID NO: 42 includes the signal sequence.
MAVLGLLFCLVTFPSCVLSEVQLVQSGGDLVKPGGSVRLSCVASGYTFTSYYLYWVRQAPGKGLQWIGGVNPSNGG

TNFSEKFKSRATLSVDKAKNTAYMQLNSLRAEDTAVYYCTRRDSNYDGGFDYWGQGTLLTVSSASTTAPSVFPLAP

SCGSTSGSTVALACLVSGYFPEPVTVSWNSGSLTSGVHTFPSVLQSSGLYSLSSMVTVPSSRWPSETFTCNVAHPA

SKTKVDKPVPKRENGRVPRPPDCPKCPAPEMLGGPSVFIFPPKPKDTLLIARTPEVTCVVVDLDPEDPEVQISWFV

DGKQMQTAKTQPREEQFNGTYRVVSVLPIGHQDWLKGKQFTCKVNNKALPSPIERTISKARGQAHQPSVYVLPPSR

EELSKNTVSLTCLIKDFFPPDIDVEWQSNGQQEPESKYRTTPPQLDEDGSYFLYSKLSVDKSRWQRGDTFICAVMH

EALHNHYTQESLSHSPGK canVH-canIgGA-Fc (12G8 signal sequence underlined and in bold): HEAVY CHAIN
Nucleotide sequence SEQ ID NO: 25 is without the signal sequence; and
Nucleotide sequence SEQ ID NO: 39 includes the signal sequence.
ATGGCCGTGCTGGGGCTGCTCTTCTGCCTGGTGACATTCCCAAGCTGTGTGCTAAGCGAGGTGCAGCTGGTGCAGT

```
CCGGCGGCGATCTGGTGAAGCCTGGAGGCAGCGTGAGACTGAGCTGCGTGGCCAGCGGCTACACCTTCACCAGCTA

CTACCTGTACTGGGTGAGGCAGGCTCCTGGCAAAGGACTGCAGTGGATCGGCGGCGTGAATCCTAGCAACGGCGGC

ACCAACTTCAGCGAGAAGTTCAAGAGCAGGGCCACCCTGAGCGTGGACAAGGCCAAGAACACCGCCTACATGCAGC

TGAACTCCCTGAGGGCCGAGGACACCGCCGTGTACTACTGCACCAGGAGGGACAGCAACTACGACGGCGGCTTCGA

CTACTGGGGACAGGGAACCCTGCTGACCGTGTCCAGCGCTTCCACAACCGGCTCCGTCGGTGTTTCCCCTGGCACCT

AGCTGCGGGTCGACCTCGGGTAGCACAGTGGCGCTGGCGTGTTTGGTGTCGGGATACTTTCCCGAGCCGGTAACGG

TGTCATGGAACTCAGGGTCACTTACATCAGGAGTCCATACTTTTCCGTCCGTGCTGCAGTCAAGCGGCTTGCATTC

ACTGTCCTCGATGGTGACGGTGCCTTCGTCGAGGTGGCCCAGCGAAACGTTCACTTGTAACGTAGTACACCCGGCC

TCCAACACGAAAGTCGATAAACCGGTATTCAATGAGTGCAGATGTACAGACACCCCTCCCTGTCCGGTACCCGAAC

CCCTTGGAGGGCCGAGCGTCCTCATCTTCCCTCCCAAGCCAAAAGACATCTTGCGCATTACGAGGACACCAGAAGT

CACGTGCGTAGTGCTTGATCTCGGTAGAGAAGATCCCGAGGTCCAGATCTCGTGGTTTGTGGATGGAAAGGAGGTC

CACACCGCAAAGACTCAGTCGCGCGAGCAGCAGTTCAATGGCACGTATCGGGTCGTGAGCGTGCTTCCTATCGAGC

ATCAGGACTGGCTCACCGGGAAGGAGTTCAAATGCCGGGTCAATCATATCGACCTCCCGTCACCAATCGAGCGGAC
```

```
CATCTCGAAGGCTAGAGGAAGGGCGCACAAACCTTCGGTCTATGTGCTTCCCCCATCGCCCAAAGAGCTTTCCTCG

TCGGATACGGTGTCCATTACATGCTTGATTAAGGACTTCTATCCTCCTGATATTGATGTGGAATGGCAATCAAACG

GACAGCAGGAGCCGGAACGCAAGCACCGAATGACCCCACCGCAATTGGACGAAGATGGTAGCTACTTTCTCTACTC

AAAGCTCTCAGTCGACAAATCCCGATGGCAGCAGGGAGATCCCTTCACTTGCGCCGTGATGCACGAGACACTCCAA

AATCATTACACGGACCTTTCGTTGAGCCACTCGCCCGGAAAG
```

Amino acid sequence SEQ ID NO: 26 is without the signal sequence; and
Amino acid sequence SEQ ID NO: 40 includes the signal sequence.
MAVLGLLFCLVTFPSCVLSEVQLVQSGGDLVKPGGSVRLSCVASGYTFTSYYLYWVRQAPGKGLQWIGGVNPSNGG

TNFSEKFKSRATLSVDKAKNTAYMQLNSLRAEDTAVYYCTRRDSNYDGGFDYWGQGTLLTVSSASTTAPSVFPLAP

SCGSTSGSTVALACLVSGYFPEPVTVSWNSGSLTSGVHTFPSVLQSSGLHSLSSMVTVPSSRWPSETFTCNVVHPA

SNTKVDKPVFNECRCTDTPPCPVPEPLGGPSVLIFPPKPKDILRITRTPEVTCVVLDLGREDPEVQISWFVDGKEV

HTAKTQSREQQFNGTYRVVSVLPIEHQDWLTGKEFKCRVNHIDLPSPIERTISKARGRAHKPSVYVLPPSPKELSS

SDTVSITCLIKDFYPPDIDVEWQSNGQQEPERKHRMTPPQLDEDGSYFLYSKLSVDKSRWQQGDPFTCAVMHETLQ

NHYTDLSLSHSPGK canVH-canIgGD-Fc (12G8 signal sequence underlined and in bold): HEAVY CHAIN
Nucleotide sequence SEQ ID NO: 29 is without the signal sequence; and
Nucleotide sequence SEQ ID NO: 43 includes the signal sequence.
```
ATGGCCGTGCTGGGCTGCTCTTCTGCCTGGTGACATTCCCAAGCTGTGTGCTAAGCGAGGTGCAGCTGGTGCAGT

CCGGCGGCGATCTGGTGAAGCCTGGAGGCAGCGTGAGACTGAGCTGCGTGGCCAGCGGCTACACCTTCACCAGCTA

CTACCTGTACTGGGTGAGGCAGGCTCCTGGCAAAGGACTGCAGTGGATCGGCGGCGTGAATCCTAGCAACGGCGGC

ACCAACTTCAGCGAGAAGTTCAAGAGCAGGGCCACCCTGAGCGTGGACAAGGCCAAGAACACCGCCTACATGCAGC

TGAACTCCCTGAGGGCCGAGGACACCGCCGTGTACTACTGCACCAGGAGGGACAGCAACTACGACGGCGGCTTCGA

CTACTGGGGACAGGGAACCCTGCTGACCGTGTCCAGCGCTTCAACCACAGCGCCGAGCGTGTTCCCTCTGGCGCCG

TCGTGCGGTTCCACCTCGGGATCAACAGTGGCCCTCGCCTGTCTCGTGAGCGGATACTTTCCGGAGCCTGTCACGG

TGTCGTGGAATAGCGGATCACTCACGTCGGGCGTGCATACTTTTCCATCCGTCTTGCAATCGAGCGGATTGTACTC

ACTCTCCTCAACCGTCACTGTCCCCTCGTCGCGCTGGCCCTCGGAGACTTTTACGTGCAATGTAGTCCATCCGGCG

AGCAACACGAAGGTCGACAAGCCCGTACCCAAGGAATCAACATGCAAGTGCATCTCGCCCTGTCCCGTCCCCGAAT

CCCTTGGTGGCCCCTCAGTGTTTATCTTCCCTCCGAAGCCTAAAGACATCTTGAGAATCACAAGAACACCGGAAAT

CACGTGTGTGGTCCTTGACTTGGGACGCGAGGACCCTGAGGTACAAATCTCGTGGTTTGTGGACGGGAAGAGGTG

CACACAGCAAAGACACAACCACGCGAGCAGCAGTTTAACTCAACGTACAGGGTAGTATCCGTACTTCCCATTGAAC

ACCAGGATTGGCTCACCGGTAAAGAATTCAAATGCCGAGTGAATCACATCGGGCTTCCTAGCCCAATTGAGCGGAC

GATTTCCAAAGCTAGGGGTCAGGCCCACCAGCCGAGCGTATACGTGTTGCCGCCCTCCCCGAAGGAGCTGTCATCG

TCAGATACGGTAACGTTGACGTGTCTGATCAAAGATTTCTTTCCTCCCGAAATTGATGTGGAATGGCAAAGCAATG

GGCAGCCCGAGCCCGAGTCAAAGTACCATACTACTGCACCACAGCTGGACGAAGATGGATCGTATTTCCTCTACTC

GAAACTGTCCGTGGATAAGTCCCGGTGGCAGCAAGGGGACACCTTCACTTGCGCGGTCATGCACGAGGCACTTCAG

AACCACTATACGGACTTGAGCCTCTCGCATTCGCCAGGGAAG
```

Amino acid sequence SEQ ID NO: 30 is without the signal sequence; and
Amino acid sequence SEQ ID NO: 44 includes the signal sequence.
MAVLGLLFCLVTFPSCVLSEVQLVQSGGDLVKPGGSVRLSCVASGYTFTSYYLYWVRQAPGKGLQWIGGVNPSNGG

TNFSEKFKSRATLSVDKAKNTAYMQLNSLRAEDTAVYYCTRRDSNYDGGFDYWGQGTLLTVSSASTTAPSVFPLAP

SCGSTSGSTVALACLVSGYFPEPVTVSWNSGSLTSGVHTFPSVLQSSGLYSLSSTVTVPSSRWPSETFTCNVVHPA

SNTKVDKPVPKESTCKCISPCPVPESLGGPSVFIFPPKPKDILRITRTPEITCVVLDLGREDPEVQISWFVDGKEV

HTAKTQPREQQFNSTYRVVSVLPIEHQDWLTGKEFKCRVNHIGLPSPIERTISKARGQAHQPSVYVLPPSPKELSS

-continued

SDTVTLTCLIKDFFPPEIDVEWQSNGQPEPESKYHTTAPQLDEDGSYFLYSKLSVDKSRWQQGDTFTCAVMHEALQ

NHYTDLSLSHSPGK canVL-canKappa (1022)xHGF signal sequence underlined and in bold: LIGHT CHAIN
Nucleotide sequence SEQ ID NO: 33 is without the signal sequence; and
Nucleotide sequence SEQ ID NO: 47 includes the signal sequence.
ATGGATATGAGAGTACCTGCACAACTTCTGGGATTGCTGCTTCTTTGGCTGAGAGGGGCCCGCTGCGATATCGTCC

TGACCCAGACCCCTCCTAGCCTGTCCGTGAGCCCTGGAGAACCCGCCAGCATCAGCTGCAGGGCCTCCAAGAGCGT

GAGCACCAGCGGCTTCAGCTACCTGCACTGGTACAGGCAGAAGCCCGGACAGCCTCCTCAGCTGCTGATCTTCCTG

GCCAGCAACCTGGAGAGCGGCGTGCCTGACAGGTTTAGCGGAAGCGGCAGCGGCACCGACTTCACACTGAGGATCT

CCAGGGTGGAAGCCGACGACGCCGGAGTGTACTACTGCCAGCACAGCTGGGAACTGCCCCTGACCTTCGGCCAGGG

CACCAAGGTGGAGATCAAGAGGAACGACGCTCAGCCAGCCGTGTACCTCTTCCAGCCTTCGCCGGACCAGCTTCAT

ACGGGGTCAGCGTCGGTGGTGTGCCTGTTGAACTCGTTTTACCCCAAGGACATTAACGTGAAGTGGAAGGTAGACG

GGGTAATTCAAGACACTGGCATTCAAGAGTCCGTCACGGAACAAGACTCAAAAGACTCAACGTATTCACTGTCGTC

AACCTTGACGATGTCAAGCACCGAGTATCTTAGCCATGAGCTGTATTCGTGCGAGATCACCCACAAGTCCCTCCCC

TCCACTCTTATCAAATCCTTTCAGCGGTCGGAATGTCAGCGGGTCGAT

Amino acid sequence SEQ ID NO: 34 is without the signal sequence; and
Amino acid sequence SEQ ID NO: 48 includes the signal sequence.
MDMRVPAQLLGLLLLWLRGARCDIVLTQTPPSLSVSPGEPASISCRASKSVSTSGFSYLHWYRQKPGQPPQLLIFL

ASNLESGVPDRFSGSGSGTDFTLRISRVEADDAGVYYCQHSWELPLTFGQGTKVEIKRNDAQPAVYLFQPSPDQLH

TGSASVVCLLNSFYPKDINVKWKVDGVIQDTGIQESVTEQDSKDSTYSLSSTLTMSSTEYLSHELYSCEITHKSLP

STLIKSFQRSECQRVD canVL-canKappa (1011)(xHGF signal sequence underlined and in bold: LIGHT CHAIN
Nucleotide sequence SEQ ID NO: 31 is without the signal sequence; and
Nucleotide sequence SEQ ID NO: 45 includes the signal sequence.
ATGGATATGAGAGTACCTGCACAACTTCTGGGATTGCTGCTTCTTTGGCTGAGAGGGGCCCGCTGCGATATCGTCC

TGACCCAGACCCCTCTGAGCCTGTCCGTGAGCCCTGGAGAACCCGCCAGCATCAGCTGCAGGGCCTCCAAGAGCGT

GAGCACCAGCGGCTTCAGCTACCTGCACTGGTACAGGCAGAAGCCCGGACAGAGCCCTCAGCTGCTGATCTTCCTG

GCCAGCAACCTGGAGAGCGGCGTGCCTGACAGGTTTAGCGGAAGCGGCAGCGGCACCGACTTCACACTGAGGATCT

CCAGGGTGGAAGCCGACGACGCCGGAGTGTACTACTGCCAGCACAGCTGGGAACTGCCCCTGACCTTCGGCCAGGG

CACCAAGGTGGAGATCAAGAGGAACGACGCTCAGCCAGCCGTGTACCTCTTCCAGCCTTCGCCGGACCAGCTTCAT

ACGGGGTCAGCGTCGGTGGTGTGCCTGTTGAACTCGTTTTACCCCAAGGACATTAACGTGAAGTGGAAGGTAGACG

GGGTAATTCAAGACACTGGCATTCAAGAGTCCGTCACGGAACAAGACTCAAAAGACTCAACGTATTCACTGTCGTC

AACCTTGACGATGTCAAGCACCGAGTATCTTAGCCATGAGCTGTATTCGTGCGAGATCACCCACAAGTCCCTCCCC

TCCACTCTTATCAAATCCTTTCAGCGGTCGGAATGTCAGCGGGTCGAT

Amino acid sequence SEQ ID NO: 32 is without the signal sequence; and
Amino acid sequence SEQ ID NO: 46 includes the signal sequence.
MDMRVPAQLLGLLLLWLRGARCDIVLTQTPLSLSVSPGEPASISCRASKSVSTSGFSYLHWYRQKPGQSPQLLIFL

ASNLESGVPDRFSGSGSGTDFTLRISRVEADDAGVYYCQHSWELPLTFGQGTKVEIKRNDAQPAVYLFQPSPDQLH

TGSASVVCLLNSFYPKDINVKWKVDGVIQDTGIQESVTEQDSKDSTYSLSSTLTMSSTEYLSHELYSCEITHKSLP

STLIKSFQRSECQRVD

Example 4

Mutant Canine IgG-B Antibodies Specific to Pd-1

There are four known IgG heavy chain subtypes of dog IgG and they are referred to as IgG-A, IgG-B, IgG-C, and IgG-D. The two known light chain subtypes are referred to as lambda and kappa. However, besides binding and activating of canine immune cells, a canine or caninized antibody against PD-1 optimally has two attributes:

1. lack of effector functions such as antibody-dependent cytotoxicity (ADCC) and complement-dependent cytotoxicity (CDC), and
2. be readily purified on a large scale using industry standard technologies such as that based on protein A chromatography.

None of the naturally occurring canine IgG isotypes satisfy both criteria. For example, IgG-B can be purified using protein A, but has a high level of ADCC activity. IgG-C also has considerable ADCC activity. On the other hand, IgG-A binds weakly to protein A, but displays undesirable ADCC activity. Moreover, neither IgG-C nor IgG-D can be purified on protein A columns, although IgG-D display no ADCC activity. The present invention overcomes this difficulty by providing mutant canine IgG-B antibodies specific to PD-1; such antibodies lack effector functions such as ADCC and can be easily of purified using industry standard protein A chromatography. The exact modifications are shown in FIGS. 4A-4B.

The IgG-B variants with reduced effector functions described encompass a first IgG-B variant in which an aspartic acid (D 277) and an asparagine (N 325) residue is each mutated to an alanine residue [cIgGB(-) ADCC], a second variant in which the hinge region of IgG-B is replaced by the hinge region of IgG-D [cIgGB(+) D-hinge], and a third variant in which the hinge region of IgG-B is replaced with the hinge region of IgG-A [cIgGB(+) A-hinge]. Additionally, the second and third variants also include replacement of the same aspartic acid and asparagine residues of the first variant with an alanine residue. The numbering of the aspartic acid and asparagine residues mutated in this invention is based on the numbering scheme described for canine IgG heavy chains in Tang et al., [*Vet Immunol and Immunopathol*, 80:259-270 (2001)].

```
Canine IgGB wt
                                      SEQ ID NO: 49
SASTTAPSVFPLAPSCGSTSGSTVALACLVSGYFPEPVTVSWNSGSLTS

GVHTFPSVLQSSGLYSLSSMVTVPSSRWPSETFTCNVAHPASKTKVDKP

VPKRENGRVPRPPDCPKCPAPEMLGGPSVFIFPPKPKDTLLIARTPEVT

CVVVDLDPEDPEVQISWFVDGKQMQTAKTQPREEQFNGTYRVVSVLPIG

HQDWLKGKQFTCKVNNKALPSPIERTISKARGQAHQPSVYVLPPSREEL

SKNTVSLTCLIKDFFPPDIDVEWQSNGQQEPESKYRTTPPQLDEDGSYF

LYSKLSVDKSRWQRGDTFICAVMHEALHNHYTQESLSHSPGK

Canine IgGB(+)A-hinge
                                      SEQ ID NO: 50
SASTTAPSVFPLAPSCGSTSGSTVALACLVSGYFPEPVTVSWNSGSLTS

GVHTFPSVLQSSGLYSLSSMVTVPSSRWPSETFTCNVAHPASKTKVDKP

VFNECRCTDTPPCPAPEMLGGPSVFIFPPKPKATLLIARTPEVTCVVVD

LDPEDPEVQISWFVDGKQMQTAKTQPREEQFAGTYRVVSVLPIGHQDWL

KGKQFTCKVNNKALPSPIERTISKARGQAHQPSVYVLPPSREELSKNTV

SLTCLIKDFFPPDIDVEWQSNGQQEPESKYRTTPPQLDEDGSYFLYSKL

SVDKSRWQRGDTFICAVMHEALHNHYTQESLSHSPGK

Canine IgGB(+)D-hinge
                                      SEQ ID NO: 51
SASTTAPSVFPLAPSCGSTSGSTVALACLVSGYFPEPVTVSWNSGSLTS

GVHTFPSVLQSSGLYSLSSMVTVPSSRWPSETFTCNVAHPASKTKVDKP

VPKESTCKCISPCPAPEMLGGPSVFIFPPKPKATLLIARTPEVTCVVVD

LDPEDPEVQISWFVDGKQMQTAKTQPREEQFAGTYRVVSVLPIGHQDWL

KGKQFTCKVNNKALPSPIERTISKARGQAHQPSVYVLPPSREELSKNTV

SLTCLIKDFFPPDIDVEWQSNGQQEPESKYRTTPPQLDEDGSYFLYSKL

SVDKSRWQRGDTFICAVMHEALHNHYTQESLSHSPGK

Canine IgGB(-)ADCC
                                      SEQ ID NO: 52
SASTTAPSVFPLAPSCGSTSGSTVALACLVSGYFPEPVTVSWNSGSLTS

GVHTFPSVLQSSGLYSLSSMVTVPSSRWPSETFTCNVAHPASKTKVDKP

VPKRENGRVPRPPDCPKCPAPEMLGGPSVFIFPPKPKATLLIARTPEVT

CVVVDLDPEDPEVQISWFVDGKQMQTAKTQPREEQFAGTYRVVSVLPIG

HQDWLKGKQFTCKVNNKALPSPIERTISKARGQAHQPSVYVLPPSREEL

SKNTVSLTCLIKDFFPPDIDVEWQSNGQQEPESKYRTTPPQLDEDGSYF

LYSKLSVDKSRWQRGDTFICAVMHEALHNHYTQESLSHSPGK
```

SEQUENCE LISTING TABLE 1

| ID | N.A. | A.A. | Description |
|---|---|---|---|
| 1 | ✓ |  | Canine PD-1 Full Length |
| 2 |  | ✓ | Canine PD-1 Full Length |
| 3 | ✓ |  | Canine PD-1 ECD |
| 4 |  | ✓ | Canine PD-1 ECD |
| 5 | ✓ |  | Canine PD-1-Human IgG1 |
| 6 |  | ✓ | Canine PD-1-Human IgG1 |
| 7 | ✓ |  | Canine PD-L1 Full Length |
| 8 |  | ✓ | Canine PD-L1 Full Length |
| 9 | ✓ |  | Canine PD-L1 ECD |
| 10 |  | ✓ | Canine PD-L1 ECD |
| 11 | ✓ |  | Canine PD-L1-Human IgG1 |
| 12 |  | ✓ | Canine PD-L1-Human IgG1 |
| 13 | ✓ |  | hPD-1 CDR1 of $V_H$ |
| 14 |  | ✓ | hPD-1 CDR1 of $V_H$ |
| 15 | ✓ |  | hPD-1 CDR2 of $V_H$ |
| 16 |  | ✓ | hPD-1 CDR2 of $V_H$ |
| 17 | ✓ |  | hPD-1 CDR3 of $V_H$ |
| 18 |  | ✓ | hPD-1 CDR3 of $V_H$ |
| 19 | ✓ |  | hPD-1 CDR1 of $V_L$ |
| 20 |  | ✓ | hPD-1 CDR1 of $V_L$ |
| 21 | ✓ |  | hPD-1 CDR2 of $V_L$ |
| 22 |  | ✓ | hPD-1 CDR2 of $V_L$ |
| 23 | ✓ |  | hPD-1 CDR3 of $V_L$ |
| 24 |  | ✓ | hPD-1 CDR3 of $V_L$ |
| 25 | ✓ |  | IgG-A Heavy |
| 26 |  | ✓ | IgG-A Heavy |
| 27 | ✓ |  | IgG-B Heavy |
| 28 |  | ✓ | IgG-B Heavy |
| 29 | ✓ |  | IgG-D Heavy |
| 30 |  | ✓ | IgG-D Heavy |
| 31 | ✓ |  | Kappa (Light) (1011) |
| 32 |  | ✓ | Kappa (Light) (1011) |
| 33 | ✓ |  | Kappa (Light) (1022) |
| 34 |  | ✓ | Kappa (Light) (1022) |

| SEQUENCE LISTING TABLE 2 (with the LEADER SEQUENCES) | | | |
|---|---|---|---|
| ID | N.A. | A.A. | Description |
| 35 | ✓ | | Canine PD-1 Full Length |
| 36 | | ✓ | Canine PD-1 Full Length |
| 37 | ✓ | | Canine PD-L1 Full Length |
| 38 | | ✓ | Canine PD-L1 Full Length |
| 39 | ✓ | | IgG-A Heavy |
| 40 | | ✓ | IgG-A Heavy |
| 41 | ✓ | | IgG-B Heavy |
| 42 | | ✓ | IgG-B Heavy |
| 43 | ✓ | | IgG-D Heavy |
| 44 | | ✓ | IgG-D Heavy |
| 45 | ✓ | | Kappa (Light) (1011) |
| 46 | | ✓ | Kappa (Light) (1011) |
| 47 | ✓ | | Kappa (Light) (1022) |
| 48 | | ✓ | Kappa (Light) (1022) |
| 53 | | ✓ | Canine PD-1-Human IgG1 Full Length |

| SEQUENCE LISTING TABLE 3 | | | |
|---|---|---|---|
| ID | N.A. | A.A. | Description |
| 49 | | ✓ | cIgGB wt |
| 50 | | ✓ | cIgGB(+)A-hinge |
| 51 | | ✓ | cIgGB(+)D-hinge |
| 52 | | ✓ | cIgGB(-)ADCC |

All references cited herein are incorporated by reference to the same extent as if each individual publication, database entry (e.g. Genbank sequences or GeneID entries), patent application, or patent, was specifically and individually indicated to be incorporated by reference. This statement of incorporation by reference is intended by Applicants, pursuant to 37 C.F.R. § 1.57(b)(1), to relate to each and every individual publication, database entry (e.g. Genbank sequences or GeneID entries), patent application, or patent, each of which is clearly identified in compliance with 37 C.F.R. § 1.57(b)(2), even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

The foregoing written specification is considered to be sufficient to enable one skilled in the art to practice the invention. Various modifications of the invention in addition to those shown and described herein will become apparent to those skilled in the art from the foregoing description and fall within the scope of the appended claims.

We claim:

1. An isolated nucleic acid that encodes the heavy chain of a caninized antibody that specifically binds Programmed Cell Death Receptor 1 (PD-1) comprising a canine IgG heavy chain and a canine kappa light chain; wherein the canine kappa light chain comprises three light chain complementary determining regions (CDRs): CDR light 1 (CDRL1), CDR light 2 (CDRL2), and CDR light 3 (CDRL3); and the canine IgG heavy chain comprises three heavy chain CDRs: CDR heavy 1 (CDRH1), CDR heavy 2 (CDRH2) and CDR heavy 3 (CDRH3):
   (a) wherein CDRL1 comprises the amino acid sequence of SEQ ID NO: 20;
   (b) wherein CDRL2 comprises the amino acid sequence comprising SEQ ID NO: 22;
   (c) wherein CDRL3 comprises the amino acid sequence of SEQ ID NO: 24;
   (d) wherein CDRH1 comprises the amino acid sequence of SEQ ID NO: 14;
   (e) wherein CDRH2 comprises the amino acid sequence of SEQ ID NO: 16; and
   (f) wherein CDRH3 comprises the amino acid sequence of SEQ ID NO: 18;
   wherein the antibody binds canine PD-1 and blocks the binding of canine PD-1 to canine Programmed Cell Death Ligand 1 (PD-L1).

2. The isolated nucleic acid of claim 1 that comprises one or more nucleotide sequences selected from the group consisting of SEQ ID NOs: 13, 15, or 17.

3. The isolated nucleic acid of claim 2 that comprises the nucleotide sequence of SEQ ID NO: 27.

4. An expression vector comprising the isolated nucleic acid of claim 1.

5. An isolated host cell comprising the expression vector of claim 4.

6. An isolated nucleic acid that encodes the light chain of a caninized antibody that specifically binds Programmed Cell Death Receptor 1 (PD-1) comprising a canine IgG heavy chain and a canine kappa light chain; wherein the canine kappa light chain comprises three light chain complementary determining regions (CDRs): CDR light 1 (CDRL1), CDR light 2 (CDRL2), and CDR light 3

(CDRL3); and the canine IgG heavy chain comprises three heavy chain CDRs: CDR heavy 1 (CDRH1), CDR heavy 2 (CDRH2) and CDR heavy 3 (CDRH3):
- (a) wherein CDRL1 comprises the amino acid sequence of SEQ ID NO: 20;
- (b) wherein CDRL2 comprises the amino acid sequence comprising SEQ ID NO: 22;
- (c) wherein CDRL3 comprises the amino acid sequence of SEQ ID NO: 24;
- (d) wherein CDRH1 comprises the amino acid sequence of SEQ ID NO: 14;
- (e) wherein CDRH2 comprises the amino acid sequence of SEQ ID NO: 16; and
- (f) wherein CDRH3 comprises the amino acid sequence of SEQ ID NO: 18;
    wherein the antibody binds canine PD-1 and blocks the binding of canine PD-1 to canine Programmed Cell Death Ligand 1 (PD-L1).

7. The isolated nucleic acid of claim 6 that comprises one or more nucleotide sequences selected from the group consisting of SEQ ID NOs: 21, 23, or 25.

8. The isolated nucleic acid of claim 7 that comprises the nucleotide sequence of SEQ ID NO: 33.

9. An expression vector comprising the isolated nucleic acid of claim 6.

10. An isolated host cell comprising the expression vector of claim 9.

* * * * *

SEQUENCE LISTING

<160> NUMBER OF SEQ ID NOS: 53

<210> SEQ ID NO 1
<211> LENGTH: 795
<212> TYPE: DNA
<213> ORGANISM: Canis familiaris

<400> SEQUENCE: 1

```
ctagactccc ctgacaggcc ctggagcccg ctcaccttct ccccggcgca gctcacggtg      60
caggagggag agaacgccac gttcacctgc agcctggccg acatccccga cagcttcgtg     120
ctcaactggt accgcctgag cccccgcaac cagacggaca gctggccgc cttccaggag     180 gaccgcatcg agccgggccg ggacaggcgc ttccgcgtca tgcggctgcc caacgggcgg     240
gacttccaca tgagcatcgt cgctgcgcgc ctcaacgaca gcggcatcta cctgtgcggg     300
gccatctacc tgccccccaa cacacagatc aacgagagtc cccgcgcaga gctctccgtg     360
acggagagaa ccctggagcc ccccacacag agcccagcc cccacccag actcagcggc     420 cagttgcagg ggctggtcat cggcgtcacg agcgtgctgg tgggtgtcct gctactgctg     480
ctgctgacct gggtcctggc cgctgtcttc ccagggcca cccgaggtgc ctgtgtgtgc     540
gggagcgagg acgagcctct gaaggaggc cccgatgcag cgcccgtctt caccctggac     600
tacggggagc tggacttcca gtggcgagag aagacgccgg agccccggc gccctgtgcc     660 ccggagcaga ccgagtatgc caccatcgtc ttcccgggca ggccggcgtc cccgggccgc     720
```

```
agggcctcgg ccagcagcct gcagggagcc cagcctccga gccccgagga cggacccggc    780
ctgtggcccc tctga                                                     795
```

\<210\> SEQ ID NO 2
\<211\> LENGTH: 264
\<212\> TYPE: PRT
\<213\> ORGANISM: Canis familiaris

\<400\> SEQUENCE: 2

```
Leu Asp Ser Pro Asp Arg Pro Trp Ser Pro Leu Thr Phe Ser Pro Ala
1               5                   10                  15

Gln Leu Thr Val Gln Glu Gly Glu Asn Ala Thr Phe Thr Cys Ser Leu
            20                  25                  30

Ala Asp Ile Pro Asp Ser Phe Val Leu Asn Trp Tyr Arg Leu Ser Pro
        35                  40                  45

Arg Asn Gln Thr Asp Lys Leu Ala Ala Phe Gln Glu Asp Arg Ile Glu
    50                  55                  60

Pro Gly Arg Asp Arg Arg Phe Arg Val Met Arg Leu Pro Asn Gly Arg
65                  70                  75                  80

Asp Phe His Met Ser Ile Val Ala Ala Arg Leu Asn Asp Ser Gly Ile
                85                  90                  95

Tyr Leu Cys Gly Ala Ile Tyr Leu Pro Pro Asn Thr Gln Ile Asn Glu
            100                 105                 110

Ser Pro Arg Ala Glu Leu Ser Val Thr Glu Arg Thr Leu Glu Pro Pro
        115                 120                 125

Thr Gln Ser Pro Ser Pro Pro Arg Leu Ser Gly Gln Leu Gln Gly Gly
    130                 135                 140

Leu Val Ile Gly Val Thr Ser Val Leu Val Gly Val Leu Leu Leu Leu
145                 150                 155                 160

Leu Leu Thr Trp Val Leu Ala Ala Val Phe Pro Arg Ala Thr Arg Gly
                165                 170                 175

Ala Cys Val Cys Gly Ser Glu Asp Glu Pro Leu Lys Glu Gly Pro Asp
            180                 185                 190

Ala Ala Pro Val Phe Thr Leu Asp Tyr Gly Glu Leu Asp Phe Gln Trp
        195                 200                 205

Arg Glu Lys Thr Pro Glu Pro Pro Ala Pro Cys Ala Pro Glu Gln Thr
    210                 215                 220

Glu Tyr Ala Thr Ile Val Phe Pro Gly Arg Pro Ala Ser Pro Gly Arg
225                 230                 235                 240

Arg Ala Ser Ala Ser Ser Leu Gln Gly Ala Gln Pro Pro Ser Pro Glu
                245                 250                 255

Asp Gly Pro Gly Leu Trp Pro Leu
            260
```

\<210\> SEQ ID NO 3
\<211\> LENGTH: 438
\<212\> TYPE: DNA
\<213\> ORGANISM: Artificial Sequence
\<220\> FEATURE:
\<223\> OTHER INFORMATION: codon optimized

\<400\> SEQUENCE: 3

```
ctggattccc ccgacagacc ctggagccct ctcaccttct cccctgccca gctgaccgtc    60
caggaaggcg agaatgccac cttcacctgc agcctcgccg acatccccga cagcttcgtg   120
ctgaactggt acagactgag ccccaggaac cagaccgaca gctggccgc tttccaggag   180
```

```
gacaggatcg aacccggcag ggacaggagg tttagggtca tgaggctgcc caacggcagg      240
gacttccaca tgtccatcgt ggccgccaga ctgaacgact ccggcatcta cctgtgcggc      300
gctatctacc tgcccccaa cacccagatc aacgagagcc cagggccga actgagcgtg       360 acagagagaa ccctggaacc tcccacccag agcccttccc ctcctcctag actgagcgga     420
cagctgcagg gcctggtg                                                    438
```

```
<210> SEQ ID NO 4
<211> LENGTH: 146
<212> TYPE: PRT
<213> ORGANISM: Canis familiaris

<400> SEQUENCE: 4

Leu Asp Ser Pro Asp Arg Pro Trp Ser Pro Leu Thr Phe Ser Pro Ala
1               5                   10                  15

Gln Leu Thr Val Gln Glu Gly Glu Asn Ala Thr Phe Thr Cys Ser Leu
            20                  25                  30

Ala Asp Ile Pro Asp Ser Phe Val Leu Asn Trp Tyr Arg Leu Ser Pro
        35                  40                  45

Arg Asn Gln Thr Asp Lys Leu Ala Ala Phe Gln Glu Asp Arg Ile Glu
    50                  55                  60

Pro Gly Arg Asp Arg Arg Phe Arg Val Met Arg Leu Pro Asn Gly Arg
65                  70                  75                  80

Asp Phe His Met Ser Ile Val Ala Ala Arg Leu Asn Asp Ser Gly Ile
                85                  90                  95

Tyr Leu Cys Gly Ala Ile Tyr Leu Pro Pro Asn Thr Gln Ile Asn Glu
            100                 105                 110

Ser Pro Arg Ala Glu Leu Ser Val Thr Glu Arg Thr Leu Glu Pro Pro
        115                 120                 125

Thr Gln Ser Pro Ser Pro Pro Arg Leu Ser Gly Gln Leu Gln Gly
    130                 135                 140

Leu Val
145
```

```
<210> SEQ ID NO 5
<211> LENGTH: 1128
<212> TYPE: DNA
<213> ORGANISM: Artificial Sequence
<220> FEATURE:
<223> OTHER INFORMATION: codon optimized

<400> SEQUENCE: 5
ctggattccc ccgacagacc ctggagccct ctcaccttct ccctgcccca gctgaccgtc      60
caggaaggcg agaatgccac cttcacctgc agcctcgccg acatcccga cagcttcgtg      120 ctgaactggt acagactgag ccccaggaac cagaccgaca agctggccgc tttccaggag     180
gacaggatcg aacccggcag ggacaggagg tttagggtca tgaggctgcc caacggcagg    240
gacttccaca tgtccatcgt ggccgccaga ctgaacgact ccggcatcta cctgtgcggc     300
gctatctacc tgcccccaa cacccagatc aacgagagcc cagggccga actgagcgtg      360 acagagagaa ccctggaacc tcccacccag agcccttccc ctcctcctag actgagcgga    420
cagctgcagg gcctggtggg taccgacaaa actcacacat gcccaccgtg cccagcacct    480
gaactcctgg ggggaccgtc agtcttcctc ttccccccaa aacccaagga caccctcatg    540
atctcccgga cccctgaggt cacatgcgtg gtggtggacg tgagccacga agaccctgag    600
```

```
gtcaagttca actggtacgt ggacggcgtg gaggtgcata atgccaagac aaagccgcgg    660
gaggagcagt acaacagcac gtaccgtgtg gtcagcgtcc tcaccgtcct gcaccaggac    720
tggctgaatg gcaaggagta caagtgcaag gtctccaaca agcccctccc agcccccatc    780
gagaaaacca tctccaaagc caagggcag ccccgagaac acaggtgta cacccctgccc    840 ccatcccggg atgagctgac caagaaccag gtcagcctga cctgcctggt caaaggcttc    900
tatcccagcg acatcgccgt ggagtgggag agcaatgggc agccggagaa caactacaag    960
accacgcctc ccgtgctgga ctccgacggc tccttcttcc tctacagcaa gctcaccgtg   1020
gacaagagca ggtggcagca ggggaacgtc ttctcatgct ccgtgatgca tgaggctctg   1080
cacaaccact acacgcagaa gagcctctcc ctgtctccgg gtaaatga                1128
```

<210> SEQ ID NO 6
<211> LENGTH: 375
<212> TYPE: PRT
<213> ORGANISM: Artificial Sequence
<220> FEATURE:
<223> OTHER INFORMATION: canine and human

<400> SEQUENCE: 6

```
Leu Asp Ser Pro Asp Arg Pro Trp Ser Pro Leu Thr Phe Ser Pro Ala
1               5                   10                  15

Gln Leu Thr Val Gln Glu Gly Glu Asn Ala Thr Phe Thr Cys Ser Leu
            20                  25                  30

Ala Asp Ile Pro Asp Ser Phe Val Leu Asn Trp Tyr Arg Leu Ser Pro
        35                  40                  45

Arg Asn Gln Thr Asp Lys Leu Ala Ala Phe Gln Glu Asp Arg Ile Glu
    50                  55                  60

Pro Gly Arg Asp Arg Arg Phe Arg Val Met Arg Leu Pro Asn Gly Arg
65                  70                  75                  80

Asp Phe His Met Ser Ile Val Ala Ala Arg Leu Asn Asp Ser Gly Ile
                85                  90                  95

Tyr Leu Cys Gly Ala Ile Tyr Leu Pro Pro Asn Thr Gln Ile Asn Glu
            100                 105                 110

Ser Pro Arg Ala Glu Leu Ser Val Thr Glu Arg Thr Leu Glu Pro Pro
        115                 120                 125

Thr Gln Ser Pro Ser Pro Pro Arg Leu Ser Gly Gln Leu Gln Gly
    130                 135                 140

Leu Val Gly Thr Asp Lys Thr His Thr Cys Pro Pro Cys Pro Ala Pro
145                 150                 155                 160

Glu Leu Leu Gly Gly Pro Ser Val Phe Leu Phe Pro Pro Lys Pro Lys
                165                 170                 175

Asp Thr Leu Met Ile Ser Arg Thr Pro Glu Val Thr Cys Val Val Val
            180                 185                 190

Asp Val Ser His Glu Asp Pro Glu Val Lys Phe Asn Trp Tyr Val Asp
        195                 200                 205

Gly Val Glu Val His Asn Ala Lys Thr Lys Pro Arg Glu Glu Gln Tyr
    210                 215                 220

Asn Ser Thr Tyr Arg Val Val Ser Val Leu Thr Val Leu His Gln Asp
225                 230                 235                 240

Trp Leu Asn Gly Lys Glu Tyr Lys Cys Lys Val Ser Asn Lys Ala Leu
                245                 250                 255

Pro Ala Pro Ile Glu Lys Thr Ile Ser Lys Ala Lys Gly Gln Pro Arg
            260                 265                 270
```

```
Glu Pro Gln Val Tyr Thr Leu Pro Ser Arg Asp Glu Leu Thr Lys
                275                 280                 285

Asn Gln Val Ser Leu Thr Cys Leu Val Lys Gly Phe Tyr Pro Ser Asp
            290                 295                 300

Ile Ala Val Glu Trp Glu Ser Asn Gly Gln Pro Glu Asn Asn Tyr Lys
305                 310                 315                 320

Thr Thr Pro Pro Val Leu Asp Ser Asp Gly Ser Phe Leu Tyr Ser
                325                 330                 335

Lys Leu Thr Val Asp Lys Ser Arg Trp Gln Gln Gly Asn Val Phe Ser
                340                 345                 350

Cys Ser Val Met His Glu Ala Leu His Asn His Tyr Thr Gln Lys Ser
            355                 360                 365

Leu Ser Leu Ser Pro Gly Lys
        370                 375

<210> SEQ ID NO 7
<211> LENGTH: 816
<212> TYPE: DNA
<213> ORGANISM: Canis familiaris

<400> SEQUENCE: 7
tttacgatca cagtttctaa ggacctgtat gtggtagagt atggtggcaa tgtgacaatg      60
gaatgcaaat tcccggtgga aaaacagtta aacttgtttg cactaatcgt ctactgggaa     120
atggaggata aaaaaattat acaatttgtg aatggaaagg aagacctgaa agttcagcac     180
agcagctaca gccagagggc tcagctattg aaggaccagc tcttcttggg aaggctgcg      240 cttcagatca cagatgtgag attgcaggat gcaggggttt actgctgctt gatcggctat     300
ggcggtgctg actacaagcg gattactttg aaagttcatg ccccgtaccg caacatcagc     360
caaagaattt ctgtggatcc tgtcacctct gaacatgaac taatgtgtca ggctgagggt     420
taccctgagg ctgaagtcat ctggacaagc agtgaccacc gagtcctgag tgcaaaaacc     480
accatcacta attccaatag ggaagagaag ctttttcaatg tgaccagcac gctgaacatc     540
aatgcaacag ctaatgagat tttctactgc acttttcaaa gatcaggtcc tgaggaaaac     600
aatactgccg agttggtcat cccagaacga ctgcccgttc agcaagtga gaggactcat      660 ttcatgattc tgggacctt cctgttgctt cttggtgtag tcctggcagt cactttctgt      720
ctaaaaaaac atgggagaat gatggatgtg gaaaaatgtt gcacccgaga taggaactca     780
aagaaacgaa atgatataca atttgaagag acataa                                816

<210> SEQ ID NO 8
<211> LENGTH: 271
<212> TYPE: PRT
<213> ORGANISM: Canis familiaris

<400> SEQUENCE: 8

Phe Thr Ile Thr Val Ser Lys Asp Leu Tyr Val Val Glu Tyr Gly Gly
1               5                   10                  15

Asn Val Thr Met Glu Cys Lys Phe Pro Val Glu Lys Gln Leu Asn Leu
            20                  25                  30

Phe Ala Leu Ile Val Tyr Trp Glu Met Glu Asp Lys Lys Ile Ile Gln
        35                  40                  45

Phe Val Asn Gly Lys Glu Asp Leu Lys Val Gln His Ser Ser Tyr Ser
    50                  55                  60

Gln Arg Ala Gln Leu Leu Lys Asp Gln Leu Phe Leu Gly Lys Ala Ala
65                  70                  75                  80
```

```
Leu Gln Ile Thr Asp Val Arg Leu Gln Asp Ala Gly Val Tyr Cys Cys
                85                  90                  95

Leu Ile Gly Tyr Gly Gly Ala Asp Tyr Lys Arg Ile Thr Leu Lys Val
            100                 105                 110

His Ala Pro Tyr Arg Asn Ile Ser Gln Arg Ile Ser Val Asp Pro Val
        115                 120                 125

Thr Ser Glu His Glu Leu Met Cys Gln Ala Glu Gly Tyr Pro Glu Ala
    130                 135                 140

Glu Val Ile Trp Thr Ser Ser Asp His Arg Val Leu Ser Gly Lys Thr
145                 150                 155                 160

Thr Ile Thr Asn Ser Asn Arg Glu Glu Lys Leu Phe Asn Val Thr Ser
                165                 170                 175

Thr Leu Asn Ile Asn Ala Thr Ala Asn Glu Ile Phe Tyr Cys Thr Phe
            180                 185                 190

Gln Arg Ser Gly Pro Glu Glu Asn Asn Thr Ala Glu Leu Val Ile Pro
        195                 200                 205

Glu Arg Leu Pro Val Pro Ala Ser Glu Arg Thr His Phe Met Ile Leu
    210                 215                 220

Gly Pro Phe Leu Leu Leu Leu Gly Val Val Leu Ala Val Thr Phe Cys
225                 230                 235                 240

Leu Lys Lys His Gly Arg Met Met Asp Val Glu Lys Cys Cys Thr Arg
                245                 250                 255

Asp Arg Asn Ser Lys Lys Arg Asn Asp Ile Gln Phe Glu Glu Thr
            260                 265                 270

<210> SEQ ID NO 9
<211> LENGTH: 660
<212> TYPE: DNA
<213> ORGANISM: Artificial Sequence
<220> FEATURE:
<223> OTHER INFORMATION: codon optimized

<400> SEQUENCE: 9
tttaccatca ccgtgtccaa ggacctgtac gtggtcgagt acggcggcaa tgtgaccatg      60
gagtgcaagt tccccgtgga gaagcagctg aacctgttcg ccctcatcgt gtactgggag     120
atggaggaca gaagatcat ccagttcgtg aacggcaagg aggacctgaa ggtgcagcac     180
tccagctact cccagagagc ccagctgctg aaggaccagc tgttcctggg caaggccgcc     240
ctgcagatca ccgacgtgag actgcaggac gccggcgtgt attgctgcct gatcggctac     300
ggaggcgccg actacaagag gatcaccctg aaggtgcatg cacccctacag gaacatcagc     360
cagaggatca gcgtcgatcc cgtgaccagc gagcacgagc tgatgtgcca gccgagggc     420
tatcccgagg ccgaagtgat ctggaccagc agcgaccaca gggtcctgag cggcaagacc     480
accatcacca cagcaacag ggaggagaag ctgttcaacg tgaccagcac cctcaacatc     540
aacgccaccg ccaacgagat cttctactgc accttccaga ggagcggccc cgaagagaac     600
aacaccgccg agctggtgat ccccgagaga ctgcctgtgc ctgccagcga gaggacccac     660

<210> SEQ ID NO 10
<211> LENGTH: 220
<212> TYPE: PRT
<213> ORGANISM: Canis familiaris

<400> SEQUENCE: 10

Phe Thr Ile Thr Val Ser Lys Asp Leu Tyr Val Val Glu Tyr Gly Gly
1               5                   10                  15
```

```
Asn Val Thr Met Glu Cys Lys Phe Pro Val Glu Lys Gln Leu Asn Leu
             20                  25                  30

Phe Ala Leu Ile Val Tyr Trp Glu Met Glu Asp Lys Lys Ile Ile Gln
         35                  40                  45

Phe Val Asn Gly Lys Glu Asp Leu Lys Val Gln His Ser Ser Tyr Ser
 50                  55                  60

Gln Arg Ala Gln Leu Leu Lys Asp Gln Leu Phe Leu Gly Lys Ala Ala
 65                  70                  75                  80

Leu Gln Ile Thr Asp Val Arg Leu Gln Asp Ala Gly Val Tyr Cys Cys
                 85                  90                  95

Leu Ile Gly Tyr Gly Gly Ala Asp Tyr Lys Arg Ile Thr Leu Lys Val
            100                 105                 110

His Ala Pro Tyr Arg Asn Ile Ser Gln Arg Ile Ser Val Asp Pro Val
        115                 120                 125

Thr Ser Glu His Glu Leu Met Cys Gln Ala Glu Gly Tyr Pro Glu Ala
130                 135                 140

Glu Val Ile Trp Thr Ser Ser Asp His Arg Val Leu Ser Gly Lys Thr
145                 150                 155                 160

Thr Ile Thr Asn Ser Asn Arg Glu Glu Lys Leu Phe Asn Val Thr Ser
                165                 170                 175

Thr Leu Asn Ile Asn Ala Thr Ala Asn Glu Ile Phe Tyr Cys Thr Phe
            180                 185                 190

Gln Arg Ser Gly Pro Glu Glu Asn Asn Thr Ala Glu Leu Val Ile Pro
        195                 200                 205

Glu Arg Leu Pro Val Pro Ala Ser Glu Arg Thr His
    210                 215                 220

<210> SEQ ID NO 11
<211> LENGTH: 1350
<212> TYPE: DNA
<213> ORGANISM: Artificial Sequence
<220> FEATURE:
<223> OTHER INFORMATION: codon optimized

<400> SEQUENCE: 11
tttaccatca ccgtgtccaa ggacctgtac gtggtcgagt acggcggcaa tgtgaccatg      60
gagtgcaagt tccccgtgga gaagcagctg aacctgttcg ccctcatcgt gtactgggag     120
atggaggaca agaagatcat ccagttcgtg aacggcaagg aggacctgaa ggtgcagcac     180
tccagctact cccagagagc ccagctgctg aaggaccagc tgttcctggg caaggccgcc     240
ctgcagatca ccgacgtgag actgcaggac gccggcgtgt attgctgcct gatcggctac     300
ggaggcgccg actacaagag gatcaccctg aaggtgcatg cccctacag gaacatcagc      360 cagaggatca gcgtcgatcc cgtgaccagc gagcacgagc tgatgtgcca agccgagggc     420
tatcccgagg ccgaagtgat ctggaccagc agcgaccaca gggtcctgag cggcaagacc     480
accatcacca cagcaacag ggaggagaag ctgttcaacg tgaccagcac cctcaacatc      540
aacgccaccg ccaacgagat cttctactgc accttccaga ggagcggccc cgaagagaac     600
aacaccgccg agctggtgat ccccgagaga ctgcctgtgc ctgccagcga gaggacccac     660
ggtaccgaca aaactcacac atgcccaccg tgcccagcac ctgaactcct ggggggaccg     720
tcagtcttcc tcttcccccc aaaacccaag gacaccctca tgatctcccg gacccctgag     780
gtcacatgcg tggtggtgga cgtgagccac gaagaccctg aggtcaagtt caactggtac     840
gtggacggcg tggaggtgca taatgccaag acaaagccgc gggaggagca gtacaacagc     900
```

```
acgtaccgtg tggtcagcgt cctcaccgtc ctgcaccagg actggctgaa tggcaaggag    960
tacaagtgca aggtctccaa caaagccctc ccagccccca tcgagaaaac catctccaaa   1020
gccaaagggc agccccgaga accacaggtg tacaccctgc ccccatcccg ggatgagctg   1080
accaagaacc aggtcagcct gacctgcctg gtcaaaggct tctatcccag cgacatcgcc   1140
gtggagtggg agagcaatgg gcagccggag aacaactaca agaccacgcc tcccgtgctg   1200
gactccgacg gctccttctt cctctacagc aagctcaccg tggacaagag caggtggcag   1260
caggggaacg tcttctcatg ctccgtgatg catgaggctc tgcacaacca ctacacgcag   1320
aagagcctct ccctgtctcc gggtaaatga                                   1350
```

<210> SEQ ID NO 12
<211> LENGTH: 449
<212> TYPE: PRT
<213> ORGANISM: Canis familiaris

<400> SEQUENCE: 12

```
Phe Thr Ile Thr Val Ser Lys Asp Leu Tyr Val Val Glu Tyr Gly Gly
 1               5                  10                  15

Asn Val Thr Met Glu Cys Lys Phe Pro Val Glu Lys Gln Leu Asn Leu
             20                  25                  30

Phe Ala Leu Ile Val Tyr Trp Glu Met Glu Asp Lys Lys Ile Ile Gln
         35                  40                  45

Phe Val Asn Gly Lys Glu Asp Leu Lys Val Gln His Ser Ser Tyr Ser
     50                  55                  60

Gln Arg Ala Gln Leu Leu Lys Asp Gln Leu Phe Leu Gly Lys Ala Ala
 65                  70                  75                  80

Leu Gln Ile Thr Asp Val Arg Leu Gln Asp Ala Gly Val Tyr Cys Cys
                 85                  90                  95

Leu Ile Gly Tyr Gly Gly Ala Asp Tyr Lys Arg Ile Thr Leu Lys Val
            100                 105                 110

His Ala Pro Tyr Arg Asn Ile Ser Gln Arg Ile Ser Val Asp Pro Val
        115                 120                 125

Thr Ser Glu His Glu Leu Met Cys Gln Ala Glu Gly Tyr Pro Glu Ala
    130                 135                 140

Glu Val Ile Trp Thr Ser Ser Asp His Arg Val Leu Ser Gly Lys Thr
145                 150                 155                 160

Thr Ile Thr Asn Ser Asn Arg Glu Glu Lys Leu Phe Asn Val Thr Ser
                165                 170                 175

Thr Leu Asn Ile Asn Ala Thr Ala Asn Glu Ile Phe Tyr Cys Thr Phe
            180                 185                 190

Gln Arg Ser Gly Pro Glu Glu Asn Asn Thr Ala Glu Leu Val Ile Pro
        195                 200                 205

Glu Arg Leu Pro Val Pro Ala Ser Glu Arg Thr His Gly Thr Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285
```

```
Ala Lys Thr Lys Pro Arg Glu Glu Gln Tyr Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Asp Glu Leu Thr Lys Asn Gln Val Ser Leu Thr
        355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
                420                 425                 430
Ala Leu His Asn His Tyr Thr Gln Lys Ser Leu Ser Leu Ser Pro Gly
        435                 440                 445
Lys

<210> SEQ ID NO 13
<211> LENGTH: 15
<212> TYPE: DNA
<213> ORGANISM: Mus musculus

<400> SEQUENCE: 13
agttattatc tgtac                                                      15

<210> SEQ ID NO 14
<211> LENGTH: 5
<212> TYPE: PRT
<213> ORGANISM: Mus musculus

<400> SEQUENCE: 14

Ser Tyr Tyr Leu Tyr
1               5

<210> SEQ ID NO 15
<211> LENGTH: 48
<212> TYPE: DNA
<213> ORGANISM: Mus musculus

<400> SEQUENCE: 15
ggggttaatc ctagtaatgg tggtactaac ttcagtgaga agttcaag                  48

<210> SEQ ID NO 16
<211> LENGTH: 16
<212> TYPE: PRT
<213> ORGANISM: Mus musculus

<400> SEQUENCE: 16

Gly Val Asn Pro Ser Asn Gly Gly Thr Asn Phe Ser Glu Lys Phe Lys
1               5                   10                  15

<210> SEQ ID NO 17
<211> LENGTH: 33
<212> TYPE: DNA
<213> ORGANISM: Mus musculus
```

```
<400> SEQUENCE: 17
agggattcta actacgacgg gggctttgac tac                          33

<210> SEQ ID NO 18
<211> LENGTH: 11
<212> TYPE: PRT
<213> ORGANISM: Mus musculus

<400> SEQUENCE: 18

Arg Asp Ser Asn Tyr Asp Gly Gly Phe Asp Tyr
1               5                   10

<210> SEQ ID NO 19
<211> LENGTH: 45
<212> TYPE: DNA
<213> ORGANISM: Mus musculus

<400> SEQUENCE: 19
agggccagca aaagtgtcag tacatctggc tttagttatt tgcac            45

<210> SEQ ID NO 20
<211> LENGTH: 15
<212> TYPE: PRT
<213> ORGANISM: Mus musculus

<400> SEQUENCE: 20

Arg Ala Ser Lys Ser Val Ser Thr Ser Gly Phe Ser Tyr Leu His
1               5                   10                  15

<210> SEQ ID NO 21
<211> LENGTH: 21
<212> TYPE: DNA
<213> ORGANISM: Mus musculus

<400> SEQUENCE: 21
cttgcatcca acctagagtc t                                      21

<210> SEQ ID NO 22
<211> LENGTH: 7
<212> TYPE: PRT
<213> ORGANISM: Mus musculus

<400> SEQUENCE: 22

Leu Ala Ser Asn Leu Glu Ser
1               5

<210> SEQ ID NO 23
<211> LENGTH: 27
<212> TYPE: DNA
<213> ORGANISM: Mus musculus

<400> SEQUENCE: 23
cagcacagtt gggagcttcc gctcacg                                27

<210> SEQ ID NO 24
<211> LENGTH: 9
<212> TYPE: PRT
<213> ORGANISM: Mus musculus

<400> SEQUENCE: 24

Gln His Ser Trp Glu Leu Pro Leu Thr
1               5
```

<210> SEQ ID NO 25
<211> LENGTH: 1353
<212> TYPE: DNA
<213> ORGANISM: Artificial Sequence
<220> FEATURE:
<223> OTHER INFORMATION: caninized mouse antibody

<400> SEQUENCE: 25

```
gaggtgcagc tggtgcagtc cggcggcgat ctggtgaagc tggaggcag cgtgagactg      60
agctgcgtgg ccagcggcta caccttcacc agctactacc tgtactgggt gaggcaggct     120
cctggcaaag gactgcagtg gatcggcggc gtgaatccta gcaacggcgg caccaacttc     180
agcgagaagt tcaagagcag ggccaccctg agcgtggaca aggccaagaa caccgcctac     240
atgcagctga actccctgag ggccgaggac accgccgtgt actactgcac caggagggac     300
agcaactacg acggcggctt cgactactgg ggacaggaa ccctgctgac cgtgtccagc      360
gcttccacaa cggctccgtc ggtgtttccc ctggcaccta gctgcgggtc gacctcgggt     420
agcacagtgg cgctggcgtg tttggtgtcg ggatactttc ccgagccggt aacggtgtca     480
tggaactcag ggtcacttac atcaggagtc catactttc cgtccgtgct gcagtcaagc      540
ggcttgcatt cactgtcctc gatggtgacg gtgccttcgt cgaggtggcc cagcgaaacg     600
ttcacttgta acgtagtaca cccggcctcc aacacgaaag tcgataaacc ggtattcaat     660
gagtgcagat gtacagacac ccctcccgt ccggtacccg aacccttgg agggccgagc      720
gtcctcatct ccctcccaa gccaaaagac atcttgcgca ttacgaggac accagaagtc     780
acgtgcgtag tgcttgatct cggtagagaa gatcccgagg tccagatctc gtggtttgtg     840
gatggaaagg aggtccacac cgcaaagact cagtcgcgcg agcagcagtt caatggcacg     900
tatcgggtcg tgagcgtgct tcctatcgag catcaggact ggctcaccgg gaaggagttc     960
aaatgccggg tcaatcatat cgacctcccg tcaccaatcg agcggaccat ctcgaaggct    1020
agaggaaggg cgcacaaacc ttcggtctat gtgcttcccc catcgcccaa agagctttcc    1080
tcgtcggata cggtgtccat tacatgcttg attaaggact ctatcctcc tgatattgat     1140
gtggaatggc aatcaaacgg acagcaggag ccggaacgca agcaccgaat gacccccaccg  1200
caattggacg aagatggtag ctactttctc tactcaaagc tctcagtcga caaatcccga    1260
tgcagcagg gagatccctt cacttgcgcc gtgatgcacg agacactcca aaatcattac     1320
acggaccttt cgttgagcca ctcgcccgga aag                                 1353
```

<210> SEQ ID NO 26
<211> LENGTH: 451
<212> TYPE: PRT
<213> ORGANISM: Artificial Sequence
<220> FEATURE:
<223> OTHER INFORMATION: caninized mouse antibody

<400> SEQUENCE: 26

```
Glu Val Gln Leu Val Gln Ser Gly Gly Asp Leu Val Lys Pro Gly Gly
1               5                   10                  15

Ser Val Arg Leu Ser Cys Val Ala Ser Gly Tyr Thr Phe Thr Ser Tyr
            20                  25                  30

Tyr Leu Tyr Trp Val Arg Gln Ala Pro Gly Lys Gly Leu Gln Trp Ile
        35                  40                  45

Gly Gly Val Asn Pro Ser Asn Gly Gly Thr Asn Phe Ser Glu Lys Phe
    50                  55                  60

Lys Ser Arg Ala Thr Leu Ser Val Asp Lys Ala Lys Asn Thr Ala Tyr
```

```
            65                  70                  75                  80
        Met Gln Leu Asn Ser Leu Arg Ala Glu Asp Thr Ala Val Tyr Tyr Cys
                            85                  90                  95

Thr Arg Arg Asp Ser Asn Tyr Asp Gly Gly Phe Asp Tyr Trp Gly Gln
                        100                 105                 110

Gly Thr Leu Leu Thr Val Ser Ala Ser Thr Thr Ala Pro Ser Val
                    115                 120                 125

Phe Pro Leu Ala Pro Ser Cys Gly Ser Thr Ser Gly Ser Thr Val Ala
            130                 135                 140

Leu Ala Cys Leu Val Ser Gly Tyr Phe Pro Glu Pro Val Thr Val Ser
        145                 150                 155                 160

Trp Asn Ser Gly Ser Leu Thr Ser Gly Val His Thr Phe Pro Ser Val
                        165                 170                 175

Leu Gln Ser Ser Gly Leu His Ser Leu Ser Ser Met Val Thr Val Pro
                    180                 185                 190

Ser Ser Arg Trp Pro Ser Glu Thr Phe Thr Cys Asn Val Val His Pro
                195                 200                 205

Ala Ser Asn Thr Lys Val Asp Lys Pro Val Phe Asn Glu Cys Arg Cys
            210                 215                 220

Thr Asp Thr Pro Pro Cys Pro Val Pro Glu Pro Leu Gly Gly Pro Ser
        225                 230                 235                 240

Val Leu Ile Phe Pro Pro Lys Pro Lys Asp Ile Leu Arg Ile Thr Arg
                        245                 250                 255

Thr Pro Glu Val Thr Cys Val Val Leu Asp Leu Gly Arg Glu Asp Pro
                    260                 265                 270

Glu Val Gln Ile Ser Trp Phe Val Asp Gly Lys Glu Val His Thr Ala
                275                 280                 285

Lys Thr Gln Ser Arg Glu Gln Gln Phe Asn Gly Thr Tyr Arg Val Val
            290                 295                 300

Ser Val Leu Pro Ile Glu His Gln Asp Trp Leu Thr Gly Lys Glu Phe
        305                 310                 315                 320

Lys Cys Arg Val Asn His Ile Asp Leu Pro Ser Pro Ile Glu Arg Thr
                        325                 330                 335

Ile Ser Lys Ala Arg Gly Arg Ala His Lys Pro Ser Val Tyr Val Leu
                    340                 345                 350

Pro Pro Ser Pro Lys Glu Leu Ser Ser Asp Thr Val Ser Ile Thr
                355                 360                 365

Cys Leu Ile Lys Asp Phe Tyr Pro Pro Asp Ile Asp Val Glu Trp Gln
            370                 375                 380

Ser Asn Gly Gln Gln Glu Pro Glu Arg Lys His Arg Met Thr Pro Pro
        385                 390                 395                 400

Gln Leu Asp Glu Asp Gly Ser Tyr Phe Leu Tyr Ser Lys Leu Ser Val
                        405                 410                 415

Asp Lys Ser Arg Trp Gln Gln Gly Asp Pro Phe Thr Cys Ala Val Met
                    420                 425                 430

His Glu Thr Leu Gln Asn His Tyr Thr Asp Leu Ser Leu Ser His Ser
                435                 440                 445

Pro Gly Lys
            450

<210> SEQ ID NO 27
<211> LENGTH: 1368
<212> TYPE: DNA
<213> ORGANISM: Artificial Sequence
```

```
<220> FEATURE:
<223> OTHER INFORMATION: caninized mouse antibody

<400> SEQUENCE: 27
gaggtgcagc tggtgcagtc cggcggcgat ctggtgaagc ctggaggcag cgtgagactg      60
agctgcgtgg ccagcggcta caccttcacc agctactacc tgtactgggt gaggcaggct     120
cctggcaaag gactgcagtg gatcggcggc gtgaatccta gcaacggcgg caccaacttc     180
agcgagaagt tcaagagcag ggccaccctg agcgtggaca aggccaagaa caccgcctac     240
atgcagctga actccctgag ggccgaggac accgccgtgt actactgcac caggagggac     300
agcaactacg acgcggcttc gactactggg gacagggaa ccctgctgac cgtgtccagc      360
gcttccacaa ccgcgccatc agtctttccg ttggccccat catgcgggtc gacgagcgga     420
tcgactgtgg ccctggcgtg cttggtgtcg ggatactttc ccgaacccgt cacggtcagc     480
tggaactccg gatcgcttac gagcggtgtg catacgttcc cctcggtctt gcaatcatca     540
gggctctact cgctgtcgag catggtaacg gtgccctcat cgaggtggcc ctccgaaacg     600
ttcacatgta acgtagcaca tccagcctcc aaaaccaagg tggataaacc cgtgccgaaa     660
agagagaatg ggcgggtgcc tcgaccccct gattgcccca agtgtccggc tccgaaaatg     720
ctcggtggac cctcagtgtt tatcttccct ccgaagccca aggacactct gctgatcgcg     780
cgcactccag aagtaacatg tgtagtggtg gaccttgatc ccgaggaccc cgaagtccag     840
atctcctggt ttgtagatgg gaaacagatg cagaccgcaa aaactcaacc cagagaggag     900
cagttcaacg gaacataccg agtggtatcc gtccttccga ttggccacca ggactggttg     960
aaagggaagc agtttacgtg taaagtcaac aataaggcgt tgcctagccc tattgagcgg    1020
acgatttcga aagctagggg acaggcccac cagccatcgg tctatgtcct tccgccttcc    1080
cgcgaggagc tctcgaagaa tacagtgagc cttacatgcc tcattaagga tttcttcccg    1140
cctgatatcg acgtagagtg gcaatcaaac ggtcaacagg agccggaatc caagtataga    1200
accactccgc cccagcttga cgaggacgga tcatactttt tgtattcaaa actgtcggtg    1260
gataagagcc ggtggcagag aggtgacacc ttcatctgtg cggtgatgca cgaagcactc    1320
cataatcact acacccaaga gagcctctcg cattcccccg gaaagtga                 1368

<210> SEQ ID NO 28
<211> LENGTH: 455
<212> TYPE: PRT
<213> ORGANISM: Artificial Sequence
<220> FEATURE:
<223> OTHER INFORMATION: caninized mouse antibody

<400> SEQUENCE: 28

Glu Val Gln Leu Val Gln Ser Gly Gly Asp Leu Val Lys Pro Gly Gly
1               5                   10                  15

Ser Val Arg Leu Ser Cys Val Ala Ser Gly Tyr Thr Phe Thr Ser Tyr
            20                  25                  30

Tyr Leu Tyr Trp Val Arg Gln Ala Pro Gly Lys Gly Leu Gln Trp Ile
        35                  40                  45

Gly Gly Val Asn Pro Ser Asn Gly Gly Thr Asn Phe Ser Glu Lys Phe
    50                  55                  60

Lys Ser Arg Ala Thr Leu Ser Val Asp Lys Ala Lys Asn Thr Ala Tyr
65                  70                  75                  80

Met Gln Leu Asn Ser Leu Arg Ala Glu Asp Thr Ala Val Tyr Tyr Cys
                85                  90                  95
```

```
Thr Arg Arg Asp Ser Asn Tyr Asp Gly Gly Phe Asp Tyr Trp Gly Gln
            100                 105                 110

Gly Thr Leu Leu Thr Val Ser Ser Ala Ser Thr Thr Ala Pro Ser Val
        115                 120                 125

Phe Pro Leu Ala Pro Ser Cys Gly Ser Thr Ser Gly Ser Thr Val Ala
    130                 135                 140

Leu Ala Cys Leu Val Ser Gly Tyr Phe Pro Glu Pro Val Thr Val Ser
145                 150                 155                 160

Trp Asn Ser Gly Ser Leu Thr Ser Gly Val His Thr Phe Pro Ser Val
                165                 170                 175

Leu Gln Ser Ser Gly Leu Tyr Ser Leu Ser Ser Met Val Thr Val Pro
            180                 185                 190

Ser Ser Arg Trp Pro Ser Glu Thr Phe Thr Cys Asn Val Ala His Pro
        195                 200                 205

Ala Ser Lys Thr Lys Val Asp Lys Pro Val Pro Lys Arg Glu Asn Gly
    210                 215                 220

Arg Val Pro Arg Pro Pro Asp Cys Pro Lys Cys Pro Ala Pro Glu Met
225                 230                 235                 240

Leu Gly Gly Pro Ser Val Phe Ile Phe Pro Pro Lys Pro Lys Asp Thr
                245                 250                 255

Leu Leu Ile Ala Arg Thr Pro Glu Val Thr Cys Val Val Val Asp Leu
            260                 265                 270

Asp Pro Glu Asp Pro Glu Val Gln Ile Ser Trp Phe Val Asp Gly Lys
        275                 280                 285

Gln Met Gln Thr Ala Lys Thr Gln Pro Arg Glu Glu Gln Phe Asn Gly
    290                 295                 300

Thr Tyr Arg Val Val Ser Val Leu Pro Ile Gly His Gln Asp Trp Leu
305                 310                 315                 320

Lys Gly Lys Gln Phe Thr Cys Lys Val Asn Asn Lys Ala Leu Pro Ser
                325                 330                 335

Pro Ile Glu Arg Thr Ile Ser Lys Ala Arg Gly Gln Ala His Gln Pro
            340                 345                 350

Ser Val Tyr Val Leu Pro Pro Ser Arg Glu Glu Leu Ser Lys Asn Thr
        355                 360                 365

Val Ser Leu Thr Cys Leu Ile Lys Asp Phe Phe Pro Pro Asp Ile Asp
    370                 375                 380

Val Glu Trp Gln Ser Asn Gly Gln Gln Glu Pro Glu Ser Lys Tyr Arg
385                 390                 395                 400

Thr Thr Pro Pro Gln Leu Asp Glu Asp Gly Ser Tyr Phe Leu Tyr Ser
                405                 410                 415

Lys Leu Ser Val Asp Lys Ser Arg Trp Gln Arg Gly Asp Thr Phe Ile
            420                 425                 430

Cys Ala Val Met His Glu Ala Leu His Asn His Tyr Thr Gln Glu Ser
        435                 440                 445

Leu Ser His Ser Pro Gly Lys
    450                 455

<210> SEQ ID NO 29
<211> LENGTH: 1353
<212> TYPE: DNA
<213> ORGANISM: Artificial Sequence
<220> FEATURE:
<223> OTHER INFORMATION: caninized mouse antibody

<400> SEQUENCE: 29
```

```
gaggtgcagc tggtgcagtc cggcggcgat ctggtgaagc tggaggcag cgtgagactg       60
agctgcgtgg ccagcggcta caccttcacc agctactacc tgtactgggt gaggcaggct      120
cctggcaaag gactgcagtg gatcggcggc gtgaatccta gcaacggcgg caccaacttc      180
agcgagaagt tcaagagcag ggccaccctg agcgtggaca aggccaagaa caccgcctac      240
atgcagctga actccctgag ggccgaggac accgccgtgt actactgcac caggagggac      300
agcaactacg acggcggctt cgactactgg ggacagggaa ccctgctgac cgtgtccagc      360
gcttcaacca cagcgccgag cgtgttccct ctggcgccgt cgtgcggttc cacctcggga      420
tcaacagtgg ccctcgcctg tctcgtgagc ggatactttc cggagcctgt cacggtgtcg      480
tggaatagcg gatcactcac gtcgggcgtg catactttc catccgtctt gcaatcgagc       540
ggattgtact cactctcctc aaccgtcact gtcccctcgt cgcgctggcc ctcggagact       600
tttacgtgca atgtagtcca tccggcgagc aacacgaagg tcgacaagcc cgtacccaag      660
gaatcaacat gcaagtgcat ctcgccctgt cccgtcccg aatcccttgg tggcccctca       720
gtgtttatct tccctccgaa gcctaaagac atcttgagaa tcacaagaac accgaaaatc      780
acgtgtgtgg tccttgactt gggacgcgag gaccctgagg tacaaatctc gtggtttgtg      840
gacgggaaag aggtgcacac agcaaagaca caaccacgcg agcagcagtt taactcaacg      900
tacagggtag tatccgtact tcccattgaa caccaggatt ggctcaccgg taaagaattc       960
aaatgccgag tgaatcacat cgggcttcct agcccaattg agcggacgat ttccaaagct     1020
aggggtcagg cccaccagcc gagcgtatac gtgttgccgc cctccccgaa ggagctgtca     1080
tcgtcagata cggtaacgtt gacgtgtctg atcaaagatt tctttcctcc cgaaattgat     1140
gtggaatggc aaagcaatgg gcagcccgag cccgagtcaa agtaccatac tactgcacca     1200
cagctggacg aagatggatc gtatttcctc tactcgaaac tgtccgtgga taagtcccgg     1260
tggcagcaag gggacaccct cacttgcgcg gtcatgcacg aggcacttca gaaccactat     1320
acggacttga gcctctcgca ttcgccaggg aag                                  1353
```

<210> SEQ ID NO 30
<211> LENGTH: 451
<212> TYPE: PRT
<213> ORGANISM: Artificial Sequence
<220> FEATURE:
<223> OTHER INFORMATION: caninized mouse antibody

<400> SEQUENCE: 30

Glu Val Gln Leu Val Gln Ser Gly Gly Asp Leu Val Lys Pro Gly Gly
1               5                   10                  15

Ser Val Arg Leu Ser Cys Val Ala Ser Gly Tyr Thr Phe Thr Ser Tyr
            20                  25                  30

Tyr Leu Tyr Trp Val Arg Gln Ala Pro Gly Lys Gly Leu Gln Trp Ile
        35                  40                  45

Gly Gly Val Asn Pro Ser Asn Gly Gly Thr Asn Phe Ser Glu Lys Phe
    50                  55                  60

Lys Ser Arg Ala Thr Leu Ser Val Asp Lys Ala Lys Asn Thr Ala Tyr
65                  70                  75                  80

Met Gln Leu Asn Ser Leu Arg Ala Glu Asp Thr Ala Val Tyr Tyr Cys
                85                  90                  95

Thr Arg Arg Asp Ser Asn Tyr Asp Gly Gly Phe Asp Tyr Trp Gly Gln
            100                 105                 110

Gly Thr Leu Leu Thr Val Ser Ser Ala Ser Thr Thr Ala Pro Ser Val
        115                 120                 125

Phe Pro Leu Ala Pro Ser Cys Gly Ser Thr Ser Gly Ser Thr Val Ala
        130                 135                 140

Leu Ala Cys Leu Val Ser Gly Tyr Phe Pro Glu Pro Val Thr Val Ser
145                 150                 155                 160

Trp Asn Ser Gly Ser Leu Thr Ser Gly Val His Thr Phe Pro Ser Val
                165                 170                 175

Leu Gln Ser Ser Gly Leu Tyr Ser Leu Ser Ser Thr Val Thr Val Pro
            180                 185                 190

Ser Ser Arg Trp Pro Ser Glu Thr Phe Thr Cys Asn Val Val His Pro
        195                 200                 205

Ala Ser Asn Thr Lys Val Asp Lys Pro Val Pro Lys Glu Ser Thr Cys
    210                 215                 220

Lys Cys Ile Ser Pro Cys Pro Val Pro Glu Ser Leu Gly Gly Pro Ser
225                 230                 235                 240

Val Phe Ile Phe Pro Pro Lys Pro Lys Asp Ile Leu Arg Ile Thr Arg
                245                 250                 255

Thr Pro Glu Ile Thr Cys Val Val Leu Asp Leu Gly Arg Glu Asp Pro
            260                 265                 270

Glu Val Gln Ile Ser Trp Phe Val Asp Gly Lys Glu Val His Thr Ala
        275                 280                 285

Lys Thr Gln Pro Arg Glu Gln Gln Phe Asn Ser Thr Tyr Arg Val Val
    290                 295                 300

Ser Val Leu Pro Ile Glu His Gln Asp Trp Leu Thr Gly Lys Glu Phe
305                 310                 315                 320

Lys Cys Arg Val Asn His Ile Gly Leu Pro Ser Pro Ile Glu Arg Thr
                325                 330                 335

Ile Ser Lys Ala Arg Gly Gln Ala His Gln Pro Ser Val Tyr Val Leu
            340                 345                 350

Pro Pro Ser Pro Lys Glu Leu Ser Ser Ser Asp Thr Val Thr Leu Thr
        355                 360                 365

Cys Leu Ile Lys Asp Phe Phe Pro Pro Glu Ile Asp Val Glu Trp Gln
    370                 375                 380

Ser Asn Gly Gln Pro Glu Pro Glu Ser Lys Tyr His Thr Thr Ala Pro
385                 390                 395                 400

Gln Leu Asp Glu Asp Gly Ser Tyr Phe Leu Tyr Ser Lys Leu Ser Val
                405                 410                 415

Asp Lys Ser Arg Trp Gln Gln Gly Asp Thr Phe Thr Cys Ala Val Met
            420                 425                 430

His Glu Ala Leu Gln Asn His Tyr Thr Asp Leu Ser Leu Ser His Ser
        435                 440                 445

Pro Gly Lys
    450

<210> SEQ ID NO 31
<211> LENGTH: 666
<212> TYPE: DNA
<213> ORGANISM: Artificial Sequence
<220> FEATURE:
<223> OTHER INFORMATION: caninized mouse antibody

<400> SEQUENCE: 31
gatatcgtcc tgacccagac ccctctgagc ctgtccgtga gccctggaga acccgccagc    60
atcagctgca gggcctccaa gagcgtgagc cagcggctt tcagctacct gcactggtac    120
aggcagaagc ccggacagag ccctcagctg ctgatcttcc tggccagcaa cctggagagc    180

```
ggcgtgcctg acaggtttag cggaagcggc agcggcaccg acttcacact gaggatctcc    240
agggtggaag ccgacgacgc cggagtgtac tactgccagc acagctggga actgcccctg    300
accttcggcc agggcaccaa ggtggagatc aagaggaacg acgctcagcc agccgtgtac    360
ctcttccagc cttcgccgga ccagcttcat acggggtcag cgtcggtggt gtgcctgttg    420
aactcgtttt accccaagga cattaacgtg aagtggaagg tagacggggt aattcaagac    480
actggcattc aagagtccgt cacgaacaa gactcaaaag actcaacgta ttcactgtcg     540
tcaaccttga cgatgtcaag caccgagtat cttagccatg agctgtattc gtgcgagatc    600
acccacaagt ccctcccctc cactcttatc aaatcctttc agcggtcgga atgtcagcgg    660
gtcgat                                                                666
```

<210> SEQ ID NO 32
<211> LENGTH: 222
<212> TYPE: PRT
<213> ORGANISM: Artificial Sequence
<220> FEATURE:
<223> OTHER INFORMATION: caninized mouse antibody

<400> SEQUENCE: 32

```
Asp Ile Val Leu Thr Gln Thr Pro Leu Ser Leu Ser Val Ser Pro Gly
1               5                   10                  15

Glu Pro Ala Ser Ile Ser Cys Arg Ala Ser Lys Ser Val Ser Thr Ser
            20                  25                  30

Gly Phe Ser Tyr Leu His Trp Tyr Arg Gln Lys Pro Gly Gln Ser Pro
        35                  40                  45

Gln Leu Leu Ile Phe Leu Ala Ser Asn Leu Glu Ser Gly Val Pro Asp
    50                  55                  60

Arg Phe Ser Gly Ser Gly Ser Gly Thr Asp Phe Thr Leu Arg Ile Ser
65                  70                  75                  80

Arg Val Glu Ala Asp Asp Ala Gly Val Tyr Tyr Cys Gln His Ser Trp
                85                  90                  95

Glu Leu Pro Leu Thr Phe Gly Gln Gly Thr Lys Val Glu Ile Lys Arg
            100                 105                 110

Asn Asp Ala Gln Pro Ala Val Tyr Leu Phe Gln Pro Ser Pro Asp Gln
        115                 120                 125

Leu His Thr Gly Ser Ala Ser Val Val Cys Leu Leu Asn Ser Phe Tyr
    130                 135                 140

Pro Lys Asp Ile Asn Val Lys Trp Lys Val Asp Gly Val Ile Gln Asp
145                 150                 155                 160

Thr Gly Ile Gln Glu Ser Val Thr Glu Gln Asp Ser Lys Asp Ser Thr
                165                 170                 175

Tyr Ser Leu Ser Ser Thr Leu Thr Met Ser Ser Thr Glu Tyr Leu Ser
            180                 185                 190

His Glu Leu Tyr Ser Cys Glu Ile Thr His Lys Ser Leu Pro Ser Thr
        195                 200                 205

Leu Ile Lys Ser Phe Gln Arg Ser Glu Cys Gln Arg Val Asp
    210                 215                 220
```

<210> SEQ ID NO 33
<211> LENGTH: 666
<212> TYPE: DNA
<213> ORGANISM: Artificial Sequence
<220> FEATURE:
<223> OTHER INFORMATION: caninized mouse antibody

<400> SEQUENCE: 33

```
gatatcgtcc tgacccagac ccctcctagc ctgtccgtga gccctggaga acccgccagc    60
atcagctgca gggcctccaa gagcgtgagc accagcggct tcagctacct gcactggtac   120
aggcagaagc ccggacagcc tcctcagctg ctgatcttcc tggccagcaa cctggagagc   180
ggcgtgcctg acaggtttag cggaagcggc agcggcaccg acttcacact gaggatctcc   240
agggtggaag ccgacgacgc cggagtgtac tactgccagc acagctggga actgcccctg   300
accttcggcc agggcaccaa ggtggagatc aagaggaacg acgctcagcc agccgtgtac   360
ctcttccagc cttcgccgga ccagcttcat acggggtcag cgtcggtggt gtgcctgttg   420
aactcgtttt accccaagga cattaacgtg aagtggaagg tagacggggt aattcaagac   480
actggcattc aagagtccgt cacggaacaa gactcaaaag actcaacgta ttcactgtcg   540
tcaaccttga cgatgtcaag caccgagtat cttagccatg agctgtattc gtgcgagatc   600
acccacaagt ccctcccctc cactcttatc aaatcctttc agcggtcgga atgtcagcgg   660
gtcgat                                                              666
```

<210> SEQ ID NO 34
<211> LENGTH: 222
<212> TYPE: PRT
<213> ORGANISM: Artificial Sequence
<220> FEATURE:
<223> OTHER INFORMATION: caninized mouse antibody

<400> SEQUENCE: 34

```
Asp Ile Val Leu Thr Gln Thr Pro Ser Leu Ser Val Ser Pro Gly
1               5                   10                  15

Glu Pro Ala Ser Ile Ser Cys Arg Ala Ser Lys Ser Val Ser Thr Ser
            20                  25                  30

Gly Phe Ser Tyr Leu His Trp Tyr Arg Gln Lys Pro Gly Gln Pro Pro
        35                  40                  45

Gln Leu Leu Ile Phe Leu Ala Ser Asn Leu Glu Ser Gly Val Pro Asp
    50                  55                  60

Arg Phe Ser Gly Ser Gly Ser Gly Thr Asp Phe Thr Leu Arg Ile Ser
65                  70                  75                  80

Arg Val Glu Ala Asp Asp Ala Gly Val Tyr Tyr Cys Gln His Ser Trp
                85                  90                  95

Glu Leu Pro Leu Thr Phe Gly Gln Gly Thr Lys Val Glu Ile Lys Arg
            100                 105                 110

Asn Asp Ala Gln Pro Ala Val Tyr Leu Phe Gln Pro Ser Pro Asp Gln
        115                 120                 125

Leu His Thr Gly Ser Ala Ser Val Val Cys Leu Leu Asn Ser Phe Tyr
    130                 135                 140

Pro Lys Asp Ile Asn Val Lys Trp Lys Val Asp Gly Val Ile Gln Asp
145                 150                 155                 160

Thr Gly Ile Gln Glu Ser Val Thr Glu Gln Asp Ser Lys Asp Ser Thr
                165                 170                 175

Tyr Ser Leu Ser Ser Thr Leu Thr Met Ser Ser Thr Glu Tyr Leu Ser
            180                 185                 190

His Glu Leu Tyr Ser Cys Glu Ile Thr His Lys Ser Leu Pro Ser Thr
        195                 200                 205

Leu Ile Lys Ser Phe Gln Arg Ser Glu Cys Gln Arg Val Asp
    210                 215                 220
```

<210> SEQ ID NO 35
<211> LENGTH: 867
<212> TYPE: DNA
<213> ORGANISM: Canis familiaris

<400> SEQUENCE: 35

```
atggggagcc ggcggggcc ctggccgctc gtctgggccg tgctgcagct gggctggtgg      60
ccaggatggc tcctagactc ccctgacagg ccctggagcc cgctcacctt ctccccggcg     120
cagctcacgg tgcaggaggg agagaacgcc acgttcacct gcagcctggc cgacatcccc     180
gacagcttcg tgctcaactg gtaccgcctg agccccgca accagacgga caagctggcc      240
gccttccagg aggaccgcat cgagcccggc cgggacaggc gcttccgcgt catgcggctg     300
cccaacgggc gggacttcca catgagcatc gtcgctgcgc gcctcaacga cagcggcatc     360
tacctgtgcg gggccatcta cctgcccccc aacacacaga tcaacgagag tccccgcgca    420
gagctctccg tgacggagag aaccctggag ccccccacac agagcccag ccccccaccc     480
agactcagcg gccagttgca ggggctggtc atcggcgtca cgagcgtgct ggtgggtgtc    540
ctgctactgc tgctgctgac ctgggtcctg gccgctgtct tccccagggc cacccgaggt    600
gcctgtgtgt gcgggagcga ggacgagcct ctgaaggagg ccccgatgc agcgcccgtc     660
ttcaccctgg actacgggga gctggacttc agtggcgag agaagacgcc ggagccccg     720
gcgccctgtg ccccggagca gaccgagtat gccaccatcg tcttcccggg caggccggcg    780
tccccgggcc gcagggcctc ggccagcagc ctgcaggag cccagcctcc gagccccgag    840
gacggacccg gcctgtggcc cctctga                                         867
```

<210> SEQ ID NO 36
<211> LENGTH: 288
<212> TYPE: PRT
<213> ORGANISM: Canis familiaris

<400> SEQUENCE: 36

```
Met Gly Ser Arg Arg Gly Pro Trp Pro Leu Val Trp Ala Val Leu Gln
1               5                   10                  15

Leu Gly Trp Trp Pro Gly Trp Leu Leu Asp Ser Pro Asp Arg Pro Trp
            20                  25                  30

Ser Pro Leu Thr Phe Ser Pro Ala Gln Leu Thr Val Gln Glu Gly Glu
        35                  40                  45

Asn Ala Thr Phe Thr Cys Ser Leu Ala Asp Ile Pro Asp Ser Phe Val
    50                  55                  60

Leu Asn Trp Tyr Arg Leu Ser Pro Arg Asn Gln Thr Asp Lys Leu Ala
65                  70                  75                  80

Ala Phe Gln Glu Asp Arg Ile Glu Pro Gly Arg Asp Arg Arg Phe Arg
                85                  90                  95

Val Met Arg Leu Pro Asn Gly Arg Asp Phe His Met Ser Ile Val Ala
            100                 105                 110

Ala Arg Leu Asn Asp Ser Gly Ile Tyr Leu Cys Gly Ala Ile Tyr Leu
        115                 120                 125

Pro Pro Asn Thr Gln Ile Asn Glu Ser Pro Arg Ala Glu Leu Ser Val
    130                 135                 140

Thr Glu Arg Thr Leu Glu Pro Pro Thr Gln Ser Pro Ser Pro Pro
145                 150                 155                 160

Arg Leu Ser Gly Gln Leu Gln Gly Leu Val Ile Gly Val Thr Ser Val
                165                 170                 175

Leu Val Gly Val Leu Leu Leu Leu Leu Leu Thr Trp Val Leu Ala Ala
```

```
            180                 185                 190
Val Phe Pro Arg Ala Thr Arg Gly Ala Cys Val Cys Gly Ser Glu Asp
            195                 200                 205

Glu Pro Leu Lys Glu Gly Pro Asp Ala Ala Pro Val Phe Thr Leu Asp
            210                 215                 220

Tyr Gly Glu Leu Asp Phe Gln Trp Arg Glu Lys Thr Pro Glu Pro Pro
225                 230                 235                 240

Ala Pro Cys Ala Pro Glu Gln Thr Glu Tyr Ala Thr Ile Val Phe Pro
                245                 250                 255

Gly Arg Pro Ala Ser Pro Gly Arg Arg Ala Ser Ala Ser Ser Leu Gln
            260                 265                 270

Gly Ala Gln Pro Pro Ser Pro Glu Asp Gly Pro Gly Leu Trp Pro Leu
            275                 280                 285
```

<210> SEQ ID NO 37
<211> LENGTH: 870
<212> TYPE: DNA
<213> ORGANISM: Canis familiaris

<400> SEQUENCE: 37

```
atgagaatgt ttagtgtctt tacattcatg gcctactgcc atttgctaaa agcatttacg    60
atcacagttt ctaaggacct gtatgtggta gagtatggtg gcaatgtgac aatggaatgc   120
aaattcccgg tggaaaaaca gttaaacttg tttgcactaa tcgtctactg ggaaatggag   180
gataaaaaaa ttatacaatt tgtgaatgga aggaagacc tgaaagttca gcacagcagc   240
tacagccaga gggctcagct attgaaggac cagctcttct ggggaaggc tgcgcttcag   300
atcacagatg tgagattgca ggatgcaggg gtttactgct gcttgatcgg ctatggcggt   360
gctgactaca gcggattac tttgaaagtt catgccccgt accgcaacat cagccaaaga   420
atttctgtgg atcctgtcac ctctgaacat gaactaatgt gtcaggctga gggttaccct   480
gaggctgaag tcatctggac aagcagtgac caccgagtcc tgagtggcaa aaccaccatc   540
actaattcca atagggaaga gaagcttttc aatgtgacca gcacgctgaa catcaatgca   600
acagctaatg agatttttcta ctgcactttt caaagatcag gtcctgagga aaacaatact   660
gccgagttgg tcatcccaga cgactgccc gttccagcaa gtgagaggac tcatttcatg   720
attctgggac ctttcctgtt gcttcttggt gtagtcctgg cagtcacttt ctgtctaaaa   780
aaacatggga gaatgatgga tgtggaaaaa tgttgcaccc gagataggaa ctcaaagaaa   840
cgaaatgata tacaatttga agagacataa                                    870
```

<210> SEQ ID NO 38
<211> LENGTH: 289
<212> TYPE: PRT
<213> ORGANISM: Canis familiaris

<400> SEQUENCE: 38

```
Met Arg Met Phe Ser Val Phe Thr Phe Met Ala Tyr Cys His Leu Leu
1               5                   10                  15

Lys Ala Phe Thr Ile Thr Val Ser Lys Asp Leu Tyr Val Val Glu Tyr
            20                  25                  30

Gly Gly Asn Val Thr Met Glu Cys Lys Phe Pro Val Glu Lys Gln Leu
        35                  40                  45

Asn Leu Phe Ala Leu Ile Val Tyr Trp Glu Met Glu Asp Lys Lys Ile
    50                  55                  60

Ile Gln Phe Val Asn Gly Lys Glu Asp Leu Lys Val Gln His Ser Ser
```

```
                65                  70                  75                  80
Tyr Ser Gln Arg Ala Gln Leu Leu Lys Asp Gln Leu Phe Leu Gly Lys
                    85                  90                  95

Ala Ala Leu Gln Ile Thr Asp Val Arg Leu Gln Asp Ala Gly Val Tyr
                100                 105                 110

Cys Cys Leu Ile Gly Tyr Gly Gly Ala Asp Tyr Lys Arg Ile Thr Leu
                115                 120                 125

Lys Val His Ala Pro Tyr Arg Asn Ile Ser Gln Arg Ile Ser Val Asp
            130                 135                 140

Pro Val Thr Ser Glu His Glu Leu Met Cys Gln Ala Glu Gly Tyr Pro
145                 150                 155                 160

Glu Ala Glu Val Ile Trp Thr Ser Ser Asp His Arg Val Leu Ser Gly
                    165                 170                 175

Lys Thr Thr Ile Thr Asn Ser Asn Arg Glu Gly Lys Leu Phe Asn Val
                180                 185                 190

Thr Ser Thr Leu Asn Ile Asn Ala Thr Ala Asn Glu Ile Phe Tyr Cys
                195                 200                 205

Thr Phe Gln Arg Ser Gly Pro Glu Glu Asn Asn Thr Ala Glu Leu Val
            210                 215                 220

Ile Pro Glu Arg Leu Pro Val Pro Ala Ser Glu Arg Thr His Phe Met
225                 230                 235                 240

Ile Leu Gly Pro Phe Leu Leu Leu Leu Gly Val Val Leu Ala Val Thr
                    245                 250                 255

Phe Cys Leu Lys Lys His Gly Arg Met Met Asp Val Glu Lys Cys Cys
                260                 265                 270

Thr Arg Asp Arg Asn Ser Lys Lys Arg Asn Asp Ile Gln Phe Glu Glu
            275                 280                 285

Thr
```

<210> SEQ ID NO 39
<211> LENGTH: 1410
<212> TYPE: DNA
<213> ORGANISM: Artificial Sequence
<220> FEATURE:
<223> OTHER INFORMATION: caninized mouse antibody

<400> SEQUENCE: 39

```
atggccgtgc tggggctgct cttctgcctg gtgacattcc caagctgtgt gctaagcgag      60
gtgcagctgg tgcagtccgg cggcgatctg gtgaagcctg gaggcagcgt gagactgagc     120
tgcgtggcca gcggctacac cttcaccagc tactacctgt actgggtgag gcaggctcct     180
ggcaaaggac tgcagtggat cggcggcgtg aatcctagca acggcggcac caacttcagc     240
gagaagttca agagcagggc caccctgagc gtggacaagg ccaagaacac cgcctacatg     300
cagctgaact ccctgagggc cgaggacacc gccgtgtact actgcaccag agggacagc      360 aactacgacg cggcttcga ctactgggga caggaaccc tgctgaccgt gtccagcgct      420
tccacaacgg ctccgtcggt gtttccctg gcacctagct gcgggtcgac ctcgggtagc     480
acagtggcgc tggcgtgttt ggtgtcggga tactttcccg agccggtaac ggtgtcatgg     540
aactcagggt cacttacatc aggagtccat acttttccgt ccgtgctgca gtcaagcggc     600
ttgcattcac tgtcctcgat ggtgacggtg ccttcgtcga ggtggcccag cgaaacgttc     660
acttgtaacg tagtacaccc ggcctccaac acgaaagtcg ataaaccggt attcaatgag     720
tgcagatgta cagacacccc tccctgtccg gtacccgaac cccttggagg gccgagcgtc     780
```

```
ctcatcttcc ctcccaagcc aaaagacatc ttgcgcatta cgaggacacc agaagtcacg    840
tgcgtagtgc ttgatctcgg tagagaagat cccgaggtcc agatctcgtg gtttgtggat    900
ggaaaggagg tccacaccgc aaagactcag tcgcgcgagc agcagttcaa tggcacgtat    960
cgggtcgtga gcgtgcttcc tatcgagcat caggactggc tcaccgggaa ggagttcaaa   1020
tgccgggtca atcatatcga cctcccgtca ccaatcgagc ggaccatctc gaaggctaga   1080
ggaagggcgc acaaaccttc ggtctatgtg cttcccccat cgcccaaaga gctttcctcg   1140
tcggatacgg tgtccattac atgcttgatt aaggacttct atcctcctga tattgatgtg   1200
gaatggcaat caaacggaca gcaggagccg gaacgcaagc accgaatgac cccaccgcaa   1260
ttggacgaag atggtagcta ctttctctac tcaaagctct cagtcgacaa atcccgatgg   1320
cagcagggag atcccttcac ttgcgccgtg atgcacgaga cactccaaaa tcattacacg   1380 gaccttcgt tgagccactc gcccggaaag                                     1410
```

<210> SEQ ID NO 40
<211> LENGTH: 470
<212> TYPE: PRT
<213> ORGANISM: Artificial Sequence
<220> FEATURE:
<223> OTHER INFORMATION: caninized mouse antibody

<400> SEQUENCE: 40

```
Met Ala Val Leu Gly Leu Leu Phe Cys Leu Val Thr Phe Pro Ser Cys
1               5                   10                  15

Val Leu Ser Glu Val Gln Leu Val Gln Ser Gly Gly Asp Leu Val Lys
            20                  25                  30

Pro Gly Gly Ser Val Arg Leu Ser Cys Val Ala Ser Gly Tyr Thr Phe
        35                  40                  45

Thr Ser Tyr Tyr Leu Tyr Trp Val Arg Gln Ala Pro Gly Lys Gly Leu
    50                  55                  60

Gln Trp Ile Gly Gly Val Asn Pro Ser Asn Gly Gly Thr Asn Phe Ser
65                  70                  75                  80

Glu Lys Phe Lys Ser Arg Ala Thr Leu Ser Val Asp Lys Ala Lys Asn
                85                  90                  95

Thr Ala Tyr Met Gln Leu Asn Ser Leu Arg Ala Glu Asp Thr Ala Val
            100                 105                 110

Tyr Tyr Cys Thr Arg Arg Asp Ser Asn Tyr Asp Gly Phe Asp Tyr
        115                 120                 125

Trp Gly Gln Gly Thr Leu Leu Thr Val Ser Ser Ala Ser Thr Thr Ala
    130                 135                 140

Pro Ser Val Phe Pro Leu Ala Pro Ser Cys Gly Ser Thr Ser Gly Ser
145                 150                 155                 160

Thr Val Ala Leu Ala Cys Leu Val Ser Gly Tyr Phe Pro Glu Pro Val
                165                 170                 175

Thr Val Ser Trp Asn Ser Gly Ser Leu Thr Ser Gly Val His Thr Phe
            180                 185                 190

Pro Ser Val Leu Gln Ser Ser Gly Leu His Ser Leu Ser Ser Met Val
        195                 200                 205

Thr Val Pro Ser Ser Arg Trp Pro Ser Glu Thr Phe Thr Cys Asn Val
    210                 215                 220

Val His Pro Ala Ser Asn Thr Lys Val Asp Lys Pro Val Phe Asn Glu
225                 230                 235                 240

Cys Arg Cys Thr Asp Thr Pro Pro Cys Pro Val Pro Glu Pro Leu Gly
                245                 250                 255
```

```
Gly Pro Ser Val Leu Ile Phe Pro Pro Lys Pro Lys Asp Ile Leu Arg
                260                 265                 270
Ile Thr Arg Thr Pro Glu Val Thr Cys Val Val Leu Asp Leu Gly Arg
            275                 280                 285
Glu Asp Pro Glu Val Gln Ile Ser Trp Phe Val Asp Gly Lys Glu Val
290                 295                 300
His Thr Ala Lys Thr Gln Ser Arg Glu Gln Gln Phe Asn Gly Thr Tyr
305                 310                 315                 320
Arg Val Val Ser Val Leu Pro Ile Glu His Gln Asp Trp Leu Thr Gly
                325                 330                 335
Lys Glu Phe Lys Cys Arg Val Asn His Ile Asp Leu Pro Ser Pro Ile
            340                 345                 350
Glu Arg Thr Ile Ser Lys Ala Arg Gly Arg Ala His Lys Pro Ser Val
        355                 360                 365
Tyr Val Leu Pro Pro Ser Pro Lys Glu Leu Ser Ser Ser Asp Thr Val
    370                 375                 380
Ser Ile Thr Cys Leu Ile Lys Asp Phe Tyr Pro Pro Asp Ile Asp Val
385                 390                 395                 400
Glu Trp Gln Ser Asn Gly Gln Gln Glu Pro Glu Arg Lys His Arg Met
                405                 410                 415
Thr Pro Pro Gln Leu Asp Glu Asp Gly Ser Tyr Phe Leu Tyr Ser Lys
            420                 425                 430
Leu Ser Val Asp Lys Ser Arg Trp Gln Gln Gly Asp Pro Phe Thr Cys
        435                 440                 445
Ala Val Met His Glu Thr Leu Gln Asn His Tyr Thr Asp Leu Ser Leu
    450                 455                 460
Ser His Ser Pro Gly Lys
465                 470

<210> SEQ ID NO 41
<211> LENGTH: 1425
<212> TYPE: DNA
<213> ORGANISM: Artificial Sequence
<220> FEATURE:
<223> OTHER INFORMATION: caninized mouse antibody

<400> SEQUENCE: 41
atggccgtgc tggggctgct cttctgcctg gtgacattcc caagctgtgt gctaagcgag    60
gtgcagctgg tgcagtccgg cggcgatctg gtgaagcctg gaggcagcgt gagactgagc   120
tgcgtggcca gcggctacac cttcaccagc tactacctgt actgggtgag gcaggctcct   180
ggcaaaggac tgcagtggat cggcggcgtg aatcctagca acggcggcac caacttcagc   240
gagaagttca gagcagggc caccctgagc gtggacaagg ccaagaacac cgcctacatg   300
cagctgaact ccctgagggc cgaggacacc gccgtgtact actgcaccag cagggacagc   360
aactacgacg cggcttcga ctactgggga cagggaaccc tgctgaccgt gtccagcgct   420
tccacaaccg cgccatcagt ctttccgttg gccccatcat gcgggtcgac gagcggatcg   480
actgtggccc tggcgtgctt ggtgtcggga tactttcccg aacccgtcac ggtcagctgg   540
aactccggat cgcttacgag cggtgtgcat acgttcccct cggtcttgca atcatcaggg   600
ctctactcgc tgtcgagcat ggtaacggtg ccctcatcga ggtggccctc cgaaacgttc   660
acatgtaacg tagcacatcc agcctccaaa accaaggtgg ataaacccgt gccgaaaaga   720
gagaatgggc gggtgcctcg acccctgat tgccccaagt gtccggctcc ggaaatgctc   780
```

```
ggtggaccct cagtgtttat cttccctccg aagcccaagg acactctgct gatcgcgcgc    840
actccagaag taacatgtgt agtggtggac cttgatcccg aggacccga agtccagatc      900 tcctggtttg tagatgggaa acagatgcag accgcaaaaa ctcaacccag agaggagcag     960
ttcaacggaa ataccgagt ggtatccgtc cttccgattg ccaccagga ctggttgaaa      1020 gggaagcagt ttacgtgtaa agtcaacaat aaggcgttgc ctagccctat tgagcggacg    1080
atttcgaaag ctaggggaca ggcccaccag ccatcggtct atgtccttcc gccttcccgc    1140
gaggagctct cgaagaatac agtgagcctt acatgcctca ttaaggattt cttcccgcct    1200
gatatcgacg tagagtggca atcaaacggt caacaggagc cggaatccaa gtatagaacc    1260
actccgcccc agcttgacga ggacggatca tacttttgt attcaaaact gtcggtggat     1320
aagagccggt ggcagagagg tgacaccttc atctgtgcgg tgatgcacga agcactccat    1380
aatcactaca cccaagagag cctctcgcat tcccccggaa agtga                    1425
```

<210> SEQ ID NO 42
<211> LENGTH: 474
<212> TYPE: PRT
<213> ORGANISM: Artificial Sequence
<220> FEATURE:
<223> OTHER INFORMATION: caninized mouse antibody

<400> SEQUENCE: 42

```
Met Ala Val Leu Gly Leu Leu Phe Cys Leu Val Thr Phe Pro Ser Cys
1               5                   10                  15

Val Leu Ser Glu Val Gln Leu Val Gln Ser Gly Gly Asp Leu Val Lys
            20                  25                  30

Pro Gly Gly Ser Val Arg Leu Ser Cys Val Ala Ser Gly Tyr Thr Phe
        35                  40                  45

Thr Ser Tyr Tyr Leu Tyr Trp Val Arg Gln Ala Pro Gly Lys Gly Leu
    50                  55                  60

Gln Trp Ile Gly Gly Val Asn Pro Ser Asn Gly Gly Thr Asn Phe Ser
65                  70                  75                  80

Glu Lys Phe Lys Ser Arg Ala Thr Leu Ser Val Asp Lys Ala Lys Asn
                85                  90                  95

Thr Ala Tyr Met Gln Leu Asn Ser Leu Arg Ala Glu Asp Thr Ala Val
            100                 105                 110

Tyr Tyr Cys Thr Arg Arg Asp Ser Asn Tyr Asp Gly Gly Phe Asp Tyr
        115                 120                 125

Trp Gly Gln Gly Thr Leu Leu Thr Val Ser Ser Ala Ser Thr Thr Ala
    130                 135                 140

Pro Ser Val Phe Pro Leu Ala Pro Ser Cys Gly Ser Thr Ser Gly Ser
145                 150                 155                 160

Thr Val Ala Leu Ala Cys Leu Val Ser Gly Tyr Phe Pro Glu Pro Val
                165                 170                 175

Thr Val Ser Trp Asn Ser Gly Ser Leu Thr Ser Gly Val His Thr Phe
            180                 185                 190

Pro Ser Val Leu Gln Ser Ser Gly Leu Tyr Ser Leu Ser Ser Met Val
        195                 200                 205

Thr Val Pro Ser Ser Arg Trp Pro Ser Glu Thr Phe Thr Cys Asn Val
    210                 215                 220

Ala His Pro Ala Ser Lys Thr Lys Val Asp Lys Pro Val Pro Lys Arg
225                 230                 235                 240

Glu Asn Gly Arg Val Pro Arg Pro Pro Asp Cys Pro Lys Cys Pro Ala
                245                 250                 255
```

```
Pro Glu Met Leu Gly Gly Pro Ser Val Phe Ile Phe Pro Pro Lys Pro
            260                 265                 270

Lys Asp Thr Leu Leu Ile Ala Arg Thr Pro Glu Val Thr Cys Val Val
            275                 280                 285

Val Asp Leu Asp Pro Glu Asp Pro Glu Val Gln Ile Ser Trp Phe Val
            290                 295                 300

Asp Gly Lys Gln Met Gln Thr Ala Lys Thr Gln Pro Arg Glu Glu Gln
305                 310                 315                 320

Phe Asn Gly Thr Tyr Arg Val Val Ser Val Leu Pro Ile Gly His Gln
                325                 330                 335

Asp Trp Leu Lys Gly Lys Gln Phe Thr Cys Lys Val Asn Asn Lys Ala
            340                 345                 350

Leu Pro Ser Pro Ile Glu Arg Thr Ile Ser Lys Ala Arg Gly Gln Ala
            355                 360                 365

His Gln Pro Ser Val Tyr Val Leu Pro Pro Ser Arg Glu Glu Leu Ser
            370                 375                 380

Lys Asn Thr Val Ser Leu Thr Cys Leu Ile Lys Asp Phe Phe Pro Pro
385                 390                 395                 400

Asp Ile Asp Val Glu Trp Gln Ser Asn Gly Gln Gln Glu Pro Glu Ser
                405                 410                 415

Lys Tyr Arg Thr Thr Pro Pro Gln Leu Asp Glu Asp Gly Ser Tyr Phe
            420                 425                 430

Leu Tyr Ser Lys Leu Ser Val Asp Lys Ser Arg Trp Gln Arg Gly Asp
            435                 440                 445

Thr Phe Ile Cys Ala Val Met His Glu Ala Leu His Asn His Tyr Thr
            450                 455                 460

Gln Glu Ser Leu Ser His Ser Pro Gly Lys
465                 470

<210> SEQ ID NO 43
<211> LENGTH: 1410
<212> TYPE: DNA
<213> ORGANISM: Artificial Sequence
<220> FEATURE:
<223> OTHER INFORMATION: caninized mouse antibody

<400> SEQUENCE: 43
atggccgtgc tggggctgct cttctgcctg gtgacattcc caagctgtgt gctaagcgag      60
gtgcagctgg tgcagtccgg cggcgatctg gtgaagcctg aggcagcgt gagactgagc      120 tgcgtggcca gcggctacac cttcaccagc tactacctgt actgggtgag gcaggctcct      180
ggcaaaggac tgcagtggat cggcggcgtg aatcctagca cggcggcac caacttcagc      240 gagaagttca agagcagggc caccctgagc gtggacaagg ccaagaacac cgcctacatg      300
cagctgaact ccctgagggc cgaggacacc gccgtgtact actgcaccag agggacagc      360 aactacgacg cggcttcga ctactgggga caggaaccc tgctgaccgt gtccagcgct      420
tcaaccacag cgccgagcgt gttccctctg cgccgtcgt gcggttccac ctcgggatca      480
acagtggccc tcgcctgtct cgtgagcgga ctactttccgg agcctgtcac ggtgtcgtgg      540
aatagcggat cactcacgtc gggcgtgcat acttttccat ccgtcttgca atcgagcgga      600
ttgtactcac tctcctcaac cgtcactgtc ccctcgtcgc gctggccctc ggagactttt      660
acgtgcaatg tagtccatcc ggcgagcaac acgaaggtcg acaagcccgt acccaaggaa      720
tcaacatgca agtgcatctc gccctgtccc gtccccgaat cccttggtgg cccctcagtg      780
```

```
tttatcttcc ctccgaagcc taaagacatc ttgagaatca caagaacacc ggaaatcacg   840
tgtgtggtcc ttgacttggg acgcgaggac cctgaggtac aaatctcgtg gtttgtggac   900
gggaaagagg tgcacacagc aaagacacaa ccacgcgagc agcagtttaa ctcaacgtac   960
agggtagtat ccgtacttcc cattgaacac caggattggc tcaccggtaa agaattcaaa  1020
tgccgagtga atcacatcgg gcttcctagc ccaattgagc ggacgatttc caaagctagg  1080
ggtcaggccc accagccgag cgtatacgtg ttgccgccct ccccgaagga gctgtcatcg  1140
tcagatacgg taacgttgac gtgtctgatc aaagatttct ttcctcccga aattgatgtg  1200
gaatggcaaa gcaatgggca gcccgagccc gagtcaaagt accatactac tgcaccacag  1260
ctggacgaag atggatcgta tttcctctac tcgaaactgt ccgtggataa gtcccggtgg  1320
cagcaagggg acaccttcac ttgcgcggtc atgcacgagg cacttcagaa ccactatacg  1380
gacttgagcc tctcgcattc gccagggaag                                    1410
```

<210> SEQ ID NO 44
<211> LENGTH: 470
<212> TYPE: PRT
<213> ORGANISM: Artificial Sequence
<220> FEATURE:
<223> OTHER INFORMATION: caninized mouse antibody

<400> SEQUENCE: 44

```
Met Ala Val Leu Gly Leu Leu Phe Cys Leu Val Thr Phe Pro Ser Cys
1               5                   10                  15

Val Leu Ser Glu Val Gln Leu Val Gln Ser Gly Gly Asp Leu Val Lys
            20                  25                  30

Pro Gly Gly Ser Val Arg Leu Ser Cys Val Ala Ser Gly Tyr Thr Phe
        35                  40                  45

Thr Ser Tyr Tyr Leu Tyr Trp Val Arg Gln Ala Pro Gly Lys Gly Leu
    50                  55                  60

Gln Trp Ile Gly Gly Val Asn Pro Ser Asn Gly Gly Thr Asn Phe Ser
65                  70                  75                  80

Glu Lys Phe Lys Ser Arg Ala Thr Leu Ser Val Asp Lys Ala Lys Asn
                85                  90                  95

Thr Ala Tyr Met Gln Leu Asn Ser Leu Arg Ala Glu Asp Thr Ala Val
            100                 105                 110

Tyr Tyr Cys Thr Arg Arg Asp Ser Asn Tyr Asp Gly Gly Phe Asp Tyr
        115                 120                 125

Trp Gly Gln Gly Thr Leu Leu Thr Val Ser Ser Ala Ser Thr Thr Ala
    130                 135                 140

Pro Ser Val Phe Pro Leu Ala Pro Ser Cys Gly Ser Thr Ser Gly Ser
145                 150                 155                 160

Thr Val Ala Leu Ala Cys Leu Val Ser Gly Tyr Phe Pro Glu Pro Val
                165                 170                 175

Thr Val Ser Trp Asn Ser Gly Ser Leu Thr Ser Gly Val His Thr Phe
            180                 185                 190

Pro Ser Val Leu Gln Ser Ser Gly Leu Tyr Ser Leu Ser Ser Thr Val
        195                 200                 205

Thr Val Pro Ser Ser Arg Trp Pro Ser Glu Thr Phe Thr Cys Asn Val
    210                 215                 220

Val His Pro Ala Ser Asn Thr Lys Val Asp Lys Pro Val Pro Lys Glu
225                 230                 235                 240

Ser Thr Cys Lys Cys Ile Ser Pro Cys Pro Val Pro Glu Ser Leu Gly
                245                 250                 255
```

Gly Pro Ser Val Phe Ile Phe Pro Lys Pro Lys Asp Ile Leu Arg
            260                 265                 270

Ile Thr Arg Thr Pro Glu Ile Thr Cys Val Val Leu Asp Leu Gly Arg
        275                 280                 285

Glu Asp Pro Glu Val Gln Ile Ser Trp Phe Val Asp Gly Lys Glu Val
    290                 295                 300

His Thr Ala Lys Thr Gln Pro Arg Glu Gln Gln Phe Asn Ser Thr Tyr
305                 310                 315                 320

Arg Val Val Ser Val Leu Pro Ile Glu His Gln Asp Trp Leu Thr Gly
                325                 330                 335

Lys Glu Phe Lys Cys Arg Val Asn His Ile Gly Leu Pro Ser Pro Ile
            340                 345                 350

Glu Arg Thr Ile Ser Lys Ala Arg Gly Gln Ala His Gln Pro Ser Val
        355                 360                 365

Tyr Val Leu Pro Pro Ser Pro Lys Glu Leu Ser Ser Ser Asp Thr Val
    370                 375                 380

Thr Leu Thr Cys Leu Ile Lys Asp Phe Phe Pro Glu Ile Asp Val
385                 390                 395                 400

Glu Trp Gln Ser Asn Gly Gln Pro Glu Pro Glu Ser Lys Tyr His Thr
                405                 410                 415

Thr Ala Pro Gln Leu Asp Glu Asp Gly Ser Tyr Phe Leu Tyr Ser Lys
            420                 425                 430

Leu Ser Val Asp Lys Ser Arg Trp Gln Gln Gly Asp Thr Phe Thr Cys
        435                 440                 445

Ala Val Met His Glu Ala Leu Gln Asn His Tyr Thr Asp Leu Ser Leu
    450                 455                 460

Ser His Ser Pro Gly Lys
465                 470

<210> SEQ ID NO 45
<211> LENGTH: 732
<212> TYPE: DNA
<213> ORGANISM: Artificial Sequence
<220> FEATURE:
<223> OTHER INFORMATION: caninized mouse antibody

<400> SEQUENCE: 45

| | | |
|---|---|---|
| atggatatga gagtacctgc acaacttctg ggattgctgc ttctttggct gagaggggcc | | 60 |
| cgctgcgata tcgtcctgac ccagacccct ctgagcctgt ccgtgagccc tggagaaccc | | 120 |
| gccagcatca gctgcagggc ctccaagagc gtgagcacca gcggcttcag ctacctgcac | | 180 |
| tggtacaggc agaagcccgg acagagcccc cagctgctga tcttcctggc agcaacctg | | 240 |
| gagagcggcg tgcctgacag gtttagcgga agcggcagcg gcaccgactt cacactgagg | | 300 |
| atctccaggg tggaagccga cgacgccgga gtgtactact gccagcacag ctgggaactg | | 360 |
| cccctgacct tcggccaggg caccaaggtg gagatcaaga ggaacgacgc tcagccagcc | | 420 |
| gtgtacctct ccagccttc gccggaccag cttcatacgg ggtcagcgtc ggtggtgtgc | | 480 |
| ctgttgaact cgtttttaccc caaggacatt aacgtgaagt ggaaggtaga cggggtaatt | | 540 |
| caagacactg gcattcaaga gtccgtcacg gaacaagact caaagactc aacgtattca | | 600 |
| ctgtcgtcaa ccttgacgat gtcaagcacc gagtatctta gccatgagct gtattcgtgc | | 660 |
| gagatcaccc acaagtccct ccctccact cttatcaaat cctttcagcg gtcggaatgt | | 720 |
| cagcgggtcg at | | 732 |

<210> SEQ ID NO 46
<211> LENGTH: 244
<212> TYPE: PRT
<213> ORGANISM: Artificial Sequence
<220> FEATURE:
<223> OTHER INFORMATION: caninized mouse antibody

<400> SEQUENCE: 46

```
Met Asp Met Arg Val Pro Ala Gln Leu Leu Gly Leu Leu Leu Leu Trp
1               5                   10                  15

Leu Arg Gly Ala Arg Cys Asp Ile Val Leu Thr Gln Thr Pro Leu Ser
            20                  25                  30

Leu Ser Val Ser Pro Gly Glu Pro Ala Ser Ile Ser Cys Arg Ala Ser
        35                  40                  45

Lys Ser Val Ser Thr Ser Gly Phe Ser Tyr Leu His Trp Tyr Arg Gln
50                  55                  60

Lys Pro Gly Gln Ser Pro Gln Leu Leu Ile Phe Leu Ala Ser Asn Leu
65                  70                  75                  80

Glu Ser Gly Val Pro Asp Arg Phe Ser Gly Ser Gly Ser Gly Thr Asp
                85                  90                  95

Phe Thr Leu Arg Ile Ser Arg Val Glu Ala Asp Asp Ala Gly Val Tyr
            100                 105                 110

Tyr Cys Gln His Ser Trp Glu Leu Pro Leu Thr Phe Gly Gln Gly Thr
        115                 120                 125

Lys Val Glu Ile Lys Arg Asn Asp Ala Gln Pro Ala Val Tyr Leu Phe
130                 135                 140

Gln Pro Ser Pro Asp Gln Leu His Thr Gly Ser Ala Ser Val Val Cys
145                 150                 155                 160

Leu Leu Asn Ser Phe Tyr Pro Lys Asp Ile Asn Val Lys Trp Lys Val
                165                 170                 175

Asp Gly Val Ile Gln Asp Thr Gly Ile Gln Glu Ser Val Thr Glu Gln
            180                 185                 190

Asp Ser Lys Asp Ser Thr Tyr Ser Leu Ser Ser Thr Leu Thr Met Ser
        195                 200                 205

Ser Thr Glu Tyr Leu Ser His Glu Leu Tyr Ser Cys Glu Ile Thr His
    210                 215                 220

Lys Ser Leu Pro Ser Thr Leu Ile Lys Ser Phe Gln Arg Ser Glu Cys
225                 230                 235                 240

Gln Arg Val Asp
```

<210> SEQ ID NO 47
<211> LENGTH: 732
<212> TYPE: DNA
<213> ORGANISM: Artificial Sequence
<220> FEATURE:
<223> OTHER INFORMATION: caninized mouse antibody

<400> SEQUENCE: 47

```
atggatatga gagtacctgc acaacttctg ggattgctgc ttcttttggct gagaggggcc      60 cgctgcgata tcgtcctgac ccagacccct cctagcctgt ccgtgagccc tggagaaccc     120
gccagcatca gctgcagggc ctccaagagc gtgagcacca gcggcttcag ctacctgcac     180
tggtacaggc agaagcccgg acagcctcct cagctgctga tcttcctggc cagcaacctg     240
gagagcggcg tgcctgacag gtttagcgga agcggcagcg gcaccgactt cacactgagg     300
atctccaggg tggaagccga cgacgccgga gtgtactact gccagcacag ctgggaactg     360
```

```
cccctgacct tcggccaggg caccaaggtg gagatcaaga ggaacgacgc tcagccagcc    420
gtgtacctct tccagccttc gccggaccag cttcatacgg ggtcagcgtc ggtggtgtgc    480
ctgttgaact cgttttaccc caaggacatt aacgtgaagt ggaaggtaga cggggtaatt    540
caagacactg gcattcaaga gtccgtcacg gaacaagact caaaagactc aacgtattca    600
ctgtcgtcaa ccttgacgat gtcaagcacc gagtatctta gccatgagct gtattcgtgc    660
gagatcaccc acaagtccct cccctccact cttatcaaat cctttcagcg gtcggaatgt    720
cagcgggtcg at                                                        732
```

<210> SEQ ID NO 48
<211> LENGTH: 244
<212> TYPE: PRT
<213> ORGANISM: Artificial Sequence
<220> FEATURE:
<223> OTHER INFORMATION: caninized mouse antibody

<400> SEQUENCE: 48

```
Met Asp Met Arg Val Pro Ala Gln Leu Leu Gly Leu Leu Leu Leu Trp
1               5                   10                  15

Leu Arg Gly Ala Arg Cys Asp Ile Val Leu Thr Gln Thr Pro Pro Ser
                20                  25                  30

Leu Ser Val Ser Pro Gly Glu Pro Ala Ser Ile Ser Cys Arg Ala Ser
            35                  40                  45

Lys Ser Val Ser Thr Ser Gly Phe Ser Tyr Leu His Trp Tyr Arg Gln
        50                  55                  60

Lys Pro Gly Gln Pro Pro Gln Leu Leu Ile Phe Leu Ala Ser Asn Leu
65                  70                  75                  80

Glu Ser Gly Val Pro Asp Arg Phe Ser Gly Ser Gly Ser Gly Thr Asp
                85                  90                  95

Phe Thr Leu Arg Ile Ser Arg Val Glu Ala Asp Asp Ala Gly Val Tyr
                100                 105                 110

Tyr Cys Gln His Ser Trp Glu Leu Pro Leu Thr Phe Gly Gln Gly Thr
            115                 120                 125

Lys Val Glu Ile Lys Arg Asn Asp Ala Gln Pro Ala Val Tyr Leu Phe
        130                 135                 140

Gln Pro Ser Pro Asp Gln Leu His Thr Gly Ser Ala Ser Val Val Cys
145                 150                 155                 160

Leu Leu Asn Ser Phe Tyr Pro Lys Asp Ile Asn Val Lys Trp Lys Val
                165                 170                 175

Asp Gly Val Ile Gln Asp Thr Gly Ile Gln Glu Ser Val Thr Glu Gln
                180                 185                 190

Asp Ser Lys Asp Ser Thr Tyr Ser Leu Ser Ser Thr Leu Thr Met Ser
            195                 200                 205

Ser Thr Glu Tyr Leu Ser His Glu Leu Tyr Ser Cys Glu Ile Thr His
        210                 215                 220

Lys Ser Leu Pro Ser Thr Leu Ile Lys Ser Phe Gln Arg Ser Glu Cys
225                 230                 235                 240

Gln Arg Val Asp
```

<210> SEQ ID NO 49
<211> LENGTH: 336
<212> TYPE: PRT
<213> ORGANISM: Canis familiaris

<400> SEQUENCE: 49

```
Ser Ala Ser Thr Thr Ala Pro Ser Val Phe Pro Leu Ala Pro Ser Cys
1               5                   10                  15

Gly Ser Thr Ser Gly Ser Thr Val Ala Leu Ala Cys Leu Val Ser Gly
            20                  25                  30

Tyr Phe Pro Glu Pro Val Thr Val Ser Trp Asn Ser Gly Ser Leu Thr
            35                  40                  45

Ser Gly Val His Thr Phe Pro Ser Val Leu Gln Ser Ser Gly Leu Tyr
        50                  55                  60

Ser Leu Ser Ser Met Val Thr Val Pro Ser Ser Arg Trp Pro Ser Glu
65                  70                  75                  80

Thr Phe Thr Cys Asn Val Ala His Pro Ala Ser Lys Thr Lys Val Asp
                85                  90                  95

Lys Pro Val Pro Lys Arg Glu Asn Gly Arg Val Pro Arg Pro Pro Asp
                100                 105                 110

Cys Pro Lys Cys Pro Ala Pro Glu Met Leu Gly Gly Pro Ser Val Phe
            115                 120                 125

Ile Phe Pro Pro Lys Pro Lys Asp Thr Leu Leu Ile Ala Arg Thr Pro
        130                 135                 140

Glu Val Thr Cys Val Val Val Asp Leu Asp Pro Glu Asp Pro Glu Val
145                 150                 155                 160

Gln Ile Ser Trp Phe Val Asp Gly Lys Gln Met Gln Thr Ala Lys Thr
                165                 170                 175

Gln Pro Arg Glu Glu Gln Phe Asn Gly Thr Tyr Arg Val Val Ser Val
            180                 185                 190

Leu Pro Ile Gly His Gln Asp Trp Leu Lys Gly Lys Gln Phe Thr Cys
        195                 200                 205

Lys Val Asn Asn Lys Ala Leu Pro Ser Pro Ile Glu Arg Thr Ile Ser
        210                 215                 220

Lys Ala Arg Gly Gln Ala His Gln Pro Ser Val Tyr Val Leu Pro Pro
225                 230                 235                 240

Ser Arg Glu Glu Leu Ser Lys Asn Thr Val Ser Leu Thr Cys Leu Ile
                245                 250                 255

Lys Asp Phe Phe Pro Pro Asp Ile Asp Val Glu Trp Gln Ser Asn Gly
            260                 265                 270

Gln Gln Glu Pro Glu Ser Lys Tyr Arg Thr Thr Pro Pro Gln Leu Asp
            275                 280                 285

Glu Asp Gly Ser Tyr Phe Leu Tyr Ser Lys Leu Ser Val Asp Lys Ser
        290                 295                 300

Arg Trp Gln Arg Gly Asp Thr Phe Ile Cys Ala Val Met His Glu Ala
305                 310                 315                 320

Leu His Asn His Tyr Thr Gln Glu Ser Leu Ser His Ser Pro Gly Lys
                325                 330                 335
```

<210> SEQ ID NO 50
<211> LENGTH: 331
<212> TYPE: PRT
<213> ORGANISM: Artificial Sequence
<220> FEATURE:
<223> OTHER INFORMATION: modified canine sequence

<400> SEQUENCE: 50

```
Ser Ala Ser Thr Thr Ala Pro Ser Val Phe Pro Leu Ala Pro Ser Cys
1               5                   10                  15

Gly Ser Thr Ser Gly Ser Thr Val Ala Leu Ala Cys Leu Val Ser Gly
            20                  25                  30
```

Tyr Phe Pro Glu Pro Val Thr Val Ser Trp Asn Ser Gly Ser Leu Thr
                35                  40                  45

Ser Gly Val His Thr Phe Pro Ser Val Leu Gln Ser Ser Gly Leu Tyr
 50                  55                  60

Ser Leu Ser Ser Met Val Thr Val Pro Ser Ser Arg Trp Pro Ser Glu
 65                  70                  75                  80

Thr Phe Thr Cys Asn Val Ala His Pro Ala Ser Lys Thr Lys Val Asp
                85                  90                  95

Lys Pro Val Phe Asn Glu Cys Arg Cys Thr Asp Thr Pro Pro Cys Pro
                100                 105                 110

Ala Pro Glu Met Leu Gly Gly Pro Ser Val Phe Ile Phe Pro Pro Lys
                115                 120                 125

Pro Lys Ala Thr Leu Leu Ile Ala Arg Thr Pro Glu Val Thr Cys Val
                130                 135                 140

Val Val Asp Leu Asp Pro Glu Asp Pro Glu Val Gln Ile Ser Trp Phe
145                 150                 155                 160

Val Asp Gly Lys Gln Met Gln Thr Ala Lys Thr Gln Pro Arg Glu Glu
                165                 170                 175

Gln Phe Ala Gly Thr Tyr Arg Val Val Ser Val Leu Pro Ile Gly His
                180                 185                 190

Gln Asp Trp Leu Lys Gly Lys Gln Phe Thr Cys Lys Val Asn Asn Lys
                195                 200                 205

Ala Leu Pro Ser Pro Ile Glu Arg Thr Ile Ser Lys Ala Arg Gly Gln
                210                 215                 220

Ala His Gln Pro Ser Val Tyr Val Leu Pro Pro Ser Arg Glu Glu Leu
225                 230                 235                 240

Ser Lys Asn Thr Val Ser Leu Thr Cys Leu Ile Lys Asp Phe Phe Pro
                245                 250                 255

Pro Asp Ile Asp Val Glu Trp Gln Ser Asn Gly Gln Gln Glu Pro Glu
                260                 265                 270

Ser Lys Tyr Arg Thr Thr Pro Pro Gln Leu Asp Glu Asp Gly Ser Tyr
                275                 280                 285

Phe Leu Tyr Ser Lys Leu Ser Val Asp Lys Ser Arg Trp Gln Arg Gly
290                 295                 300

Asp Thr Phe Ile Cys Ala Val Met His Glu Ala Leu His Asn His Tyr
305                 310                 315                 320

Thr Gln Glu Ser Leu Ser His Ser Pro Gly Lys
                325                 330

```
<210> SEQ ID NO 51
<211> LENGTH: 331
<212> TYPE: PRT
<213> ORGANISM: Artificial Sequence
<220> FEATURE:
<223> OTHER INFORMATION: modified canine sequence

<400> SEQUENCE: 51
```

Ser Ala Ser Thr Thr Ala Pro Ser Val Phe Pro Leu Ala Pro Ser Cys
1                   5                  10                  15

Gly Ser Thr Ser Gly Ser Thr Val Ala Leu Ala Cys Leu Val Ser Gly
                20                  25                  30

Tyr Phe Pro Glu Pro Val Thr Val Ser Trp Asn Ser Gly Ser Leu Thr
                35                  40                  45

Ser Gly Val His Thr Phe Pro Ser Val Leu Gln Ser Ser Gly Leu Tyr
 50                  55                  60

```
Ser Leu Ser Ser Met Val Thr Val Pro Ser Ser Arg Trp Pro Ser Glu
 65                  70                  75                  80

Thr Phe Thr Cys Asn Val Ala His Pro Ala Ser Lys Thr Lys Val Asp
                 85                  90                  95

Lys Pro Val Pro Lys Glu Ser Thr Cys Lys Cys Ile Ser Pro Cys Pro
            100                 105                 110

Ala Pro Glu Met Leu Gly Gly Pro Ser Val Phe Ile Phe Pro Pro Lys
        115                 120                 125

Pro Lys Ala Thr Leu Leu Ile Ala Arg Thr Pro Glu Val Thr Cys Val
    130                 135                 140

Val Val Asp Leu Asp Pro Glu Asp Pro Glu Val Gln Ile Ser Trp Phe
145                 150                 155                 160

Val Asp Gly Lys Gln Met Gln Thr Ala Lys Thr Gln Pro Arg Glu Glu
                165                 170                 175

Gln Phe Ala Gly Thr Tyr Arg Val Val Ser Val Leu Pro Ile Gly His
            180                 185                 190

Gln Asp Trp Leu Lys Gly Lys Gln Phe Thr Cys Lys Val Asn Asn Lys
        195                 200                 205

Ala Leu Pro Ser Pro Ile Glu Arg Thr Ile Ser Lys Ala Arg Gly Gln
    210                 215                 220

Ala His Gln Pro Ser Val Tyr Val Leu Pro Pro Ser Arg Glu Glu Leu
225                 230                 235                 240

Ser Lys Asn Thr Val Ser Leu Thr Cys Leu Ile Lys Asp Phe Phe Pro
                245                 250                 255

Pro Asp Ile Asp Val Glu Trp Gln Ser Asn Gly Gln Gln Glu Pro Glu
            260                 265                 270

Ser Lys Tyr Arg Thr Thr Pro Pro Gln Leu Asp Glu Asp Gly Ser Tyr
        275                 280                 285

Phe Leu Tyr Ser Lys Leu Ser Val Asp Lys Ser Arg Trp Gln Arg Gly
    290                 295                 300

Asp Thr Phe Ile Cys Ala Val Met His Glu Ala Leu His Asn His Tyr
305                 310                 315                 320

Thr Gln Glu Ser Leu Ser His Ser Pro Gly Lys
                325                 330

<210> SEQ ID NO 52
<211> LENGTH: 336
<212> TYPE: PRT
<213> ORGANISM: Artificial Sequence
<220> FEATURE:
<223> OTHER INFORMATION: modified canine sequence

<400> SEQUENCE: 52

Ser Ala Ser Thr Thr Ala Pro Ser Val Phe Pro Leu Ala Pro Ser Cys
 1               5                  10                  15

Gly Ser Thr Ser Gly Ser Thr Val Ala Leu Ala Cys Leu Val Ser Gly
                20                  25                  30

Tyr Phe Pro Glu Pro Val Thr Val Ser Trp Asn Ser Gly Ser Leu Thr
            35                  40                  45

Ser Gly Val His Thr Phe Pro Ser Val Leu Gln Ser Ser Gly Leu Tyr
        50                  55                  60

Ser Leu Ser Ser Met Val Thr Val Pro Ser Ser Arg Trp Pro Ser Glu
 65                  70                  75                  80

Thr Phe Thr Cys Asn Val Ala His Pro Ala Ser Lys Thr Lys Val Asp
                 85                  90                  95
```

```
Lys Pro Val Pro Lys Arg Glu Asn Gly Arg Val Arg Pro Pro Asp
            100                 105                 110
Cys Pro Lys Cys Pro Ala Pro Glu Met Leu Gly Gly Pro Ser Val Phe
        115                 120                 125
Ile Phe Pro Pro Lys Pro Lys Ala Thr Leu Leu Ile Ala Arg Thr Pro
    130                 135                 140
Glu Val Thr Cys Val Val Val Asp Leu Asp Pro Glu Asp Pro Glu Val
145                 150                 155                 160
Gln Ile Ser Trp Phe Val Asp Gly Lys Gln Met Gln Thr Ala Lys Thr
                165                 170                 175
Gln Pro Arg Glu Glu Gln Phe Ala Gly Thr Tyr Arg Val Val Ser Val
            180                 185                 190
Leu Pro Ile Gly His Gln Asp Trp Leu Lys Gly Lys Gln Phe Thr Cys
        195                 200                 205
Lys Val Asn Asn Lys Ala Leu Pro Ser Pro Ile Glu Arg Thr Ile Ser
    210                 215                 220
Lys Ala Arg Gly Gln Ala His Gln Pro Ser Val Tyr Val Leu Pro Pro
225                 230                 235                 240
Ser Arg Glu Glu Leu Ser Lys Asn Thr Val Ser Leu Thr Cys Leu Ile
                245                 250                 255
Lys Asp Phe Phe Pro Pro Asp Ile Asp Val Glu Trp Gln Ser Asn Gly
            260                 265                 270
Gln Gln Glu Pro Glu Ser Lys Tyr Arg Thr Thr Pro Pro Gln Leu Asp
        275                 280                 285
Glu Asp Gly Ser Tyr Phe Leu Tyr Ser Lys Leu Ser Val Asp Lys Ser
    290                 295                 300
Arg Trp Gln Arg Gly Asp Thr Phe Ile Cys Ala Val Met His Glu Ala
305                 310                 315                 320
Leu His Asn His Tyr Thr Gln Glu Ser Leu Ser His Ser Pro Gly Lys
                325                 330                 335

<210> SEQ ID NO 53
<211> LENGTH: 401
<212> TYPE: PRT
<213> ORGANISM: Artificial Sequence
<220> FEATURE:
<223> OTHER INFORMATION: canine and human

<400> SEQUENCE: 53

Met Asn Phe Leu Leu Ser Trp Val His Trp Ser Leu Ala Leu Leu Leu
1               5                   10                  15
Tyr Leu His His Ala Lys Trp Ser Gln Ala Leu Asp Ser Pro Asp Arg
                20                  25                  30
Pro Trp Ser Pro Leu Thr Phe Ser Pro Ala Gln Leu Thr Val Gln Glu
            35                  40                  45
Gly Glu Asn Ala Thr Phe Thr Cys Ser Leu Ala Asp Ile Pro Asp Ser
    50                  55                  60
Phe Val Leu Asn Trp Tyr Arg Leu Ser Pro Arg Asn Gln Thr Asp Lys
65                  70                  75                  80
Leu Ala Ala Phe Gln Glu Asp Arg Ile Glu Pro Gly Arg Asp Arg Arg
                85                  90                  95
Phe Arg Val Met Arg Leu Pro Asn Gly Arg Asp Phe His Met Ser Ile
            100                 105                 110
Val Ala Ala Arg Leu Asn Asp Ser Gly Ile Tyr Leu Cys Gly Ala Ile
        115                 120                 125
```

-continued

```
Tyr Leu Pro Pro Asn Thr Gln Ile Asn Glu Ser Pro Arg Ala Glu Leu
        130             135             140

Ser Val Thr Glu Arg Thr Leu Glu Pro Pro Thr Gln Ser Pro Ser Pro
145             150             155             160

Pro Pro Arg Leu Ser Gly Gln Leu Gln Gly Leu Val Gly Thr Asp Lys
            165             170             175

Thr His Thr Cys Pro Pro Cys Pro Ala Pro Glu Leu Leu Gly Gly Pro
            180             185             190

Ser Val Phe Leu Phe Pro Pro Lys Pro Lys Asp Thr Leu Met Ile Ser
        195             200             205

Arg Thr Pro Glu Val Thr Cys Val Val Val Asp Val Ser His Glu Asp
        210             215             220

Pro Glu Val Lys Phe Asn Trp Tyr Val Asp Gly Val Glu Val His Asn
225             230             235             240

Ala Lys Thr Lys Pro Arg Glu Glu Gln Tyr Asn Ser Thr Tyr Arg Val
            245             250             255

Val Ser Val Leu Thr Val Leu His Gln Asp Trp Leu Asn Gly Lys Glu
            260             265             270

Tyr Lys Cys Lys Val Ser Asn Lys Ala Leu Pro Ala Pro Ile Glu Lys
        275             280             285

Thr Ile Ser Lys Ala Lys Gly Gln Pro Arg Glu Pro Gln Val Tyr Thr
        290             295             300

Leu Pro Pro Ser Arg Asp Glu Leu Thr Lys Asn Gln Val Ser Leu Thr
305             310             315             320

Cys Leu Val Lys Gly Phe Tyr Pro Ser Asp Ile Ala Val Glu Trp Glu
            325             330             335

Ser Asn Gly Gln Pro Glu Asn Asn Tyr Lys Thr Thr Pro Pro Val Leu
            340             345             350

Asp Ser Asp Gly Ser Phe Phe Leu Tyr Ser Lys Leu Thr Val Asp Lys
        355             360             365

Ser Arg Trp Gln Gln Gly Asn Val Phe Ser Cys Ser Val Met His Glu
        370             375             380

Ala Leu His Asn His Tyr Thr Gln Lys Ser Leu Ser Leu Ser Pro Gly
385             390             395             400

Lys
```